(12) United States Patent
Geiss-Friedlander et al.

(10) Patent No.: US 9,593,148 B2
(45) Date of Patent: Mar. 14, 2017

(54) DPP8 AND DPP9 PEPTIDE INHIBITORS

(71) Applicant: GEORG-AUGUST-UNIVERSITAT GOTTINGEN STIFTUNG OFFENTLICHEN RECHTS, UNIVERSITATSMEDIZIN, Gottimgen (DE)

(72) Inventors: Ruth Geiss-Friedlander, Northeim (DE); Esther Pilla, Gottingen (DE)

(73) Assignee: GEORG-AUGUST-UNIVERSITAT GOTTINGEN STIFTUNG OFFENTLICHEN RECHTS, Gottingen (DE)

( * ) Notice: Subject to any disclaimer, the term of this patent is extended or adjusted under 35 U.S.C. 154(b) by 0 days.

(21) Appl. No.: 14/438,107

(22) PCT Filed: Oct. 31, 2013

(86) PCT No.: PCT/EP2013/072756
§ 371 (c)(1),
(2) Date: Apr. 23, 2015

(87) PCT Pub. No.: WO2014/068023
PCT Pub. Date: May 8, 2014

(65) Prior Publication Data
US 2015/0266922 A1    Sep. 24, 2015

Related U.S. Application Data

(60) Provisional application No. 61/722,017, filed on Nov. 2, 2012.

(51) Int. Cl.
| | | |
|---|---|---|
| A61K 38/00 | (2006.01) | |
| C07K 9/00 | (2006.01) | |
| C07K 7/08 | (2006.01) | |
| C07K 14/47 | (2006.01) | |
| C12Q 1/37 | (2006.01) | |
| C12N 9/48 | (2006.01) | |
| C07K 7/06 | (2006.01) | |

(52) U.S. Cl.
CPC ............. *C07K 7/08* (2013.01); *C07K 7/06* (2013.01); *C07K 14/47* (2013.01); *C12N 9/485* (2013.01); *C12Q 1/37* (2013.01); *C12Y 304/14002* (2013.01); *C12Y 304/14005* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 2002/0115843 A1* | 8/2002 | Oi ........................ | C12N 9/48 536/23.2 |
| 2008/0293618 A1 | 11/2008 | Heiser et al. | |
| 2011/0218142 A1 | 9/2011 | Bachovchin et al. | |

FOREIGN PATENT DOCUMENTS

| | | |
|---|---|---|
| WO | 2005106021 | 11/2005 |
| WO | 2005106487 | 11/2005 |
| WO | 2011113895 | 9/2011 |

OTHER PUBLICATIONS

Pilla et al. The SUMO1-E67 Interacting Loop Peptide Is an Allosteric Inhibitor of the Dipeptidyl Peptidases 8 and 9 Nov. 8, 2013 vol. 288 No. 45 Journal of Biological Chemistry.*
Generick et al. General Chemical Ligation Approach Towards Isopeptide-Linked Ubiquitin and Ubiquitin-Like Assay Reagents, ChemBioChem 2012, 13, 293-297.*
Abbott CA, Yu DM, Woollatt E, Sutherland GR, McCaughan GW & Gorrell MD (2000) Cloning, expression and chromosomal localization of a novel human dipeptidyl peptidase (DPP) IV homolog, DPP8. Eur J Biochem 267: 6140-6150.
Ajami K, Abbott CA, McCaughan GW & Gorrell MD (2004) Dipeptidyl peptidase 9 has two forms, a broad tissue distribution, cytoplasmic localization and DPIV-like peptidase activity. Biochim. Biophys. Acta 1679: 18-28.
Baba D, Maita N, Jee J-G, Uchirnura Y, Saitoh H, Sugasawa K, Hanaoka F, Tochio H, Hiroaki H & Shirakawa M (2005) Crystal structure of thymine DNA glycosylase conjugated to SUMO-1. Nature 435: 979-982.
Bossis G & Melchior F (2006) Regulation of SUMOylation by Reversible Oxidation of SUMO Conjugating Enzymes. Molecular Cell 21: 349-357.
Chang C-C, Naik MT, Huang Y-S, Jeng J-C, Liao P-H, Kuo H-Y, Ho C-C, Hsieh Y-L, Lin C-H, Huang N-J, Naik NM, Kung CC-H, Lin S-Y, Chen R-H, Chang K-S, Huang T-H & Shih H-M (2011) Structural and functional roles of Daxx SIM phosphorylation in SUMO paralog-selective binding and apoptosis modulation. Molecular Cell 42: 62-74.
Geiss-Friedlander R & Melchior F (2007) Concepts in sumoylation: a decade on. Nat. Rev. Mol. Cell Biol. 8: 947-956.
Geiss-Friedlander R, Parmentier N, Möller U, Urlaub H, Van den Eynde BJ & Melchior F (2009) The cytoplasmic peptidase DPP9 is rate-limiting for degradation of proline-containing peptides. J. Biol. Chem. 284: 27211-27219.
Hannich JT, Lewis A, Kroetz MB, Li S-J, Heide H, Emili A & Hochstrasser M (2005) Defining the SUMO-modified proteome by multiple approaches in *Saccharomyces cerevisiae*. J. Biol. Chem. 280: 4102-4110.
Hecker C-M, Rabiller M, Haglund K, Bayer P & Dikic I (2006) Specification of SUMO1- and SUMO2-interacting motifs. J. Biol. Chem. 281:16117-16127.
Knipscheer P, van Dijk WJ, Olsen JV, Mann M & Sixma TK (2007) Noncovalent interaction between Ubc9 and SUMO promotes SUMO chain formation. The EMBO Journal 26: 2797-2807.
Lu C, Tilan JU, Everhart L, Czarnecka M, Soldin SJ, Mendu DR, Jeha D, Hanafy J, Lee CK, Sun J, Izycka-Swieszewska E, Toretsky JA & Kitlinska J (2011) Dipeptidyl peptidases as survival factors in Ewing sarcoma family of tumors: implications for tumor biology and therapy. Journal of Biological Chemistry 286: 27494-27505.

(Continued)

*Primary Examiner* — Jeanette Lieb
(74) *Attorney, Agent, or Firm* — Birch, Stewart, Kolasch & Birch, LLP

(57) ABSTRACT

The present invention relates to non-competitive allosteric peptide inhibitors of DPP9 and/or DPP8, competitive peptides binding to SUMO1, nucleic acid molecules and expression vectors coding said peptide inhibitors, host cells expressing said inhibitors, kits comprising said inhibitors, as well as methods of producing said inhibitors, and uses of said peptide inhibitors; as further defined in the Claims.

17 Claims, 17 Drawing Sheets

(56) References Cited

OTHER PUBLICATIONS

Meulmeester E, Kunze M, Hsiao HH, Urlaub H & Melchior F (2008) Mechanism and Consequences for Paralog-Specific Sumoylation of Ubiquitin-Specific Protease 25. Molecular Cell 30: 610-619.

Park J. Knott HM, Nadvi NA, Collyer CA, Wang XM, Church WB & Gorrell MD (2008) Reversible Inactivation of Human Dipeptidyl Peptidases 8 and 9 by Oxidation. TOEIJ 1: 52-60.

Pichler A, Gast A, Seeler J-S, Dejean A & Melchior F (2002) The nucleoporin RanBP2 has SUMO1 E3 ligase activity. Cell 108: 109-120.

Reverter D & Lima CD (2005) Insights into E3 ligase activity revealed by a SUMO—RanGAP1—Ubc9—Nup358 complex. Nature 435: 687-692.

Rummey C & Metz G (2006) Homology models of dipeptidyl peptidases 8 and 9 with a focus on loop predictions near the active site. Proteins 66: 160-171.

Sauer G, Körner R, Hanisch A, Ries A, Nigg EA & Silljé HHW (2005) Proteome analysis of the human mitotic spindle. Mol. Cell Proteomics 4: 35-43.

Schade J, Stephan M, Schmiedl A, Wagner L, Niestroj AJ, Demuth H-U, Frerker N, Klemann C, Raber KA, Pabst R & Hörsten von S (2008) Regulation of expression and function of dipeptidyl peptidase 4 (DP4), DP8/9, and DP10 in allergic responses of the lung in rats. J. Histochem. Cytochem. 56: 147-155.

Song J, Durrin LK, Wilkinson TA, Krontiris TG & Chen Y (2004) Identification of a SUMO-binding motif that recognizes SUMO-modified proteins. Proc. Natl. Acad. Sci. U.S.A. 101: 14373-14378.

Tang H-K, Chen K-C, Liou G-G, Cheng S-C, Chien C-H, Tang H-Y, Huang L-H, Chang H-P, Chou C-Y & Chen X (2011) Role of a propeller loop in the quaternary structure and enzymatic activity of prolyl dipeptidases DPP-IV and DPP9. FEBS Letters 585: 3409-3414.

Tang H-K, Tang H-Y, Hsu S-C, Chu Y-R, Chien C-H, Shu C-H & Chen X (2009) Biochemical properties and expression profile of human prolyl dipeptidase DPP9. Archives of Biochemistry and Biophysics 485: 120-127.

Van Goethem S, Matheeussen V, Joossens J, Lambeir A-M, Chen X, De Meester I, Haemers A, Augustyns K & Van der Veken P (2011) Structure-Activity Relationship Studies on Isoindoline Inhibitors of Dipeptidyl Peptidases 8 and 9 (DPP8, DPP9): Is DPP8-Selectivity an Attainable Goal? J. Med. Chem. 54: 5737-5746.

Yao T-W, Kim W-S, Yu DM, Sharbeen G, McCaughan GW, Choi K-Y, Xia P & Gorrell MD (2011) A Novel Role of Dipeptidyl Peptidase 9 in Epidermal Growth Factor Signaling. Mol Cancer Res 7: 948-959.

Yu DMT, Ajami K, Gall MG, Park J, Lee CS, Evans KA, McLaughlin EA, Pitman MR, Abbott CA, McCaughan GW & Gorrell MD (2009) The in vivo expression of dipeptidyl peptidases 8 and 9. J. Histochem. Cytochem. 57: 1025-1040.

Yu DMT, Wang XM, McCaughan GW & Gorrell MD (2006) Extraenzymatic functions of the dipeptidyl peptidase IV-related proteins DP8 and DP9 in cell adhesion, migration and apoptosis. FEBS Journal 273: 2447-2460.

Zhang H, Chen Y, Keane FM (2013) Advances in Understanding the Expression and Function of Dipeptidyl Peptidase 8 and 9. Molecular Cancer Research (published online Sep. 13, 2013).

Pilla Esther et al: "The SUMO1-E67 Interacting Loop Peptide Is an Allosteric Inhibitor of the Dipeptidyl Peptidases 8 and 9", Journal of Biological Chemistry, vol. 288, No. 45, Sep. 26, 2013 (Sep. 26, 2013), pp. 32787-32796, XP002720362.

Pilla Esther et al: "A Novel SUMO1-specific Interacting Motif in Dipeptidyl Peptidase 9 (DPP9) That Is Important for Enzymatic Regulation", Journal of Biological Chemistry, vol. 287, No. 53, Nov. 14, 2012 (Nov. 14, 2012), pp. 44320-44329, XP002720363.

Van Der Veken P et al: "Inhibitors of dipeptidyl peptidase 8 and dipeptidyl peptidase 9. Part 1: Identification of dipeptide derived leads", Bioorganic & Medicinal Chemistry Letters, Pergamon, Amsterdam, NL, vol. 18, No. 14, Jul. 15, 2008 (Jul. 15, 2008), pp. 4154-4158, XP022852919, ISSN: 0960-894X, DOI: 10.1016/J.BMCL.2008.05.080 [retrieved on May 24, 2008].

Morris May et al: "A peptide carrier for the delivery of biologically active proteins into mammalian cells", Nature Biotechnology, vol. 19, Dec. 2001, pp. 1173-1176.

* cited by examiner

Figure 1 A-C
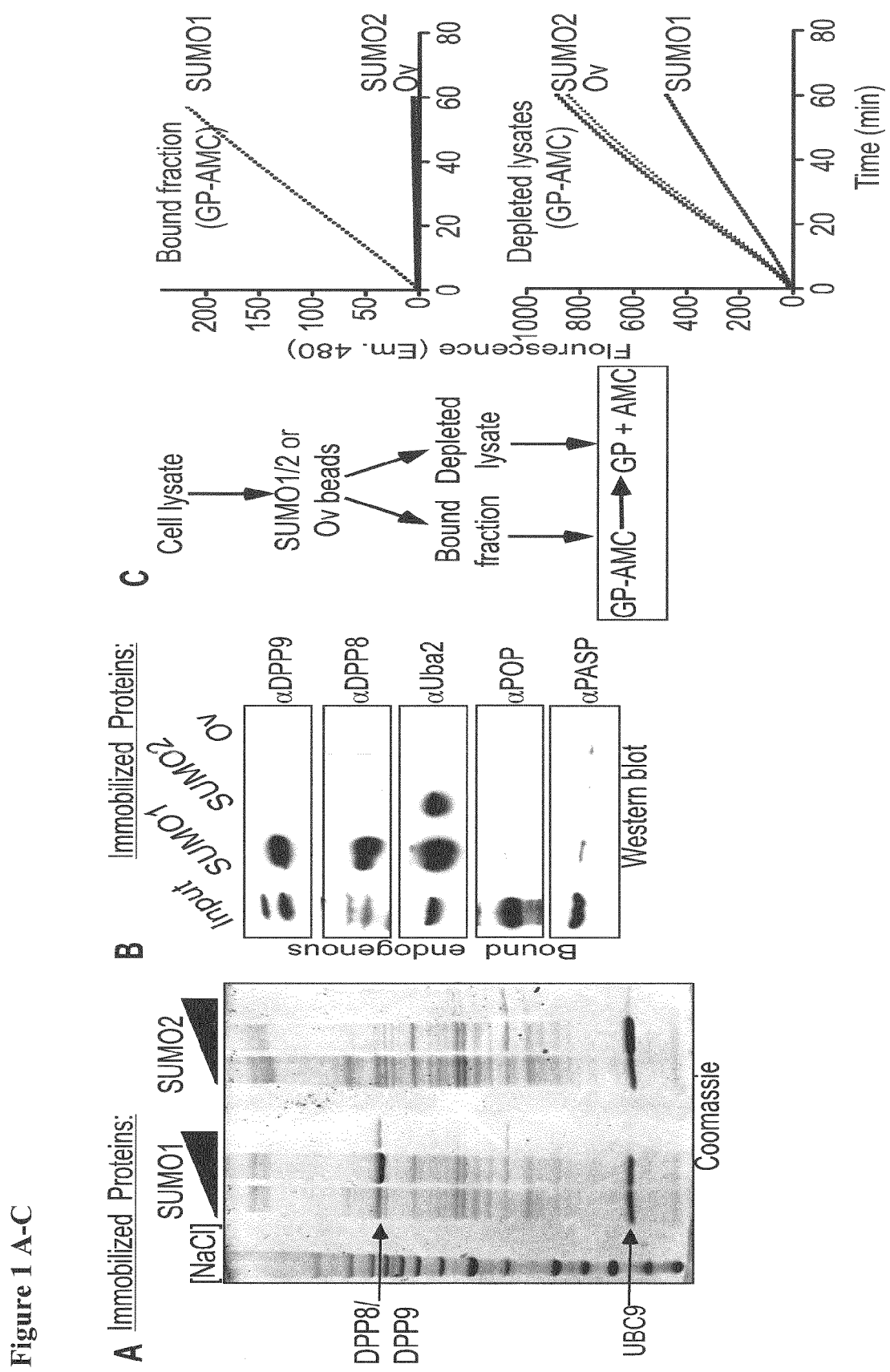

Figure 1 D-F
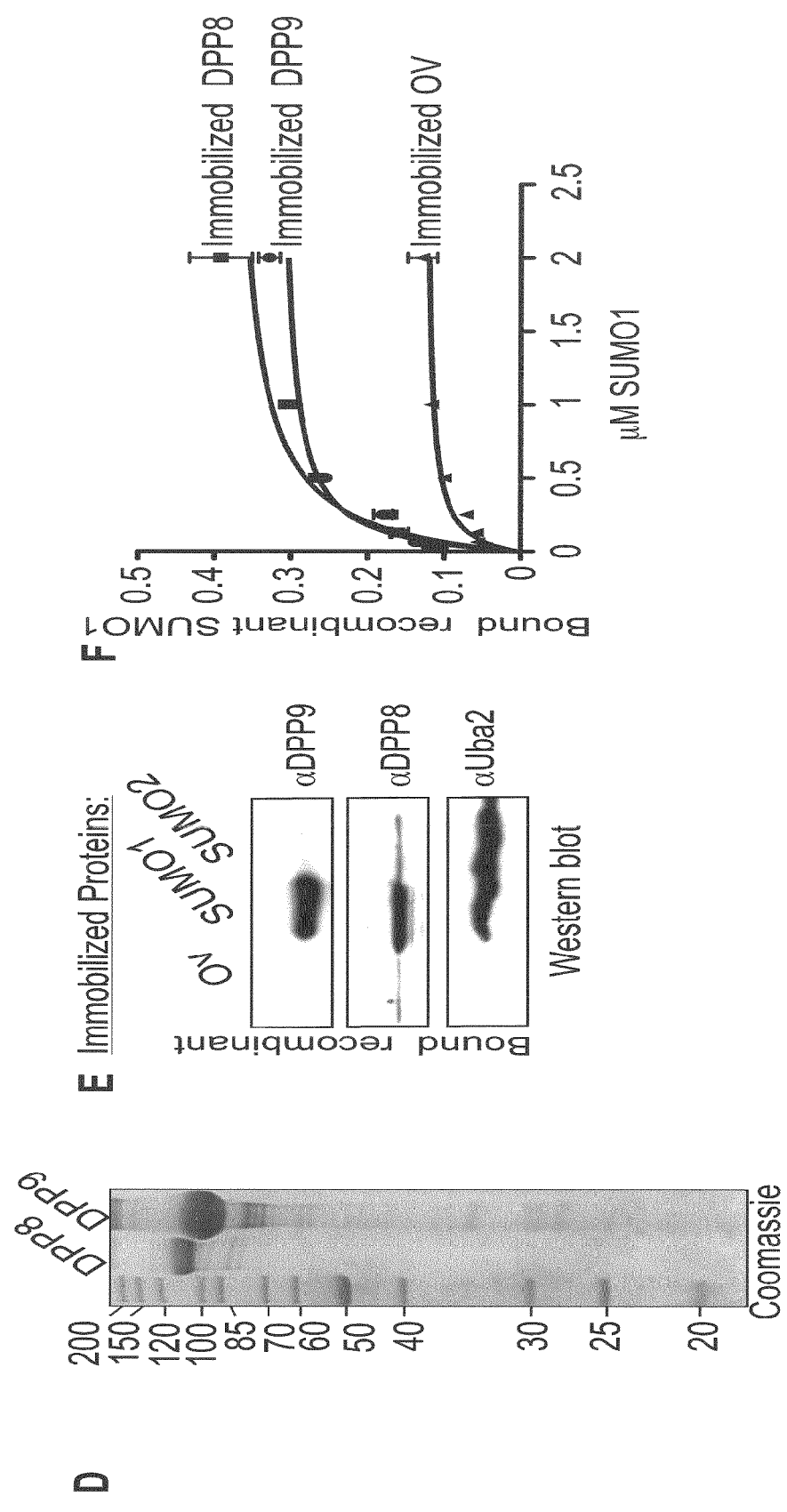

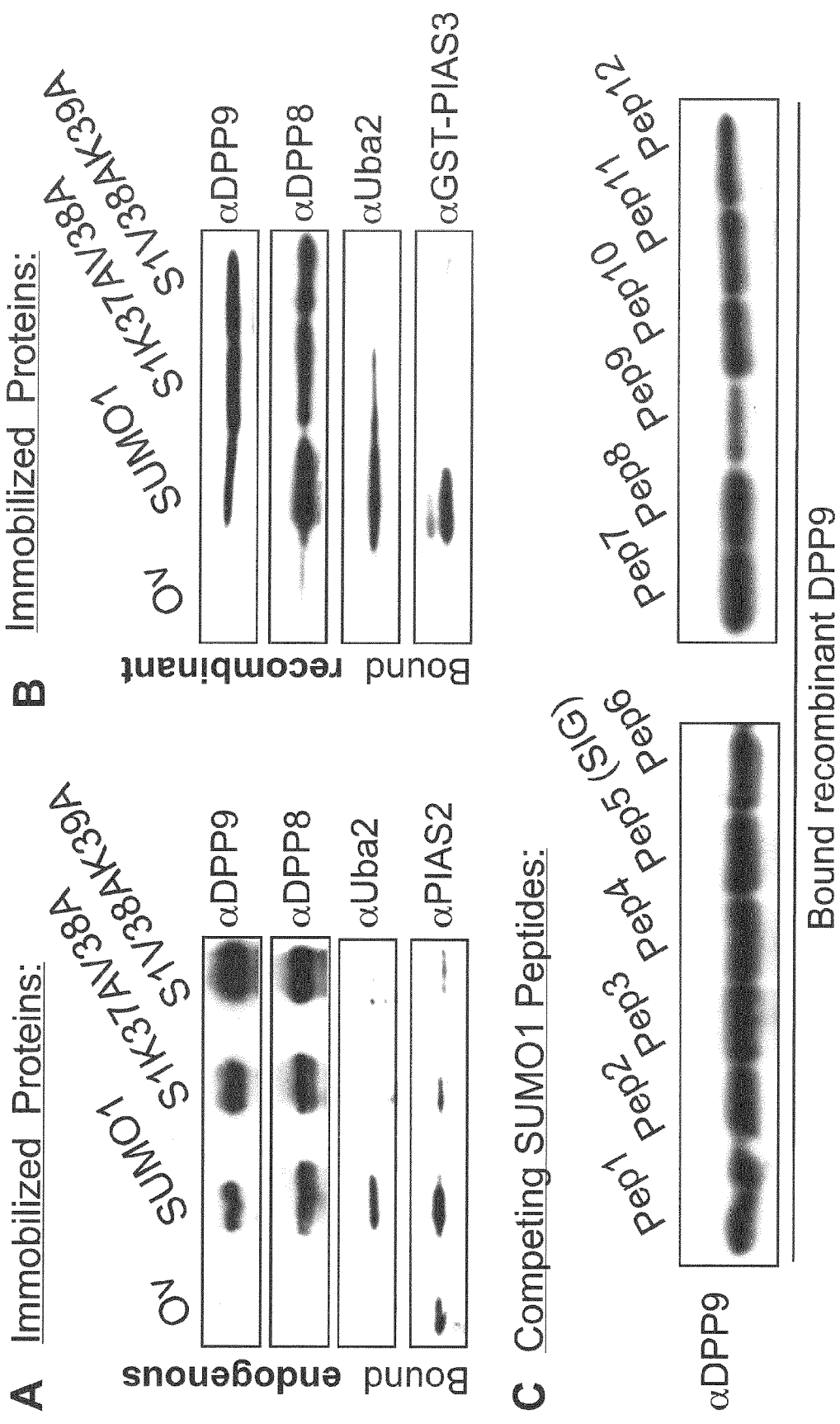
Figure 2 A-C

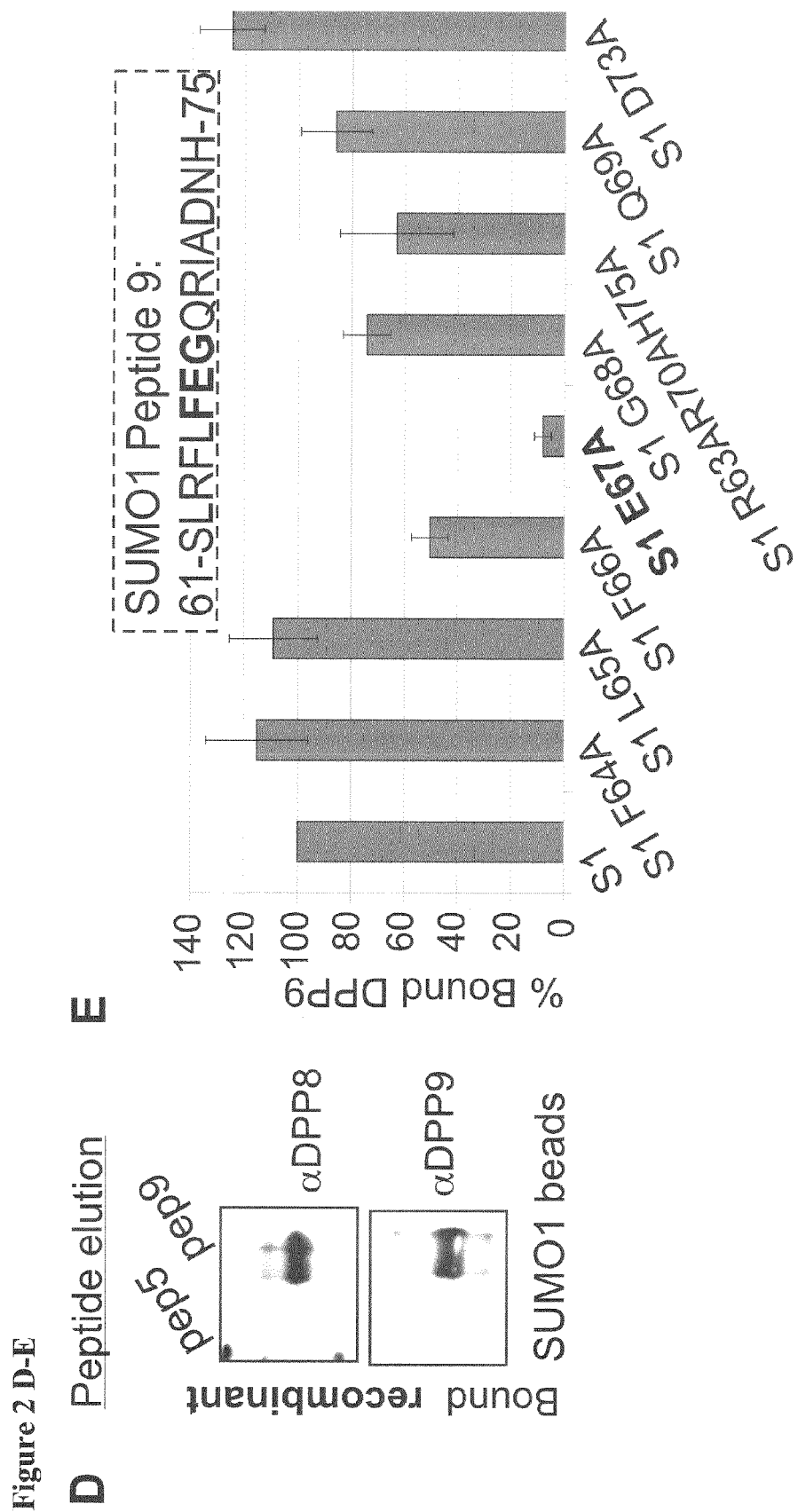
Figure 2 D-E

Figure 2 F-G
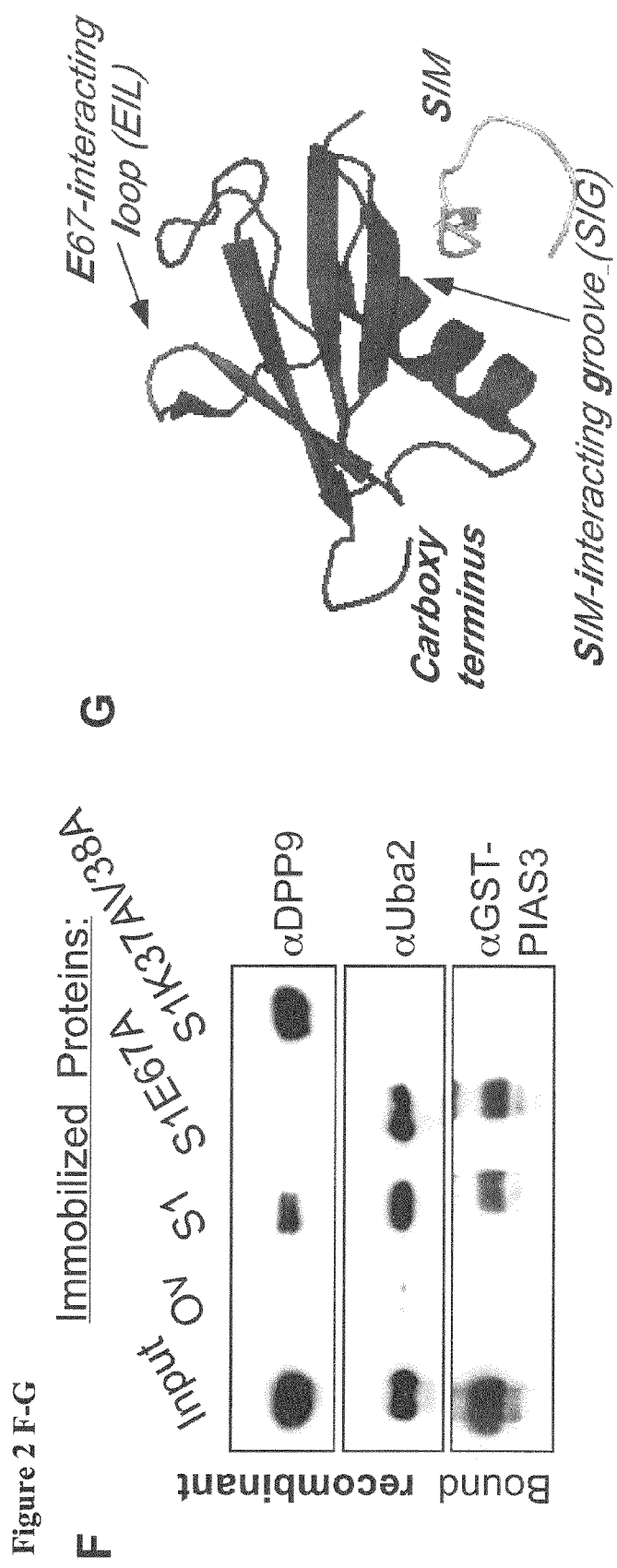
Figure 3
A  SUMO1  61  SLRFLFEGQRIADNH
   SUMO2  57  QIRFRFDGQPINETD
   SUMO3  56  QIRFRFDGQPINETD
                *    *      **

Figure 6 A-F

Figure 6 G-H
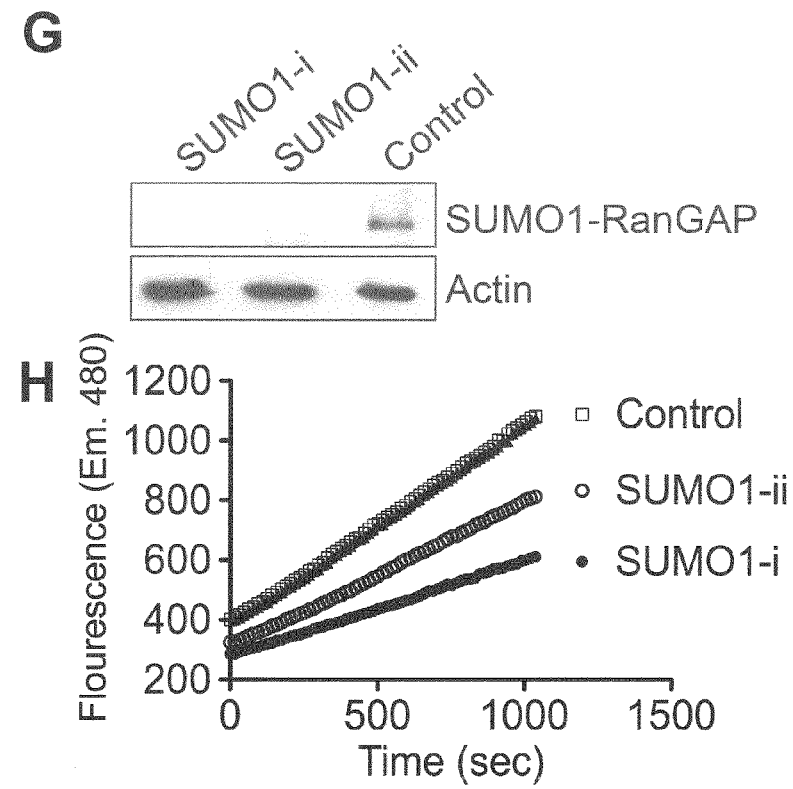
Figure 7
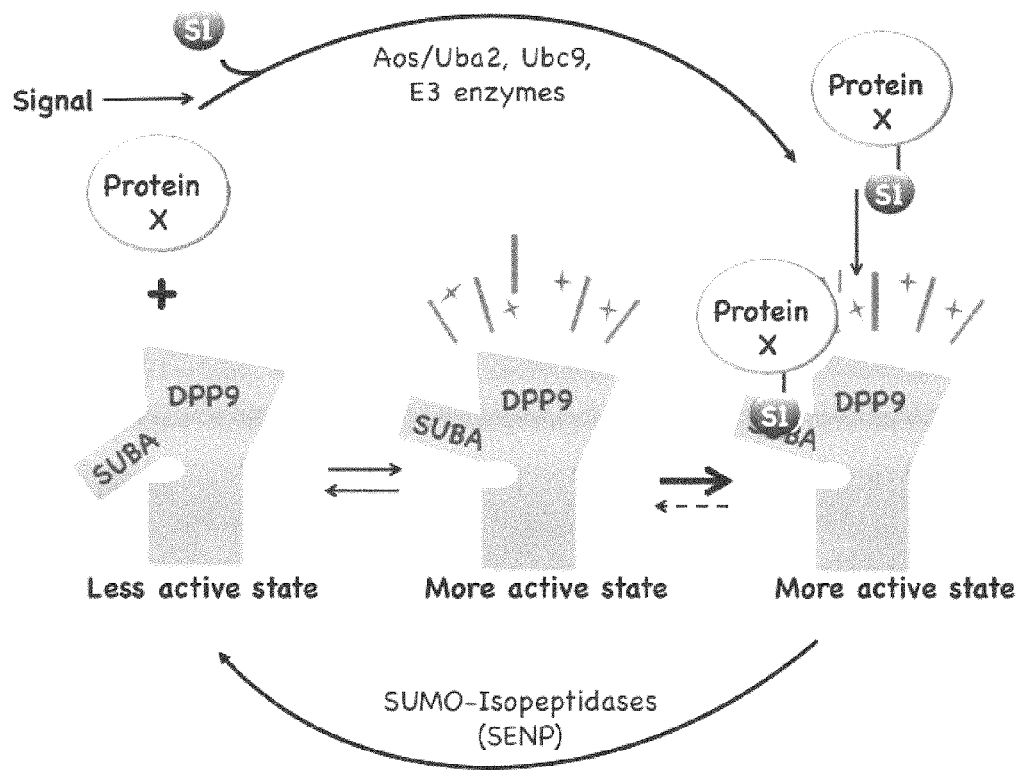

Figure 10

```
sp|Q86TI2-2|DPP9_HUMAN      -MRKVKKLRLDKENTGSWRSFSLNSEGAERMATTGTPTADRGDAAATDDP   49
sp|Q6V1X1|DPP8_HUMAN        MWKRSEQMKIKSGKCNMAAAMETEQLGVEIFETADCEENIESQDRPKLEP   50
sp|P27487|DPP4_HUMAN        -------------------------------------------------- sp|Q86TI2-2|DPP9_HUMAN      AARFQVQKHSWDGLRSIIHGSRKYSGLIVNKAPHDFQFVQKTDESGPHSH   99
sp|Q6V1X1|DPP8_HUMAN        ---FYVERYSWSQLKKLLADTRKKYHGYMMAKAPHDFMFVKRNDPDGPHSD   97
sp|P27487|DPP4_HUMAN        -----MKTPWKVLLGLLG----AAALVTIITVPVVLLNKGTDDATADSR   40
                                    .*. *                       .* sp|Q86TI2-2|DPP9_HUMAN      RLYYLGMPYGSRENSLLYSEIPKKVRKEALLLLSWKQMLDHFQATPHHGV  149
sp|Q6V1X1|DPP8_HUMAN        RIYYLAMSGENRENTLFYSEIPKTINRAAVLMLSWKPLLDLFQATLDYGM  147
sp|P27487|DPP4_HUMAN        -----SLRWISDHEYLYKQENNILVFNAEYGN   85
                             .*   *                                .:* sp|Q86TI2-2|DPP9_HUMAN      YSREEELLRERKRLGVFGITSYDFHSES-GLFLFQASNSLFHCRDGGKNG  198
sp|Q6V1X1|DPP8_HUMAN        YSREEELLRERKRIGTVGLASYDYHQGS-GTFLFQAGSGIYHVKDGGPQG  196
sp|P27487|DPP4_HUMAN        SS----VFLENSTFDEFGHSINDYSISPDGQFILLEYNYVKQWRHSYTAS  131
                             *       .*     . .   **  :   * ..            :

sp|Q86TI2-2|DPP9_HUMAN      FMVSPMKPLEIKTQCSGPRMDPKICPADP-AFFSFINNSDLWVANIETGE  247
sp|Q6V1X1|DPP8_HUMAN        FTQQPLRPNLVETSCPNIRMDPKLCPADP-DWIAFIHSNDIWISNIVTRE  245
sp|P27487|DPP4_HUMAN        YDIYDLNKRQLITEERIPNNTQWVTWSPVGHKLAYVWNNDIYVKIEPNLP  181
                              .  :  .   *         *.        :.   :::.

sp|Q86TI2-2|DPP9_HUMAN      ERRLTFCHQGLSNVLDDPKSAGVATFVIQEE-FDRFTGYWWCPTASWEGS  296
sp|Q6V1X1|DPP8_HUMAN        ERRLTYVHNELANMEEDARSAGVATFVLQEE-FDRYSGYWWCPKAETTPS  294
sp|P27487|DPP4_HUMAN        SYRITWTGK------EDIIYNGITDWVYEEEVFSAYSALWWSPNGTFLAY  225
                             *:*:    .         :*        *    :   **.. ..
```

Figure 10 continued

```
sp|Q86TI2-2|DPP9_HUMAN    EGLKTLRILVEEVDESEVEVTHVPSPALEERKTDSYRYPRTGSKNPKIAL  346
sp|Q6V1X1|DPP8_HUMAN      -GGKILRILVEENDESEVEIIHVTSPMLETRRADSFRYPKTGTANPKVTF  343
sp|P27487|DPP4_HUMAN      ----AQFNDTEVPLIEYSFYSDESLQYPKTVRVPYPKAGAVNP--TV     266
                              *:  .:  :.*:.*:.: *  **  :

sp|Q86TI2-2|DPP9_HUMAN    KLAEFQTDSQGKIVSTQEKELVQPFSSLFPKVEYIARAGWTRDGKYAWAM  396
sp|Q6V1X1|DPP8_HUMAN      KMSEIMIDAEGRIIDVIDKELIQPFEILFEGVEYIARAGWTPEGKYAWSI  393
sp|P27487|DPP4_HUMAN      KFFVVNTDSLSSVTNATSIQITAPASMLIG-DHYLCDVTWATQER----  310
                          *     .  . :   .  ::   :.* *    * sp|Q86TI2-2|DPP9_HUMAN    FLDRPQQWLQLVLLPPALFIPSTENEEQRLASARAVPRNVQPYVVYEEVT  446
sp|Q6V1X1|DPP8_HUMAN      LLDRSQTRLQIVLISPELFIPVEDDVMERQRLIESVPDSVTPLIYEETT  443
sp|P27487|DPP4_HUMAN      ---ISLQWLRRIQNYSVMDICDYDESSGRWNCLVARQH-----IEMST   350
                             *:  :   :        . *                     *  * sp|Q86TI2-2|DPP9_HUMAN    NVWINVHDIFYPFPQSEGEDELCFLRANECKTGFCHLYKVTAVLKSQGYD  496
sp|Q6V1X1|DPP8_HUMAN      DIWINIHDIFHVFPQS-HEEEIEFIFASECKTGFRHLYKITSILKESKYK  492
sp|P27487|DPP4_HUMAN      TGWVGR---FRPSEPHFTLDGNSFYKIISNEEGYRHIC------------  385
                            *:      * .    .      *  .   * .   :

sp|Q86TI2-2|DPP9_HUMAN    WSEPFFSPGEDEFKCPIKEEIALTSGEWEVLARHGSKIWNEETKLVYFQG  546
sp|Q6V1X1|DPP8_HUMAN      RSSGGLPAPSDFKCPIKEEIAITSGEWEVLGRHGSNIQVDEVRRLVYFEG  542
sp|P27487|DPP4_HUMAN      ------------YFQIDKKDCTFITKGTWEVIG-----IEALTSDYLYYISN  420
                                       *: ..:*.* ***** .     :*. :

sp|Q86TI2-2|DPP9_HUMAN    TKD-TPLEHHLYVVSYEAAGEIVRLTTPGFSHSCSMS-QNFDMFVSHYSS  594
sp|Q6V1X1|DPP8_HUMAN      TKD-SPLEHHLYVVSYVNPGEVTRLTDRGYSHSCCIS-QHCDFFISKYSN  590
sp|P27487|DPP4_HUMAN      EYKGMPGGRNLYKIQLSDYTKVTCLSCELNPERCQYYSVSFSKEAKYYQL  470
                            ::***  **  :  :** ***                  .
```

Figure 10 continued

```
sp|Q86TI2-2|DPP9_HUMAN      VSTPPCVHVYKLSGPDDDPLHKQPRFWASMMEAASCPPDYVPPEIFHFHT 644
sp|Q6V1X1|DPP8_HUMAN        QKNPHCVSLYKLSSPEDDPTCKTKEFWATILDSAGPLPDYTPPEIFSFES 640
sp|P27487|DPP4_HUMAN        RCSGPGLPLYTLHSSVNDKGLRVLEDNSALDKMLQN--VQMPSKKLDFII 518
                              :: .: .  .*                            * sp|Q86TI2-2|DPP9_HUMAN      RSDVRLYGMIYKPHALQPGKKHPTVLFVYGGPQVQLVNNSFKGIKYLRLN 694
sp|Q6V1X1|DPP8_HUMAN        TTGFTLYGMLYKPHDLQPGKKYPTVLFIYGGPQVQLVNNRFKGVKYFRLN 690
sp|P27487|DPP4_HUMAN        LNETKFWYQMILPPHFDKSKKYPLLLDVYAGPCSQKADTVFR--LNWATY 566
                              . *   *:   :*::::::**:  .*  :*.*    *       .

sp|Q86TI2-2|DPP9_HUMAN      TLASLGYAVVIDGRGSCQRGLRFEGALKNQMGQVEIEDQVEGLQFVAEK 744
sp|Q6V1X1|DPP8_HUMAN        TLASLGYVVVIDNRGSCHRGLKFEGAFKYKMGQIEIDDQVEGLQYLASR 740
sp|P27487|DPP4_HUMAN        LASTENIIVASFDGRGSGYQGDKIMHAINRRLGTFEVEDQIEAARQFS-K 615
                              *:.   ::   .**:       :.      *:. : :* :*.: :

sp|Q86TI2-2|DPP9_HUMAN      YGFIDLSRVAIHGWSYGGFLSLMGLIIHKPQVFKVAIAGAPVTVMAYDTG 794
sp|Q6V1X1|DPP8_HUMAN        YDFIDLDRVGIHGWSYGGYLSLMGLISLMALMQRSDIFRVAIAGAPVTLWIFYDTG 790
sp|P27487|DPP4_HUMAN        MGFVDNKRIAIWGWSYGGYVTSMVLGSGSGVFKCGIAVAPVSRWEYYDSV 665
                              . ::  * *:.*****:::  ::. *      .:..** ****.  *:

sp|Q86TI2-2|DPP9_HUMAN      YTERYMDVPENNQHGYEAGSVALHVEKLPNEPNRLLLIHGFLDENVHFFH 844
sp|Q6V1X1|DPP8_HUMAN        YTERYMGHPDQNEQGYYLGSVAMQAEKFPSEPNRLLLLHGFLDENVHFAH 840
sp|P27487|DPP4_HUMAN        YTERYMGLPTPEDNLDHYRNSTVMSRAENFKQVEYLLIHGTADDNVHFQQ 715
                            ******.  *   :  .       .   *:*::*** ::***..

sp|Q86TI2-2|DPP9_HUMAN      TNFLVSQLIRAGKPYQLQIYPNERHSIRCPESGEHYEVTLLHFLQEYL-- 892
sp|Q6V1X1|DPP8_HUMAN        TSILLSFLVRAGKPYDLQIYPQERHSIRVPESGEHYELHLLHYLQENLGS 890
sp|P27487|DPP4_HUMAN        SAQISKALVDVGVDFQAMWYTDEDHGIASSTAHQHIYTHMSHFIKQCFSL 765
                              :   : . . :      :   :.     * . *        :
```

```
sp|Q86TI2-2|DPP9_HUMAN      --------
sp|Q6V1X1|DPP8_HUMAN        RIAALKVI 898
sp|P27487|DPP4_HUMAN        P------- 766
```

DPP8 AND DPP9 PEPTIDE INHIBITORS

The present invention relates to non-competitive, allosteric inhibitors that target an arm motif of Dipeptidyl peptidase 8 (DPP8) and Dipeptidyl peptidase 9 (DPP9).

BACKGROUND OF THE INVENTION

Peptidases (proteolytic enzymes) constitute 1%-5% of eukaryotic genes, and are essential for many biological processes. Peptidases of the S9B/DPPIV family are unique in their ability to cleave off N-terminal dipeptides from substrates that have a proline residue at the second position (XaaPro). Four active members of this family are known, two of which are cell surface peptidases: Dipeptidyl peptidase IV (DPPIV) and the Fibroblast activation protein alpha (FAP).

The two cytosolic members of the DPPIV family are DPP8 and DPP9, which are expressed in multiple tissues, predominantly in lymphocytes and epithelial cells of many organs (Yu et al., 2009; Tang et al., 2009; Schade et al., 2008). DPP8 and DPP9 share overall 27% and 38% amino-acid identity (respectively) with DPPIV. Moreover, DPP8 and DPP9 are highly homologues (57% identical) sharing over 90% amino acid identity within their active sites (Van Goethem et al., 2011; Abbott et al., 2000; Ajami et al., 2004). In vitro, DPP8 and DPP9 are similar in their biochemical properties, including enzyme kinetics and substrate specificity (Geiss-Friedlander et al., 2009).

The physiological roles of DPP8 and DPP9 are only emerging. Down-regulation of both peptidases in several cell lines using siRNA treatment, shows that DPP9 but not DPP8, is rate-limiting for degradation of most cytosolic proline containing peptides (Geiss-Friedlander et al., 2009). Changes in the expression levels of DPP8 and DPP9 are critical for survival and proliferation of different cell lines, such as human hepatoma and embryonic kidney cells as well as cells originating from the Ewing sarcoma family of tumors (Yao et al., 2011; Lu et al., 2011). Over-expression of both peptidases was reported to impair cell adhesion and migration (Yu et al., 2006).

DPP8 and DPP9 have been shown to influence cell behavior such as cell-extracellular matrix interactions, proliferation and apoptosis. DPP9 transcription is abundant in human tumor cell lines such as melanoma, chronic myelogenous leukemia, colorectal adenocarcinoma, neuroblastoma, and HeLa cells (a cell line derived from cervical cancer), and is upregulated in human testicular tumors, as well as breast cancer cell lines, in particular estrogen negative breast cancer cell lines. DPP8 transcription as compared to transcription of other DPPs is significantly increased in breast cancer and ovarian cancer cell lines. Constitutive expression of DPP8 and DPP9 was also found in B cell chronic lymphocytic leukemia. The expression of DPP8 and DPP9 in tumor tissues and cell lines indicates that they may have roles in tumor pathogenesis (reviewed in Zhang et al., 2013). Inhibition of DPP8 and DPP9 by enzyme inhibition or siRNA breakdown have been shown to enhance cell death and tumor regression.

All inhibitors described so far for the DPP family, are competitive inhibitors that target the active site of the peptidase, which is highly conserved, making it difficult to target one specific member of the family.

Inhibitors for DPP IV are described in WO 2011/113895, US 2011/0218142 and US 2008/0293618. WO 2005/106487 describes antibodies and siRNA for modulating DPP9 activity.

SUMOs are small proteins that act as post-translational protein modifiers. Modification of proteins by SUMO (sumoylation) affects many cellular pathways including cell cycle progression, chromatin structure, DNA repair, transcription and trafficking. Humans express three functional SUMO homologs: SUMO1-3, which are conjugated to their targets in a reversible manner. SUMO2 and SUMO3 are highly homologous (97% identity) but share only 50% identity with SUMO1. The three homologs appear to serve overlapping but also distinct functions, since some proteins are modified preferably by one of the SUMO homolog (Geiss-Friedlander & Melchior, 2007).

Sumoylation can lead to various outcomes including changes in the localization, activity, solubility, or even stability of respective target proteins. These are due to changes in the molecular interactions of the modified proteins. Consequently, novel interactions depend on the presence of downstream effector proteins that contain motifs for non-covalent binding to SUMO. A single SUMO-interacting motif, SIM, is currently known which is characterized by a cluster of hydrophobic residues (Song et al., 2004; Hannich et al., 2005; Hecker et al., 2006). NMR and crystal structures reveal that SIMs bind to a SIM-interacting groove (SIG) formed between the α-helix and β-sheet of all three SUMO homologs (Song et al., 2004; Hannich et al., 2005; Hecker et al., 2006; Baba et al., 2005; Reverter & Lima, 2005). How SUMO-interacting proteins differentiate between the SUMO homologs is only partially understood. In some cases negative charges flanking the SIM, lead to a preferable interaction of the SIMs with SUMO1 over SUMO2/3 (Hecker et al., 2006; Chang et al., 2011).

SUMMARY OF THE INVENTION

All available inhibitors for DPP8 and DPP9, target the catalytic site of these enzymes, acting as competitive inhibitors. Importantly, the active site of all members of the DPPIV family is highly conserved. Specifically, DPP8 and DPP9 share over 90% amino acid identity in the catalytic pocket, therefore, the available inhibitors inhibit both peptidases (DPP8/9 inhibitors), raising the question whether the design of DPP8 or DPP9-specific inhibitors is an attainable goal. In addition, all available inhibitors show residual activity against other DPPIV homologs.

Accordingly, there is still a need in the art for inhibitors that can differentiate between members of the DDPIV family, and preferably between DPP8 and DPP9.

For more specific inhibition, instead of the catalytic site, the inventors are the first to propose to use inhibitory compounds that target allosteric binding sites in members of the DPPIV family.

Here, the inventors screened for proteins showing preferable interaction with either SUMO1 or with SUMO2. In this screen, the inventors identified two prolyl peptidases of the S9B/DPPIV family, Dipeptidyl peptidase 8 (DPP8) and Dipeptidyl peptidase 9 (DPP9) as specific interactors of SUMO1. More specifically, the inventors show that DPP9 and SUMO1 interact in a SIM-independent manner, and define a novel surface on SUMO1 for non-covalent interactions with down-stream effectors. Moreover, the inventors show that SUMO1 binds to an arm-motif in DPP9, which is located in proximity to the substrate entrance site. Importantly, the investigators show that the SUMO-binding arm is important for DPP9 activity.

Starting from this interaction site, the inventors developed a novel approach for allosteric non-competitive inhibition of DPP8 and DPP9, using small peptide inhibitors. The peptides described here act by targeting an arm-motif in both DPP8 and DPP9, which is a site for allosteric regulation of both peptidases by SUMO1. The arm-motif is less conserved between the members of the DPPIV enzymes. Importantly, DPP8 and DPP9 share only 70% identity in the arm-motif (compared to over 90% in the active site), raising the possibility that inhibitors can be developed, which would be selective for DPP8 or DPP9. Indeed one peptide variant: SLRFLYEG (SEQ ID NO: 38) shows preferential selectivity towards DPP9 (Ki 0.4 µM) over DPP8 (Ki 3.6 µM). This inhibition is selective for DPP8 and DPP9, and does not target their close homolog DPPIV. Furthermore, in contrast to competitive inhibitors, increased substrate concentration within the cell (i.e. due to enzyme inhibition) will not relieve the effect of the non-competitive inhibitors of the invention. Likewise, the corresponding interaction site on DPP8 and DPP9 may be used as to inhibit association of SUMO1 with downstream effectors. Alternatively it may be used as a target for developing other types of inhibitors of DPP8 and/or DPP9 activity, such as small molecules.

Accordingly, in a first aspect the invention provides a peptide of 8 to 20 amino acids length, comprising the N-terminal sequence $Xaa_1$-Leu-Arg-Phe-Leu-$Xaa_6$-$Xaa_7$-$Xaa_8$, wherein $Xaa_1$ is Ser or Thr, wherein $Xaa_6$ is Phe, Tyr, Trp, Val or Ile, wherein $Xaa_7$ is Ala or Glu, and wherein $Xaa_8$ is Gly or Ala (SEQ ID NO: 48); wherein the peptide is a non-competitive allosteric inhibitor of DPP9 and/or DPP8.

The peptide may have a $K_i$ for DPP9 of 0.4-10 µM, and/or a $K_i$ for DPP8 of 3.6 to 12 µM. The peptide is preferably capable of inhibiting the activity by wild-type DPP9 (SEQ ID NO: 6) to a level of 35 to 5% of the activity if not inhibited, as determined in an assay using 25 nM DPP9, 0.2 mM GP-AMC, and 14 µM of the peptide to be tested, in in TB buffer (20 mM Hepes/KOH pH 7.3, 110 mM potassium acetate, 2 mM Mg acetate, 0.5 mM EGTA), supplemented with 0.2% Tween-20, 1 mM dithiothreitol, 380 nm excitation and 480 nm emission.

At the same time, the peptide may have no inhibitory effect towards DPPIV, as determined in an assay using 25 nM DPPIV, 0.2 mM GP-AMC, and 14 µM of the peptide to be tested, in in TB buffer (20 mM Hepes/KOH pH 7.3, 110 mM potassium acetate, 2 mM Mg acetate, 0.5 mM EGTA), supplemented with 0.2% Tween-20, 1 mM dithiothreitol, 380 nm excitation and 480 nm emission.

The peptide may further comprise or be fused to a stretch of one, two or three Ala-residues followed by 5-9 Arg-residues for improving cell penetration of the peptide. Alternatively, the peptide may also comprise said Arg-residues without the Ala-linker. Particularly preferred peptides are shown in SEQ ID NO: 14, 38, 15, 39, 40, 30, 28, 22, 45, 37, 29, 18, 1, 19, 27, or 41. The peptide may be fused to the N-terminus of a polypeptide. In a second aspect, the invention provides another peptide having the sequence Val-Glu-$Xaa_3$-Ile-His-Val-$Xaa_7$-Ser-Pro-$Xaa_{10}$-Leu-Glu-$Xaa_{13}$-Arg-$Xaa_{15}$-$Xaa_{16}$-Asp-Ser-$Xaa_{19}$-Arg, wherein $Xaa_3$ is any amino acid, wherein $Xaa_7$ is Pro or Thr, wherein $Xaa_{10}$ is Ala or Met, wherein $Xaa_{13}$ is Glu or Thr, wherein $Xaa_{15}$ is Lys or Arg, wherein $Xaa_{16}$ is Thr or Ala, and wherein $Xaa_{19}$ is Tyr or Phe (SEQ ID NO: 49). Preferably, said peptide has the amino acid sequence of SEQ ID NO: 11. This second peptide may also be comprised in a polypeptide, but with the provisio that the peptide is not DPP8 or DPP9.

In further aspects, the invention provides a host cell expressing one of the peptides or polypeptides as defined above, a method for producing the peptide or polypeptide as defined above, an isolated nucleic acid molecule, encoding the peptide or the polypeptide as defined above, an expression vector, comprising said nucleic acid molecule. Further provided is a kit comprising a peptide as described above, and/or a polypeptide as described above, and/or a host cell as described above, and/or an isolated nucleic acid molecule as described above, and/or the expression vector a described above; and optionally a carrier peptide, preferably a carrier peptide having the amino acid sequence of SEQ ID NO: 47. The peptide or polypeptide according to the first aspect may be used in a non-therapeutic method of selectively inhibiting DPP9 and/or DPP8, preferably in combination with a carrier peptide, more preferably a carrier peptide having the amino acid sequence of SEQ ID NO: 47. Alternatively, one may also use the isolated nucleic acid molecule or the expression vector encoding the peptide or polypeptide according to the first aspect in a non-therapeutic method of selectively inhibiting DPP9 and/or DPP8.

Similarly, one may use the peptide or polypeptide of the second aspect in a non-therapeutic method of competitively inhibiting binding to the E67-interacting loop (EIL) of SUMO-1, preferably in combination with a carrier peptide, more preferably a carrier peptide having the amino acid sequence of SEQ ID NO: 47. Alternatively, one may also use the isolated nucleic acid molecule or the expression vector encoding the peptide or polypeptide according to the second aspect in a non-therapeutic method of competitively inhibiting binding to the E67-interacting loop (EIL) of SUMO-1.

Moreover, the arm motif shown in the amino acid sequence motif of SEQ ID NO: 12, or SEQ ID NO: 13, or SEQ ID NO: 11, within DPP9 and/or DPP8, as identified herein, may be used for screening and/or selecting a non-competitive allosteric inhibitor of DPP9 and/or DPP8.

This may be done, for example in an in silico method for characterization of a candidate compound as a non-competitive allosteric inhibitor of DPP9 and/or DPP8, which method comprises the steps of: (a) providing a candidate compound for the characterization, (b) fitting said candidate compound with an amino acid sequence motif of SEQ ID NO: 12, or SEQ ID NO: 13, or SEQ ID NO: 11, within DPP9 and/or DPP8 in silico, and (c) determining whether said candidate compound is expected to bind to said arm motif; and (d) optionally determining whether said candidate compound decreases the enzymatic activity of DPP9 and/or DPP8 in vitro.

This may be done, for example, in an in vitro method for characterization of a candidate compound as a non-competitive allosteric inhibitor of DPP9 and/or DPP8. The method could comprise the steps of: (a) providing a candidate compound for the characterization, which is expected to bind to an amino acid sequence motif of SEQ ID NO: 12, or SEQ ID NO: 13, or SEQ ID NO: 11, within DPP9 and/or DPP8, and (b) determining whether said candidate compound decreases the enzymatic activity of DPP9 and/or DPP8 in vitro in a non-competitive allosteric manner.

DETAILED DESCRIPTION OF THE PREFERRED EMBODIMENTS

Provided is a peptide of 8 to 20 amino acids length, comprising the N-terminal sequence $Xaa_1$-Leu-Arg-Phe-Leu-$Xaa_6$-$Xaa_7$-$Xaa_8$, wherein $Xaa_1$ is Ser or Thr, wherein $Xaa_6$ is Phe, Tyr, Trp, Val or Ile, wherein $Xaa_7$ is Ala or Glu, and wherein $Xaa_8$ is Gly or Ala (SEQ ID NO: 48); wherein the peptide is a non-competitive allosteric inhibitor of DPP9 and/or DPP8.

The inhibitor is primarily intended as an inhibitor of human DPP8 and/or DPP9, but may also show cross-reactivity with homologous DPP8 and/or DPP9 of other origin such as from mouse, rat, pig, or primates. Human DPP8 and DPP9 are well known to the skilled person. The amino acid sequence of human DPP9 is shown in SEQ ID NO: 6, whereas the amino acid sequence of human DPP8 is shown in SEQ ID NO: 8. However, the terms "DPP8" and "DPP9" as used herein are also intended to refer to any naturally occurring alternatively spliced variant and isoform of human DPP8 and DPP9, respectively. Such splice variants and isoforms can be obtained from, e.g. publicly accessible protein databases, such as from NCBI, SWISSPROT or EMBL.

Non-competitive allosteric inhibition results from a change in the shape of the active site when the peptide binds to the allosteric site in DPP8 and/or DPP9. As a result of said change in the shape, the active site-substrate interaction is affected, i.e. the enzymatic activity of DPP8 and/or DPP9 is decreased. Since the allosteric inhibitor interacts with the allosteric site of DPP8 and/or DPP9, and not with the active site, it does not compete with the substrate for binding to the active site—it is non-competitive. The skilled person knows well the concept of non-competitive allosteric inhibition, and how to determine whether an inhibitor effects its function by competitive or non-competitive allosteric inhibition. For example, one may determine the enzyme kinetics in a Michaelis-Menten-Plot and a Lineweaver-Burk-Plot.

Such plots can be made by using an assay using 25 nM purified recombinant DPP9 (SEQ ID NO: 6) and DPP8 (SEQ ID NO: 7), respectively, varying amounts of the GP-AMC (0, 31, 62.5, 125, 250, 500 mM GP-AMC), and varying amounts of the peptide to be tested (inhibitor), in TB buffer (20 mM Hepes/KOH pH 7.3, 110 mM potassium acetate, 2 mM Mg acetate, 0.5 mM EGTA), supplemented with 0.2% Tween-20, 1 mM dithiothreitol. Release of AMC from GP-AMC is measured using the Appliskan microplate fluorimeter (Thermo Scientific) with 380 nm (excitation) and 480 nm (emission) filters and the Skanit software, and analysed using the Prism software.

In one preferred embodiment, the peptide has a length of 8 amino acids. In another preferred embodiment, the peptide has a length of 9 amino acids. In still another preferred embodiment, the peptide has a length of 10 amino acids. In another preferred embodiment, the peptide has a length of 11 amino acids. In one preferred embodiment, the peptide has a length of 12 amino acids. In still another preferred embodiment, the peptide has a length of 13 amino acids. In one specific preferred embodiment, the peptide has a length of 14 amino acids. In one particular preferred embodiment, the peptide has a length of 15 amino acids. In still further preferred embodiments, the peptide has a length of 16, 17, 18, 19 or 20 amino acids.

Preferably, the peptide may have a $K_i$ for DPP9 (SEQ ID NO: 6) of 0.4-10 µM, and/or a $K_i$ for DPP8 (SEQ ID NO: 7) of 3.6 to 12 µM. For example, the peptide may have a $K_i$ for DPP9 of 0.4-9 µM, 0.4-8 µM, 0.4-7 µM, 0.4-6 µM, 0.4-5 µM, 0.4-4 µM, 0.4-3 µM, 0.4-2.5 µM, 0.4-2 µM, 0.4-1.5 µM, 0.4-1 µM, or 0.4-0.8 µM. In addition or alternatively, the peptide may have a $K_i$ for DPP8 of 3.6 to 11 µM, 3.6 to 10 µM, 3.6 to 9 µM, 3.6 to 8 µM, 3.6 to 7 µM, 3.6 to 6 µM, 3.6 to 5 µM, 3.6 to 4.5 µM, or 3.6 to 4 µM.

Enzyme kinetics and the $K_i$ of DPP8 or DPP9 may be determined as follows: 25 nM purified recombinant enzyme (DPP9 or DPP8) are incubated with varying concentrations of GP-AMC (0, 31, 62.5, 125, 250, 500 mM GP-AMC), in TB buffer (20 mM Hepes/KOH pH 7.3, 110 mM potassium acetate, 2 mM Mg acetate, 0.5 mM EGTA), supplemented with 0.2% Tween-20, 1 mM dithiothreitol. Experiments are performed in triplicates. To measure Ki values, for each set of experiments, inhibitory peptides are added to DPP9 or DPP8. Peptide concentrations tested are in the range between 0.04 to 50 µM. Release of AMC from GP-AMC is measured using the Appliskan microplate fluorimeter (Thermo Scientific) with 380 nm (excitation) and 480 nm (emission) filters and the Skanit software, and analysed using the Prism software.

Accordingly, the peptide is capable of inhibiting the activity of wild-type DPP9 (SEQ ID NO: 6) to a level of 35 to 5% of the activity of wild-type DPP9 (SEQ ID NO: 6) if not inhibited, as determined in an assay using 25 nM purified DPP9, 0.2 mM GP-AMC, and 14 µM of the peptide to be tested, in TB buffer (20 mM Hepes/KOH pH 7.3, 110 mM potassium acetate, 2 mM Mg acetate, 0.5 mM EGTA), supplemented with 0.2% Tween-20, 1 mM dithiothreitol. Release of AMC from GP-AMC is measured using the Appliskan microplate fluorimeter (Thermo Scientific) with 380 nm (excitation) and 480 nm (emission) filters and the Skanit software, and analysed using the Prism software.

Preferably, the peptide is capable of inhibiting the activity by wild-type DPP9 (SEQ ID NO: 6) to a level of 30 to 5%, 29 to 5%, 28 to 5%, 27 to 5%, 26 to 5%, 25 to 5%, 24 to 5%, 23 to 5%, 22 to 5%, 21 to 5%, 20 to 5%, 19 to 5%, 18 to 5%, 17 to 5%, 16 to 5%, 15 to 5%, 14 to 5%, 13 to 5%, 12 to 5%, 11 to 5%, 10 to 5%, 9 to 5%, 8 to 5%, such as 7.5 to 5% of the activity of wild-type DPP9 (SEQ ID NO: 6) if not inhibited. It is further preferred that the peptide has no inhibitory effect towards DPPIV (SEQ ID NO: 8) as determined in an assay using 25 nM DPPIV, 0.2 mM GP-AMC, and 14 µM, preferably 15 µM, such as 17.5 µM, more preferably 20 µM, such as 25 µM, even more preferably 30 µM, such as 35 µM, and most preferably 40 µM, such as 45 µM, or even 50 µM of the peptide to be tested, in TB buffer (20 mM Hepes/KOH pH 7.3, 110 mM potassium acetate, 2 mM Mg acetate, 0.5 mM EGTA), supplemented with 0.2% Tween-20, 1 mM dithiothreitol. Release of AMC from GP-AMC is measured using the Appliskan microplate fluorimeter (Thermo Scientific) with 380 nm (excitation) and 480 nm (emission) filters and the Skanit software, and analysed using the Prism software.

The following embodiments may be combined in any possible combination. In one preferred embodiment, $Xaa_1$ is Ser. In another preferred embodiment, $Xaa_1$ is Thr. $Xaa_6$ is preferably selected from Phe, Tyr, Trp, or Val, more preferably $Xaa_6$ is Phe, Tyr, or Trp, even more preferably $Xaa_6$ is selected from Phe or Tyr, and most preferably $Xaa_6$ is Phe. Accordingly, in one embodiment $Xaa_6$ is Phe. In another embodiment $Xaa_6$ is Tyr. In still another embodiment $Xaa_6$ is Trp. In a further embodiment $Xaa_6$ is Val. In another embodiment $Xaa_6$ is Ile. In one particular embodiment $Xaa_7$ is Ala. In another embodiment $Xaa_7$ is Glu. In still another embodiment $Xaa_8$ is Gly. In an alternative embodiment $Xaa_8$ is Ala. The peptide may have Gln at amino acid position 9, and/or Arg at position 10, and/or Ile at position 11, and/or Ala at position 12, and/or Asp at position 13, and/or Asn at position 14, and/or His at position 15. Hence, in one preferred embodiment, the peptide may have Gln at amino acid position 9. Such a peptide may have a length of 9 amino acids. In one embodiment the peptide may have Gln at amino acid position 9, and Arg at position 10. Such a peptide may have a length of 10 amino acids. In another preferred embodiment, the peptide may have Gln at amino acid position 9, Arg at position 10, and Ile at position 11. Such a peptide may have a length of 11 amino acids. In still another preferred embodiment, the peptide may have Gln at amino acid position 9, Arg at position 10, Ile at position 11, and Ala at position 12. Such a peptide may have a length of 12 amino acids. In another preferred embodiment, the peptide may have Gln at amino acid position 9, Arg at position 10, Ile at position 11, Ala at position 12, and Asp at position 13. Such a peptide may have a length of 13 amino acids. In still another preferred embodiment, the peptide may have Gln at amino acid position 9, Arg at position 10, Ile at position 11, Ala at position 12, Asp at position 13, and Asn at position 14. Such a peptide may have a length of 14 amino acids. In another preferred embodiment, the peptide may have Gln at amino acid position 9, Arg at position 10, Ile at position 11, Ala at position 12, Asp at position 13, Asn at position 14, and His at position 15. Such a peptide may have a length of 15 amino acids.

Alternatively, positions 9 to 20 may also comprise a stretch of one, two or three Ala-residues followed by 5-9 Arg residues for improving cell penetration of the peptide. On the other hand, positions 9 to 20 may also merely comprise 5-9 Arg-residues for improving cell penetration of the peptide, without the need for the Ala residues.

Whether the cell penetration is improved can be tested in a similar way as described in Example 8. Briefly, 10 µM of the peptide to be tested are in 250 ml DMEM without FCS, supplemented with glutamine and antibiotics. HEK293 cells (human embryonic kidney cells), grown in 24 well plates at 50% confluence are incubated with the peptide mix for 30 minutes at 37° C. Cells are then trypsinized and washed twice with PBS buffer to remove peptide excess. Cell pellet is shock frozen in liquid nitrogen. For preparation of cytosolic extracts: cell pellets are resuspended in TB buffer (20 mM Hepes/KOH pH 7.3, 110 mM potassium acetate, 2 mM Mg acetate, 0.5 mM EGTA), dounced and centrifuged at 14,000×g. Protein content of cytosolic extracts are measured using a Bradford assay, 5 µg cytosolic extracts are then tested for the hydrolysis of 500 µM GP-AMC. Fluorescence is measured using the Appliskan microplate fluorimeter (Thermo Scientific) with 380 nm (excitation) and 480 nm (emission) filters and the Skanit software, and analysed using the Prism software.

In a more preferred embodiment, the peptide has an amino acid sequence selected from the amino acid sequences shown in SEQ ID NO: 14, 38, 15, 39, 40, 30, 28, 22, 45, 37, 29, 18, 1, 19, 27, and 41.

Generally, the amino acid residue at position 1 of the peptide contains a free amino-terminus. However, the peptide may be fused at its C-terminus with another peptide or polypeptide, e.g. with a carrier peptide, allowing cell penetration of the resulting fusion peptide. Thus, a polypeptide is provided, which comprises at its N-terminus the peptide as defined above, i.e. the peptide as defined above fused to the N-terminus of said peptide or polypeptide. The resulting fusion-(poly)peptide may have a length of up to 30, 40, 50, 60, 70, 80, 90, 100, 125, 150, 175, 200, 150, 300, 350, 400, 450, 500, 600, 700, 800, 900, 1000, 1100, 1200, 1300, 1400 or even 1500 amino acids. However, the polypeptide maintains the inhibitory activity as defined above for the peptide.

For example, the peptide may be fused to a cell penetrating peptide (CPP). CPPs are short peptides that facilitate cellular uptake of various molecular cargo, e.g. via endocytosis. Thereby, CPPs are associated with the peptides either covalently through chemical linkage or non-covalently. The CPPs are typically composed of either a high relative abundance of positively charged amino acids (e.g., Lys or Arg; referred to as polycationic CPP) or contains an alternating pattern of polar/charged amino acids and non-polar/hydrophobic amino acids (referred to as amphipatic CPPs). One prominent member of CPPs is TAT. Accordingly, the polypeptide described herein may be a TAT-fusion peptide.

However, the peptide may also be fused to other peptides, such as peptidomimetics (beta peptides, D-peptides), carbamates and dendrimers, e.g. for improving cell penetration of the peptide.

In a second aspect, the invention provides a peptide having the sequence Val-Glu-$Xaa_3$-Ile-His-Val-$Xaa_7$-Ser-Pro-$Xaa_{10}$-Leu-Glu-$Xaa_{13}$-Arg-$Xaa_{15}$-$Xaa_{16}$-Asp-Ser-$Xaa_{19}$-Arg, wherein $Xaa_3$ is any amino acid, wherein $Xaa_7$ is Pro or Thr, wherein $Xaa_{10}$ is Ala or Met, wherein $Xaa_{13}$ is Glu or Thr, wherein $Xaa_{15}$ is Lys or Arg, wherein $Xaa_{16}$ is Thr or Ala, and wherein $Xaa_{19}$ is Tyr or Phe (SEQ ID NO: 49).

It has been shown in the examples that substitution of $Xaa_3$ has no significant effect on the binding to SUMO1. Nonetheless, in a preferred embodiment, $Xaa_3$ is Val, Ile or Ala, and more preferably $Xaa_3$ is Val or Ile. Accordingly, in one embodiment $Xaa_3$ is Val. In another embodiment, $Xaa_3$ is Ile. In still another embodiment, $Xaa_3$ is Ala. In an additional or in an alternative embodiment, $Xaa_7$ is Pro. In another embodiment, $Xaa_7$ is Thr. In another particular embodiment, $Xaa_{10}$ is Ala. In another specific embodiment, $Xaa_{10}$ is Met. In one embodiment, $Xaa_{13}$ is Glu. In another embodiment, $Xaa_{13}$ is Thr. In one embodiment, $Xaa_{15}$ is Lys. In one embodiment, $Xaa_{15}$ is Arg. In another embodiment, $Xaa_{16}$ is Thr. In still another embodiment, $Xaa_{16}$ is Ala. In one embodiment, $Xaa_{19}$ is Tyr. In another embodiment, $Xaa_{19}$ is Phe. Any of the above embodiments of the second aspect may be combined with each other. In a preferred embodiment, the peptide has the amino acid sequence of SEQ ID NO: 11.

The peptide of the second aspect may be comprised in a polypeptide, wherein the polypeptide is not DPP8 or DPP9. The polypeptide may have a length of up to 30, 40, 50, 60, 70, 80, 90, 100, 125, 150, 175, 200, 150, 300, 350, 400, 450, 500, 600, 700, 800, 900, 1000, 1100, 1200, 1300, 1400 or even 1500 amino acids. However, the polypeptide maintains the inhibitory activity as defined above for the peptide of the second aspect.

Also contemplated is a host cell expressing the peptides or the polypeptides of the invention. The host cell may be any cell suitable for expressing or producing the peptide or polypeptide as defined above in vitro. The host cell may be a bacterial cell, a fungal cell, such as a yeast cell or a filamentous fungal cell, an insect cell or a mammalian cell. However, the cell may not be a human embryonic stem cell, or other type of cell excluded from patentability by certain regional or national authorities. The skilled person will know suitable host cells and how to choose a particular host cell for the respective purpose. Further provided is a method of producing the peptides or the polypeptides according to the invention. The peptide or polypeptide may be produced synthetically, e.g. using a peptide synthesizer. Methods and devices for producing the peptides and polypeptides of the invention are well-known in the art. Alternatively, for example if the peptide or polypeptide is too big for synthetic production, the peptide or polypeptide may be produced by using a host cell, as defined above. Methods for cultivation will depend on the host cell of choice, but may comprise cell cultivation or fermentation in both small scale and large scale, using media and procedures well known in the art.

Also contemplated is an isolated nucleic acid molecule, which encodes the peptide(s) or the polypeptide(s) according to the invention. The nucleic acid molecule may be a RNA, DNA or an RNA/DNA chimera. Further contemplated is an expression vector, comprising the nucleic acid molecule as described above. The nucleic acid molecule or the expression vector may be used, e.g. for producing a host cell as described above, by using routine techniques well known in the art.

As mentioned above, the peptides and polypeptides of the invention may be used as a research tool. Accordingly, the peptide or polypeptide, the nucleic acid molecule, the expression vector and the host cell as described above may be provided in a kit. Consequently, also contemplated is a kit comprising (i) a peptide of the invention, and/or (ii) a polypeptide of the invention, and/or a host cell as defined above, and/or an isolated nucleic acid molecule as defined above, and/or the expression vector as described above. The kit may further comprise a carrier peptide or CPP, preferably a carrier peptide having the amino acid sequence of SEQ ID NO: 47, which may be useful in delivering the peptide over the cell membrane of a subject cell in a research experiment.

In this context, it will be apparent to the skilled person that the peptide or the polypeptide according to the first aspect may be used in a non-therapeutic method of selectively inhibiting DPP9 and/or DPP8, preferably in combination with a carrier peptide, more preferably a carrier peptide having the amino acid sequence of SEQ ID NO: 47. However, the peptide could also be produced in situ in the subject cell. Accordingly, it is also contemplated to use the isolated nucleic acid molecule or the expression vector encoding the peptide or polypeptide of the first aspect in a non-therapeutic method of selectively inhibiting DPP9 and/or DPP8.

The term "selectively inhibiting" as used herein is intended to mean that the peptide or polypeptide of the first aspect may inhibit DPP9 and/or DPP8, but not other proteases of the DPP family, in particular those proteases of the DPP family that lack the allosteric inhibition site, such as DPPIV.

Moreover, the peptide or the polypeptide of the second aspect may be used in a non-therapeutic method of competitively inhibiting binding to the E67-interacting loop (EIL) of SUMO-1. The peptide or polypeptide may also be used in combination with a carrier peptide, if deemed appropriate, e.g., with a carrier peptide having the amino acid sequence of SEQ ID NO: 47.

Alternatively, the isolated nucleic acid molecule or the expression vector encoding the peptide or polypeptide of the second aspect may be used in a non-therapeutic method of competitively inhibiting binding to the E67-interacting loop (EIL) of SUMO-1.

To the best knowledge of the inventors, the present disclosure is the first to report an allosteric site within DPP8 and DPP9, determined as the amino acid sequence motif of SEQ ID NO: 12, or SEQ ID NO: 13, or SEQ ID NO: 11. Besides the peptides of the first aspect, which may be used for inhibiting DPP8 and/or DPP9, having knowledge of the present invention will allow screening and developing further inhibitors of DPP8 and/or DPP9. Accordingly, the amino acid sequence motif of SEQ ID NO: 12, or SEQ ID NO: 13, or SEQ ID NO: 11, within DPP9 and/or DPP8, may be used for screening and/or selecting a non-competitive allosteric inhibitor of DPP9 and/or DPP8.

For example, an in silico method for characterization of a candidate compound as a non-competitive allosteric inhibitor of DPP9 and/or DPP8 is contemplated, which method comprises the steps of: (a) providing a candidate compound for the characterization, (b) fitting said candidate compound with an amino acid sequence motif of SEQ ID NO: 12, or SEQ ID NO: 13, or SEQ ID NO: 11, within DPP9 and/or DPP8 in silico, and (c) determining whether said candidate compound is expected to bind to said arm motif.

The sequence and structure of DPP9 and DPP8 is known in the art, and 3D-in silico models may be easily produced by using freely available computer programs, e.g. SWISS-MODEL, available from http://swissmodel.expasy.org/; or other modeling programs, such as from http://www.protein-modelportal.org/. Then, a candidate compound or molecule, e.g. a small molecule, a peptide or a peptidomimetic, can be fitted to the target site made up by SEQ ID NO: 12, or SEQ ID NO: 13, or SEQ ID NO: 11 within the DPP9 or DPP8 in silico 3D-model by molecular modeling, by using routine techniques well known in the art. Using conventional molecular modeling software, the skilled person will be able to assess the likelihood that the candidate compound binds and inhibits DPP8 and/or DPP9. Steps (b) and (c) may be iteratively repeated, until an optimum fitting (lowest energy level) of the candidate compound within the structure of SEQ ID NO: 12, or SEQ ID NO: 13, or SEQ ID NO: 11 has been determined. If the candidate compound exhibits a certain likelihood that it may work as an non-competitive allosteric inhibitor of DPP8 and/or DPP9, it may further optionally be assayed in an in vitro test, in order to determine whether said candidate compound decreases the enzymatic activity of DPP9 and/or DPP8 in vitro. As can be seen from the above, the skilled person can use the information provided herein in order to specifically screen and pre-select candidate compounds, which may then be tested in a second step in vitro.

Therefore, there is also provided an in vitro method for characterization of a candidate compound as a non-competitive allosteric inhibitor of DPP9 and/or DPP8, which method comprises the steps of: (a) providing a candidate compound for the characterization, which is expected to bind to an amino acid sequence motif of SEQ ID NO: 12, or SEQ ID NO: 13, or SEQ ID NO: 11, within DPP9 and/or DPP8, and (b) determining whether said candidate compound indeed decreases the enzymatic activity of DPP9 and/or DPP8 in vitro in a non-competitive allosteric manner. This can be tested in vitro, as exemplified in the Examples below.

For example, one may test the change in enzymatic activity of DPP9 and/or DPP8 in an assay using 25 nM purified recombinant enzyme (DPP9 or DPP8), and varying concentrations of GP-AMC (0, 31, 62.5, 125, 250, 500 mM GP-AMC), and the candidate compound to be tested in the range between 0.04 to 50 µM, in TB buffer (20 mM Hepes/KOH pH 7.3, 110 mM potassium acetate, 2 mM Mg acetate, 0.5 mM EGTA), supplemented with 0.2% Tween-20, 1 mM dithiothreitol. Release of AMC from GP-AMC can be measured using the Appliskan microplate fluorimeter (Thermo Scientific) with 380 nm (excitation) and 480 nm (emission) filters and the Skanit software, and can be analysed using the Prism software.

The skilled person can then use the results of such testing in order to prepare a Lineweaver-Burk-plot, which allows determining whether a) the candidate compound indeed inhibits the enzymatic activity of DPP8 and/or DPP9, and b) whether this is done in an allosteric non-competitive manner.

Finally, DPP8 and DPP9 have been shown to influence cell behavior such as cell-extracellular matrix interactions, proliferation and apoptosis. DPP9 transcription is abundant in human tumor cell lines such as melanoma, chronic myelogenous leukemia, colorectal adenocarcinoma, neuroblastoma, and HeLa cells (a cell line derived from cervical cancer), and is upregulated in human testicular tumors, as well as breast cancer cell lines, in particular estrogen negative breast cancer cell lines. DPP8 transcription as compared to transcription of other DPPs significantly increased in breast cancer and ovarian cancer cell lines. Constitutive expression of DPP8 and DPP9 was also found in B cell chronic lymphocytic leukemia. The expression of DPP8 and DPP9 in tumor tissues and cell lines indicates that they may have roles in tumor pathogenesis (reviewed in Zhang et al., 2013). As demonstrated in Example 10, the non-competitive allosteric peptide inhibitor of DPP9 and/or DPP8 as disclosed herein can be used to reduce proliferation of cancer cells. Therefore, further contemplated is a non-competitive allosteric peptide inhibitor of DPP9 and/or DPP8 as disclosed herein for use in medicine and/or veterinary medicine, in particular in oncology. More specifically, the non-competitive allosteric peptide inhibitor of DPP9 and/or DPP8 as disclosed herein may be used for the treatment of cervical cancer, melanoma, chronic myelogenous leukemia, colorectal adenocarcinoma, neuroblastoma, testicular tumors, breast cancer, in particular estrogen negative breast cancer, ovarian cancer cell lines, and/or B cell chronic lymphocytic leukemia.

For this purpose, the non-competitive allosteric peptide inhibitor of DPP9 and/or DPP8 is preferably formulated in a pharmaceutical composition comprising a pharmaceutically acceptable carrier, excipient and/or diluent. The carrier may be chosen dependent on the route of administration as well as on the concentration of the peptide inhibitor. The pharmaceutical composition may be in the form of a lyophilised composition or an aqueous solution, in particular a stabilized aqueous solution. Generally, an appropriate amount of a pharmaceutically acceptable salt is used in the carrier to render the composition isotonic. For example, the carrier may include but is not limited to phosphate buffered saline, Ringer's solution, dextrose solution, water, emulsions, such as oil/water emulsions, various types of wetting agents, sterile solutions, etc. The acceptable excipients, carriers, or stabilisers are non-toxic at the dosages and concentrations employed, including buffers such as citrate, phosphate, and other suitable organic acids; salt-forming counter-ions, e.g. sodium and potassium; low molecular weight (>10 amino acid residues) polypeptides; proteins, e.g. gelatine, or serum albumin; hydrophilic polymers, such as polyvinylpyrrolidone; amino acids, e.g. histidine, glutamine, lysine, asparagine, arginine, or glycine; carbohydrates including glucose, mannose, dextrins, mono- and/or disaccharides, e.g. sucrose, mannitol, trehalose or sorbitol; complexing agents, e.g. EDTA; non-ionic surfactants, such as Pluronics, Tween, or polyethylene glycol. Preservatives may also be present such as, for example, antimicrobials, antioxidants, chelating agents, and inert gases and the like. Examples for antioxidants and/or preservatives are, e.g. methionine, ascorbic acid, tocopherol, octadecyldimethylbenzyl ammonium chloride, hexamethonium chloride, benzalkonium chloride, benzethonium chloride, phenol, butyl or benzyl alcohol, alkyl parabens such as methyl or propyl paraben, catechol, resorcinol, cyclohexanol, 3-pentanol, or m-cresol. Suitable carriers and their formulations are described in greater detail in Remington's Pharmaceutical Sciences, 17th ed., 1985, Mack Publishing Co.

The subject to be treated may be a non-human animal, preferably a mammal such as a horse, cow, pig, mouse, rat, guinea pig, cat, dog, goat, sheep, or non-human primate. More preferably the subject to be treated is a human. Preferably, the peptide inhibitor is formulated in a pharmaceutical composition comprising a pharmaceutically acceptable carrier, excipient and/or diluent, as defined above.

The pharmaceutical composition may comprise the peptide inhibitor in an amount of about 1 ng/kg to about 1 mg/kg, and the pharmaceutical composition may be administered at a suitable dose, i.e. about 1 ng/kg body weight to about 10 mg/kg body weight of a subject, preferably at a dose of about 10 ng/kg to about 1 mg/kg, more preferably at a dose of about 100 ng/kg to about 0.5 mg/kg per body weight. However, the dosage regimen will be determined by an attending physician and depend upon many factors, including the patient's size and condition, body surface area, age, sex, time and route of administration, and on other drugs being administered concurrently. Administration will preferably be intravenously but may also be subcutaneously, intramuscularly, intraperitoneally, intracranially or directly into the tumor. The compositions comprising a peptide inhibitor as described and provided herein may also be administered directly, e.g., by biolistic delivery to an internal or external target site or by catheter to a site in an artery or a vein.

The peptide inhibitor, preferably formulated in a pharmaceutical composition, may be administered, e.g., enterally, orally (e.g., formulated as a pill, tablet (buccal, sublingual, orally, disintegrating, capsule, thin film, liquid solution or suspension, powder, solid crystals or liquid), rectally (e.g., as a suppository, enema), via injection (e.g., intravenously, subcutaneously, intramuscularly, intraperitoneally, intradermally) via inhalation (e.g., intrabronchially), topically, vaginally, epicutaneously, or intranasally. Preferably, the composition is administered via injection, in particular intravenously, subcutaneously, intramuscularly, intraperitoneally, intracranially, or intradermally; more preferably the composition is administered intravenously. It is also contemplated to administer the peptide inhibitor or the pharmaceutical composition intratumorally. Preparations for parenteral administration include sterile aqueous solutions, e.g., water, alcoholic/aqueous solutions, including saline and buffered media, including include sodium chloride solution, Ringer's dextrose, dextrose and sodium chloride solution, lactated Ringer's solution; or non-aqueous solutions, e.g., propylene glycol, polyethylene glycol, vegetable oils (such as olive oil), and injectable organic esters (such as ethyl oleate), suspensions, and emulsions. Intravenous vehicles include fluid and nutrient replenishers, electrolyte replenishers (such as those based on Ringer's dextrose), and the like.

The above described invention will become more clear and apparent in view of the following figures and examples, which, however, are not to be construed as being limiting the invention.

DESCRIPTION OF THE FIGURES

FIG. 1: Identification of DPP8 and DPP9 as novel and specific interacting partners of SUMO1.

Figure 4:
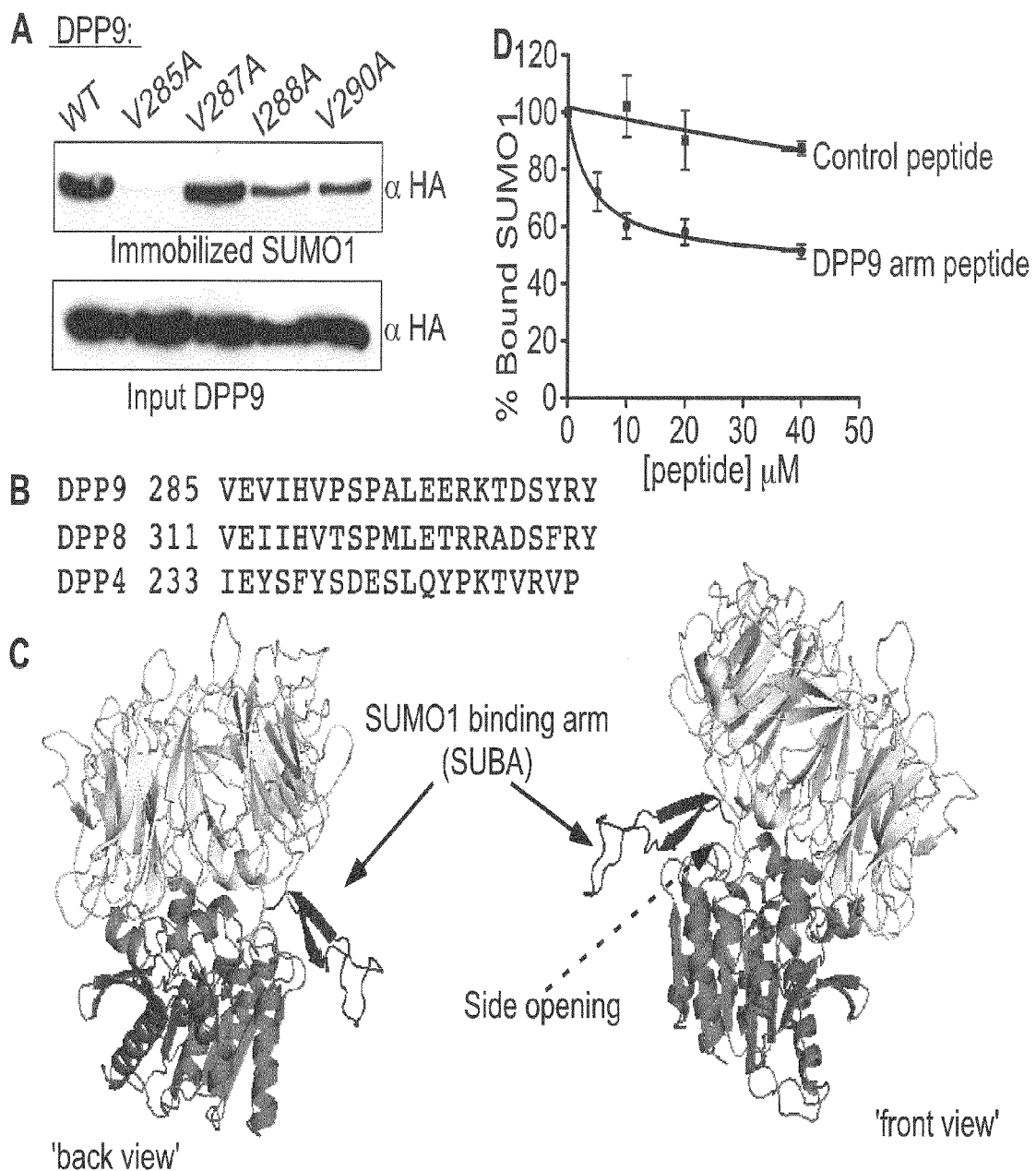

A. SUMO1 or SUMO2 were immobilized on sepharose beads and incubated with HeLa cell lysates. Interacting proteins were eluted with increasing salt concentrations, separated on SDS PAGE and analysed by mass spectrometry. Shown is a Coomassie staining of fractions eluted from bead-immobilized SUMO1 and SUMO2. B. SUMO-binding assay as in A, ovalbumin-coupled beads were used for control (Ov). Proteins were analysed by immunoblotting using specific antibodies, the input lane corresponds to 0.2% of the input. For detection of Uba2, DPP8, POP and PASP 10% of the eluate were loaded per lane. For DPP9 detection only 1% of the eluate were loaded per lane. C. HeLa cell extracts were incubated with immobilized ovalbumin, SUMO1 or SUMO2 beads. Bead-bound fractions (upper panel) were tested for hydrolysis of GP-AMC for 60 minutes. Fluorescence was measured using 380-nm (excitation)

and 480-nm (emission) filters. The remaining unbound fractions (depleted lysates) were tested for release of AMC from GP-AMC (lower panel). These experiments were repeated four times, in triplicates, shown is one representative. D. Shown is a coomassie stained gel of recombinant DPP8 and DPP9 that were expressed and purified from insect Sf9 cells. E. Recombinant DPP8, DPP9 and Uba2 were incubated with immobilized SUMO1/SUMO2 or ovalbumin (Ov) coupled beads. Input (50 ng) and eluted proteins (50% of elutae) were detected by western blotting with DPP8 and Uba2-specific antibodies. For the detection of DPP9, 10% of eluted proteins were loaded. F. Results of an ELISA assay: binding of SUMO1 to immobilized DPP8, DPP9 or ovalbumin. Bound SUMO1 was quantified using SUMO1 specific antibodies. Experiments were repeated three times, in triplicates, error bars are shown.

FIG. 2: DPP9 interacts with the E67-interacting loop (EIL) on SUMO1 independently of the SIM-interacting groove (SIG).

A. SUMO1 and SUMO1-SIG mutant proteins (SUMO1K37AV38A and SUMO1V38AK39A) were immobilized on Sepharose beads and incubated with HeLa cell extracts. Ovalbumin (Ov) coupled beads were used for control. Bound proteins were detected by western blotting using specific antibodies. B. Shown is a pull down assay as in A with recombinant DPP9, DPP8, Uba2 or GST-PIAS3. C. Recombinant DPP9 was incubated with 15 mer peptides of a peptide library covering SUMO1 amino acid sequence. The DPP9-peptide solutions were then incubated with SUMO1-immobilized beads. Following extensive washing steps, bound DPP9 was eluted with sample buffer and detected DPP9-specific antibodies. D. Recombinant DPP8 and DPP9 were incubated with SUMO1-immobilized beads. To elute bound proteins, beads were incubated with either SUMO1-peptide 5 (overlapping SIG) or with SUMO1-peptide 9. E. SUMO1 was mutated in amino acids covering the sequence of SUMO1 peptide 9. Recombinant SUMO proteins were immobilized on ELISA slips and incubated with recombinant DPP9. Interacting DPP9 was detected using a DPP9 specific antibody. Experiments were repeated three times in triplicates, shown is a representative, including error bars. F. Recombinant DPP9, Uba2 and GST-PIAS3 were incubated with bead-immobilized SUMO1 or SUMO1 mutants. Interacting proteins were eluted with sample buffer and detected using specific antibodies. G. Shown is a 3D structure of SUMO1 bound to a SIM peptide (Protein Data Bank accession code 2ASQ). The E67-interacting loop (EIL) is located on the opposite side (F66-G68) of the SIG.

FIG. 3: A single point mutation in SUMO2 leads to gain of interaction with DPP9.

A. Alignment of SUMO1 (SEQ ID NO: 1), SUMO2 and SUMO3 (SEQ ID NO: 2) in the amino-acid sequence corresponding to the EIL in all homologs. B. Recombinant DPP9 or Uba2 (for control) were incubated with bead-immobilized SUMO1, SUMO2 or SUMO2 mutants (S2). Bead-Bound proteins were eluted and detected using specific antibodies.

FIG. 4: SUMO1 interacts with an 'arm' motif in the propeller of DPP9.

A. HA-tagged DPP9 mutants (DPP9V285A, DPP9V287A, DPP9I288A and DPP9V290) were expressed in HEK293T cells and purified using anti-HA beads agarose. Purified DPP9 proteins (input) were then incubated with SUMO1-immobilized beads. Bound DPP9 was eluted and analysed by western blotting using anti HA antibodies. B. Alignment of the amino-acid sequences corresponding to the 'arms' of DPP9 (SEQ ID NO: 3), DPP8 (SEQ ID NO: 4) and DPPIV (SEQ ID NO: 5). C A homology model of DPP9 (published by (Park et al., 2008)), shown from the 'back' side and the 'front' (180° rotation) side, which also reveal the so-called side opening. Color code: the hydrolase domain is dark grey, the eight-bladed propeller is light grey and the extended SUMO-binding-arm is indicated. D. Results of an ELISA assay. Prior to the assay SUMO1 was incubated with varying concentrations of a peptide corresponding to the arm of DPP9 (or a control peptide). The SUMO1-peptide mix was then added to immobilized DPP9, and interacting SUMO1 was quantified using SUMO1-specific antibodies.

Figure 5:
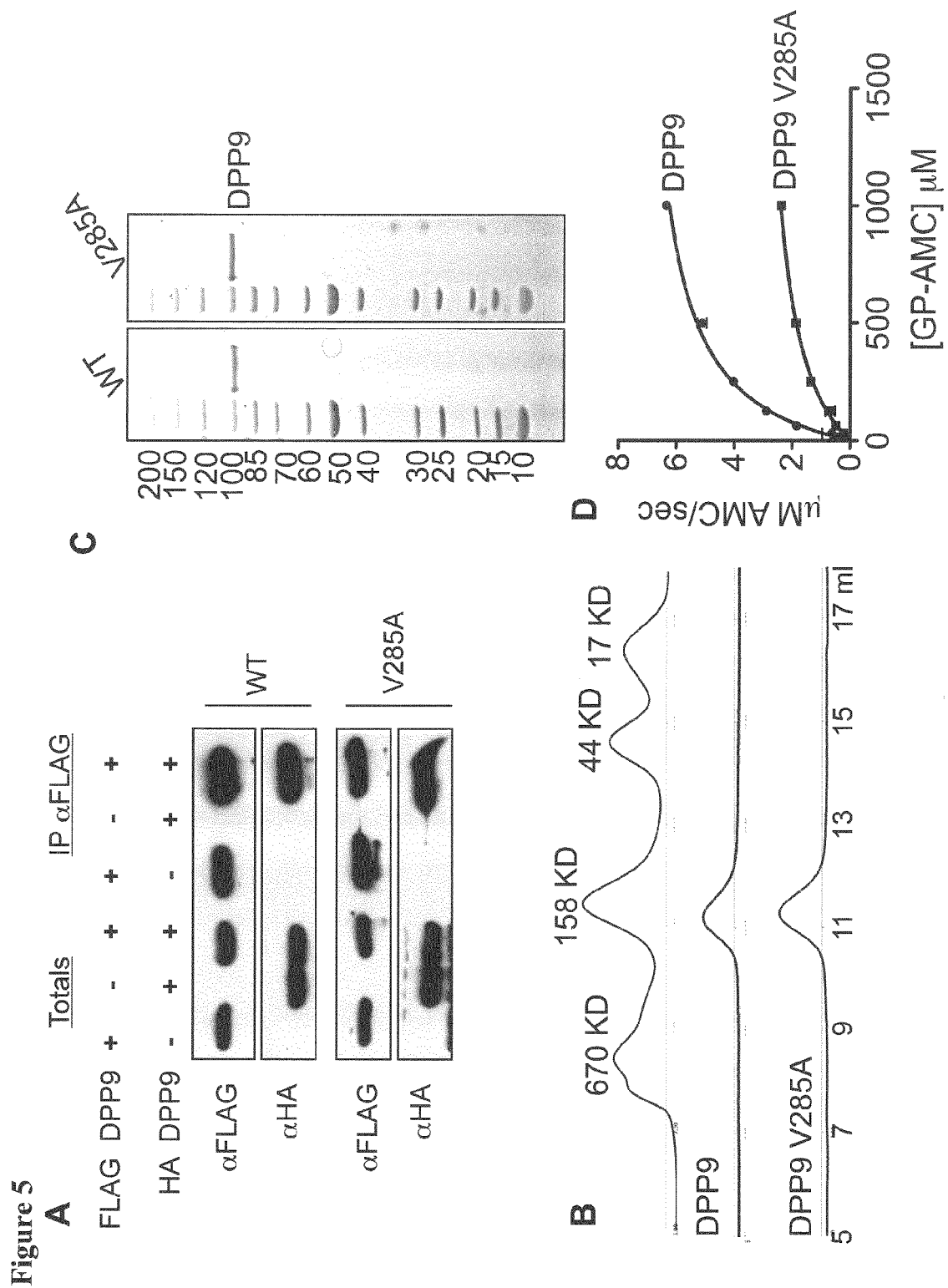

FIG. 5: The SUMO1 binding arm overlaps with a region critical for DPP9 enzymatic activity.

A. DPP9 wild-type and V285 mutants form dimers in cells. HEK293T cells were transfected with either HA or Flag tagged DPP9, or both together. Alternatively, cells were transfected with HA or Flag tagged versions of DPP9V285A (Totals). Lysates were immunoprecipitated using anti-Flag beads, and tested for the presence of both HA and Flag DPP9. B. Elution profiles of 100 microgram recombinant DPP9 wild-type and DPP9V285A mutant on a gel exclusion chromatography, using analytical Superdex S200. C. Coomassie staining of recombinant wild-type DPP9 and DPP9 V285A mutant purified from insect cells. D. Michaelis-Menten analysis for GP-AMC hydrolysis by wild-type DPP9 or DPP9V285A mutant. Experiments were repeated 4 times, shown is an experiment performed in triplicates, including error bars. The hydrolysis of GP-AMC by recombinant DPP9 was measured using 380-nm (excitation) and 480-nm (emission) filters.

Figure 6:
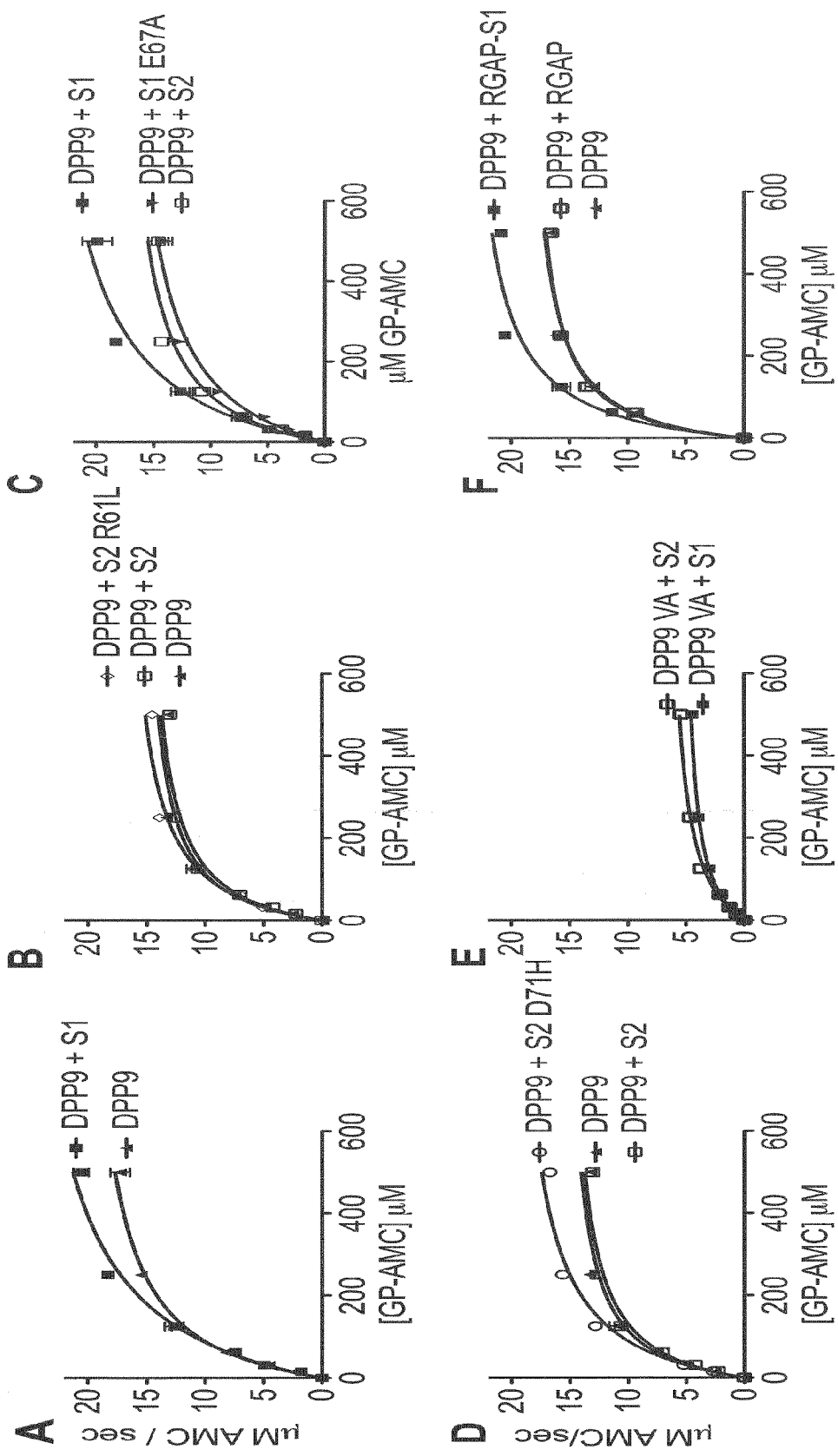

FIG. 6: Regulation of DPP9 activity by SUMO1.

A-F. Michaelis-Menten analysis: The hydrolysis of GP-AMC by recombinant DPP9 was measured using 380-nm (excitation) and 480-nm (emission) filters. The experiments were repeated at least 4 times, shown are examples, each performed in triplicates, including error bars. A. Activity of recombinant DPP9 alone, or in the presence of SUMO1. B. Activity of recombinant DPP9 was measured as in A, in the presence of SUMO2 or SUMO2R61L. Control samples contained DPP9 alone. C. Activity of DPP9 alone or in the presence of SUMO1, SUMO2 or SUMO1 E67A. D. Activity of DPP9 alone or in the presence of SUMO2 or SUMO2D71H. E. Activity of DPP9 V285A mutant in the presence of SUMO1 or SUMO2. F. Activity of DPP9 alone, in the presence of a model protein RanGAP, or in the presence of RanGAP modified with SUMO1 (S1-RG). G. HeLa cells were transfected with siRNA against SUMO1 (SUMO1-i, SUMO1-ii) and harvested after 72 h. Non-targeting siRNA was used for control. Shown is a Western blot of cytosol extracts from the siRNA treated cells (10 μg of protein extract per lane) developed with antibodies against SUMO1 and actin as a loading control. H. Lysates from the silenced cells in were tested for release of AMC from GP-AMC. This assay was repeated three times.

FIG. 7: Model: allosteric activation of DPP9 by SUMO1.

DPP9 (shown a monomer of a dimer) exists in two alternative conformations, which are found in equilibrium and differ in their activity. Protein X interacts weakly with DPP9. Sumoylation of protein X leads to a stronger association with DPP9 and stabilization of the more active form of the enzyme.

Figure 8:
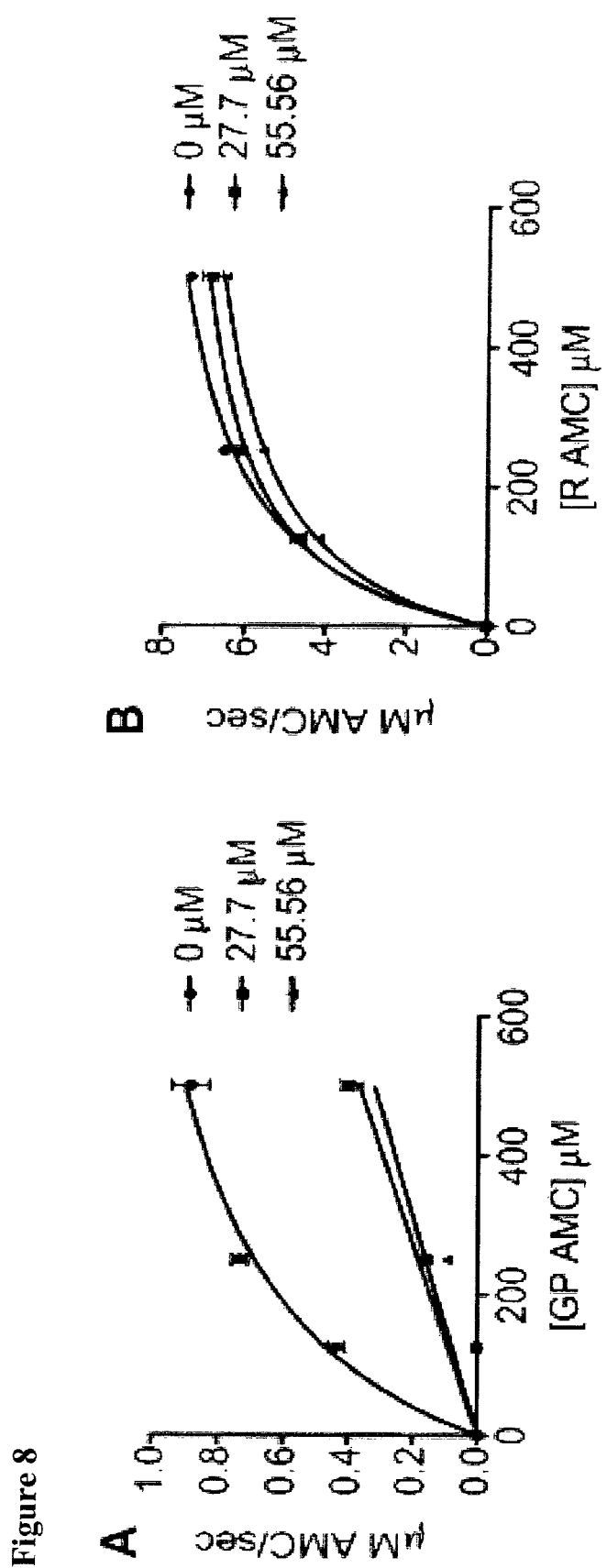

FIG. 8: The EIL peptide inhibits cytosolic prolyl peptidase activity.

HeLa cytosolic fractions were incubated with 0, 27.7 or 55.6 μM peptide EIL, and immediately tested for hydrolysis of varying concentrations of A. GP-AMC or B. R-AMC.

Fluorescence was measured using the Appliskan microplate fluorimeter (Thermo Scientific) with 380 nm (excitation) and 480 nm (emission) filters and the Skanit software, and analysed using the Prism software. Each experiment was performed at least three times, in replicates of four.

Figure 9:
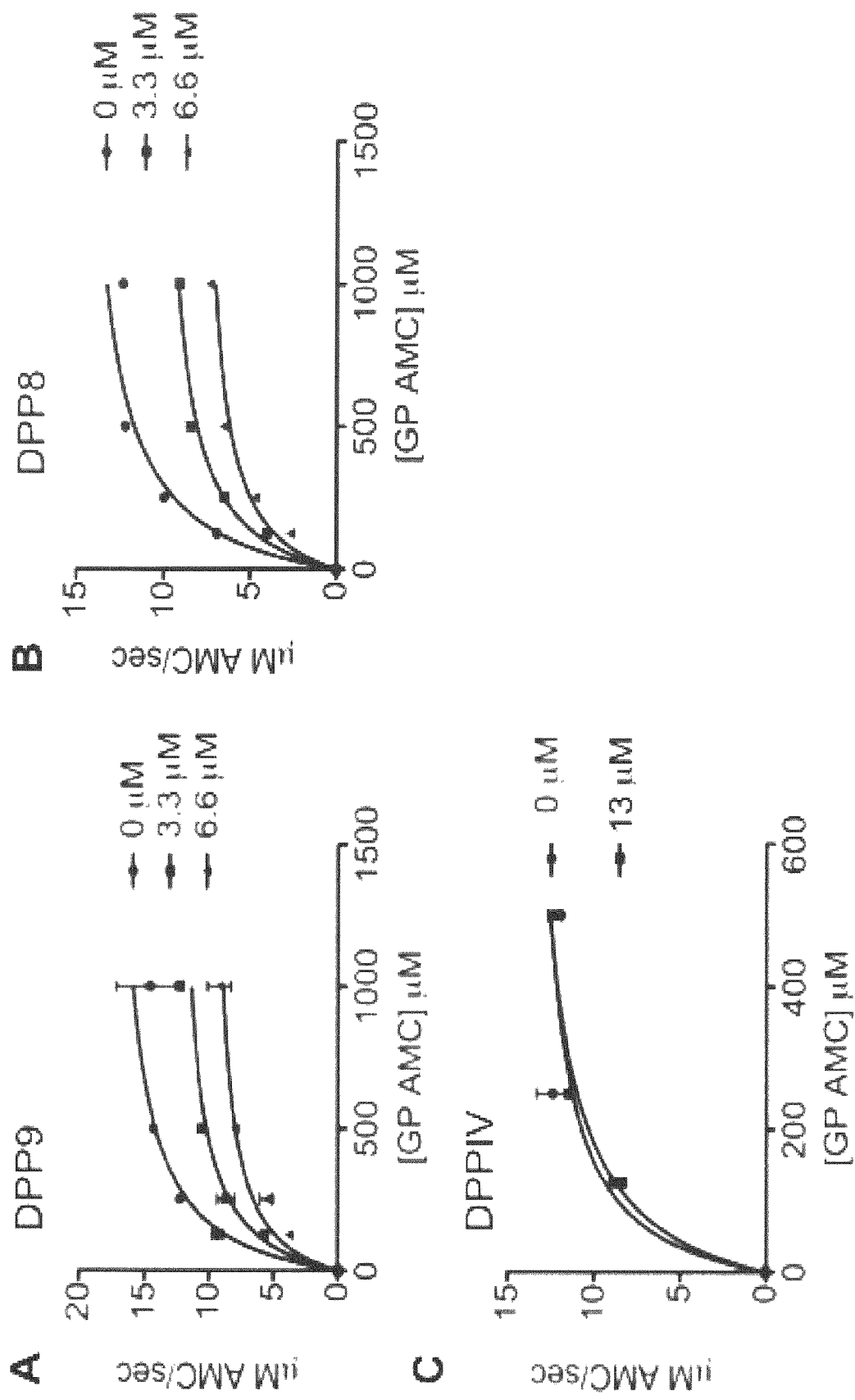

FIG. 9: The EIL selectively inhibits DPP8 and DPP9, but not DPPIV.

A&B 25 nM purified recombinant (A) DPP9 or (B) DPP8 were incubated with varying concentrations of the EIL peptide (0, 3.3 µM and 6.6 µM) and tested for hydrolysis of GP-AMC (1000, 500, 250, 125, 0 µM). C. 25 nM DPPIV was tested for the hydrolysis of GP-AMC (500, 250, 125, 0 µM) in the presence of 0 or 13 µM EIL peptide. Fluorescence was measured using the Appliskan microplate fluorimeter (Thermo Scientific) with 380 nm (excitation) and 480 nm (emission) filters and the Skanit software, and analysed using the Prism software. Each experiment was performed at least three times, in replicates of four.

Figures 10, 11:
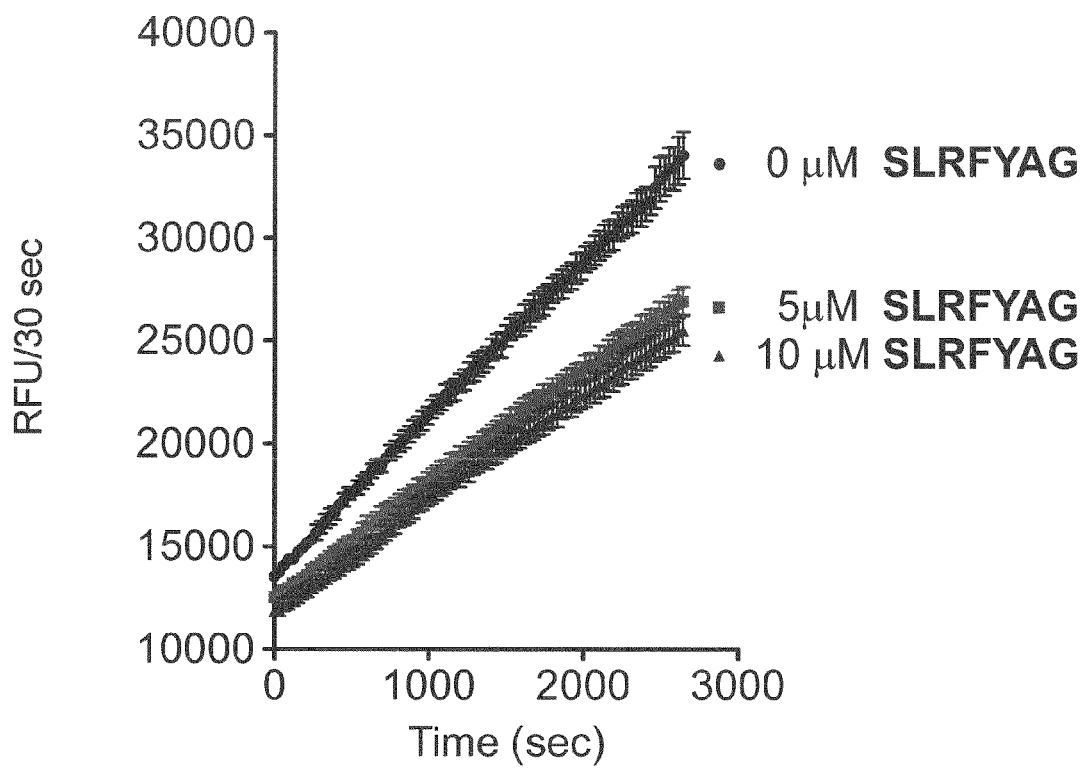

FIG. 10: Alignment of DPPIV, DPP8 and DPP9 (long form).

The figure shows an alignment of DPP9 (SEQ ID NO: 6), DPP8 (SEQ ID NO: 7), and DPPIV (SEQ ID NO: 8). The ARM-motif is boxed.

FIG. 11: Effect of SLRFLYAG in cells

Cells were incubated for 30 minutes with 0 µM, 5 µM or 10 µM SLRFLYAG (SEQ ID NO: 40) and 100 µM carrier pep-1. Cytosolic extracts of cells (5 µg) were then tested for hydrolysis of 0.5 mM GP-AMC.

Figure 12:
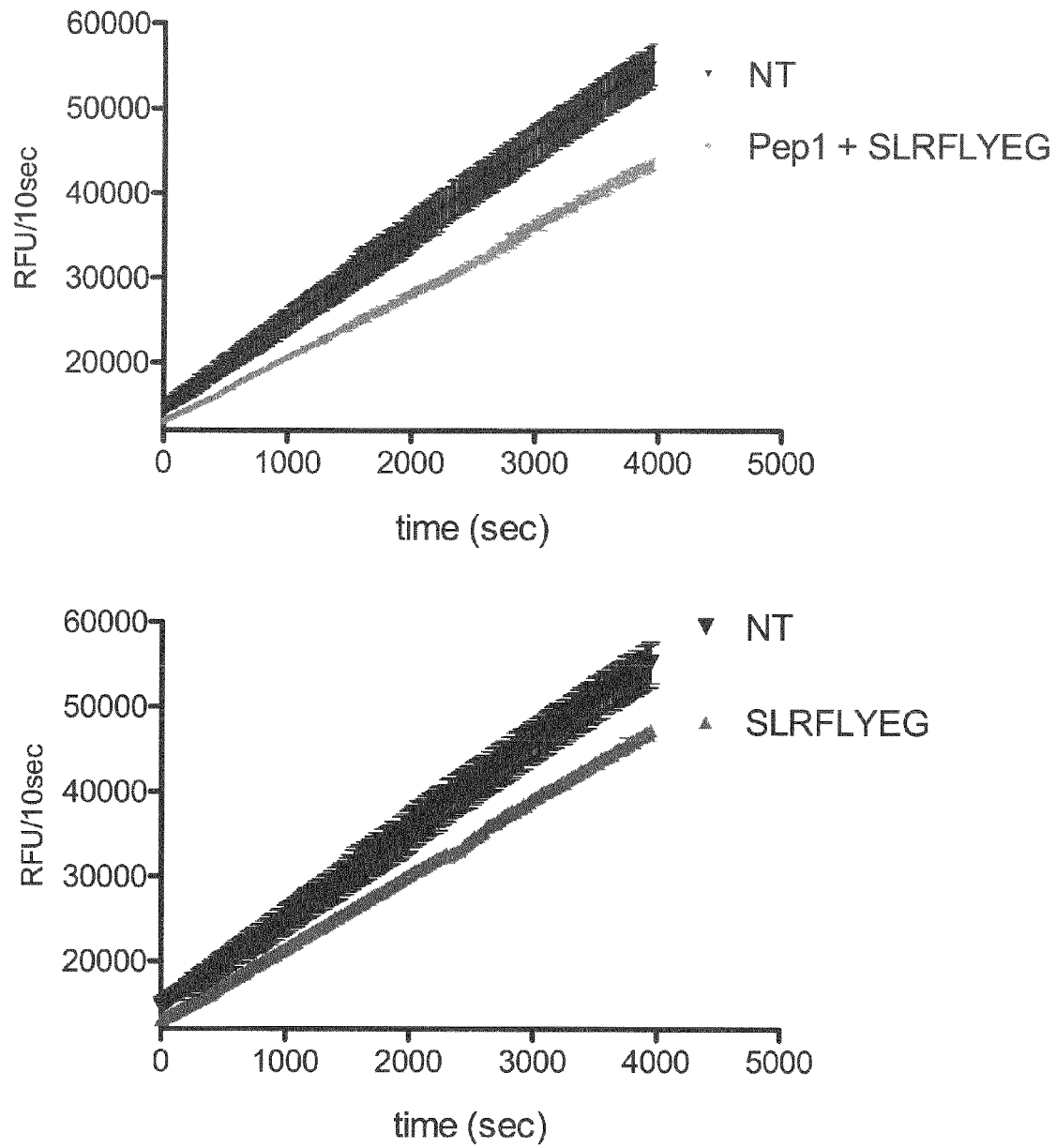

FIG. 12: Prolyl peptidase activity of cytosolic extracts is inhibited after exposing of cells for 30 minutes to the SLRFLYEG (SEQ ID NO: 38) peptide.

Figure 13:
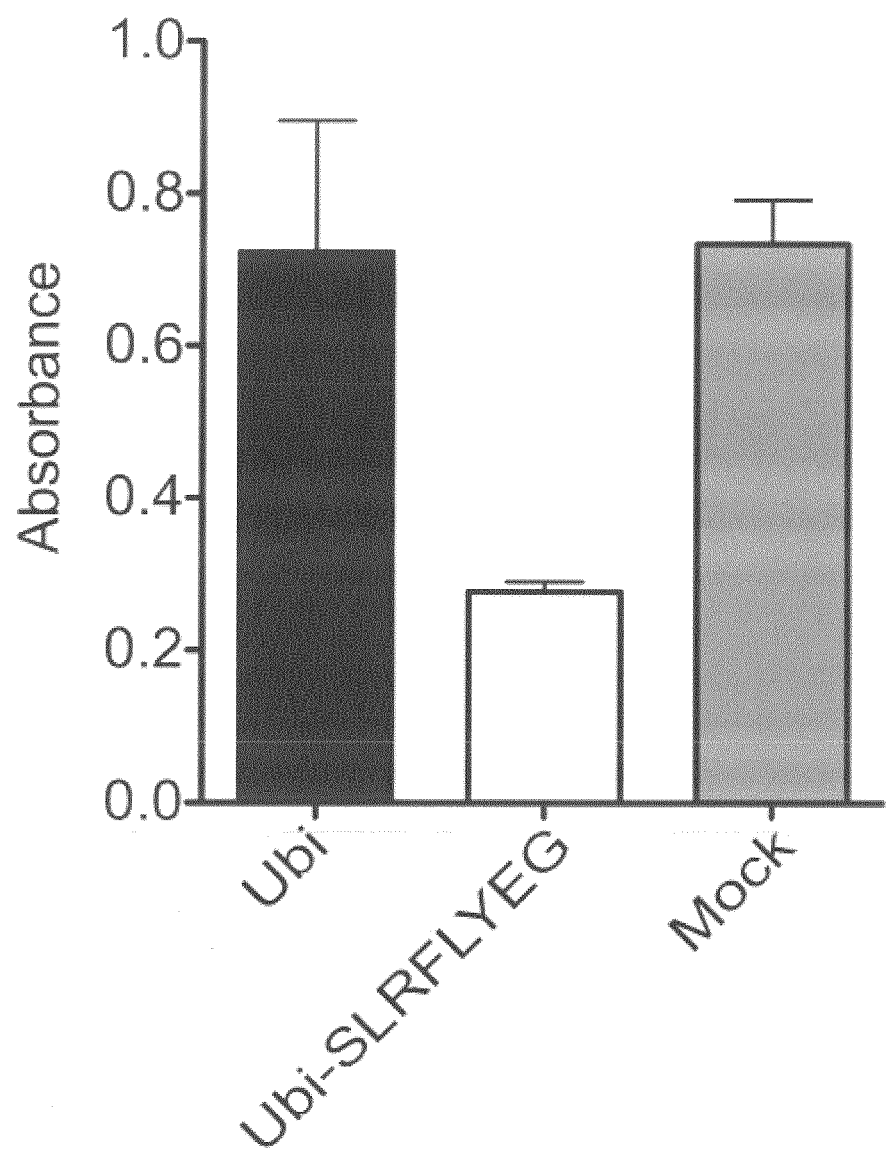

FIG. 13: Cells exposed to SLRFLYEG (SEQ ID NO: 38) show reduced proliferation.

EXAMPLES

Materials and Methods

Cell culture and siRNA experiments: HEK293T and HeLa cells were maintained in Dulbecco's modified Eagle's medium with 10% fetal bovine serum. siRNA oligos against SUMO1 were synthesized by Life Technologies: SUMO1-i (5'-GGA UAG CAG UGA GAU UCA CUU CAA-3'; SEQ ID NO: 9) SUMO1-ii (5'-GGA AGA AGA UGU GAU UGA AGU UUA U-3'; SEQ ID NO: 10). HeLa cells 30% confluent were transfected with 120 picomols of siRNA using Oligofectamin reagent (Life Technologies) in antibiotics-free medium. 48 h later cells were retransfected in the same conditions, and harvested after a total of 72 hours.

Antibodies: Goat anti-Uba2 were previously described. Rabbit anti PIAS2 antibodies were purchased from Sigma, mouse-GST antibodies were purchased from Santa-Cruz. Mouse anti GMP1 antibodies were obtained from the Developmental Studies Hybridoma Bank. Rabbit anti DPP9 antibodies were purchased from Abcam. For ELISA assay we the inventors produced goat anti DPP9 specific antibodies, by injecting a goat with 500 mg full length DPP9 on days 0, 40 and 70. The goat anti-DPP9 antibodies were purified from the serum by incubation with DPP9-coupled beads followed by acetic acid elution.

Plasmids: SUMO1 and SUMO2 were cloned into pET11. DPP8 and DPP9 were subcloned into a pFASTBacHT plasmid (Invitrogen), baculoviruses were generated according to the instructions of the Bac to Bac Baculovirus expression system, using SF9 cells. DPP9 was cloned into pcDNA3.1 vector for expression of C-terminal HA or Flagged tagged DPP9 (using the BamH1 and Not restriction sites). Single point mutations in SUMO1, SUMO2 or DPP9 were generated using primers for site directed mutagenesis.

Recombinant Protein purification: Purification of Ran-GAP, SUMO1 and SUMO2 were described previously (Meulmeester et al., 2008; Pichler et al., 2002). For the expression of recombinant DPP8 and DPP9, SF9 insect cells were infected with a high titer DPP8 or DPP9 viral stock for 72 h. Cells were harvested by centrifugation and resuspended in 25 mM Hepes pH7.5, 400 mM NaCl, 5 mM imidazole, 5 mM beta-mercaptoethanol. Cells were then sonificated and centrifuged at 100,000 g for 1 hour at 4° C. The cleared lysate was then incubated with Ni-NTA beads for 2 hours at 4° C. (Qiagen). After extensive washing, proteins were eluted with 25 mM Hepes pH 7.5, 50 mM NaCl, 100 mM imidazole, 5 mM beta-mercaptoethanol. Eluted protein were then separated on a mono Q column (General electric), using a gradient of 0-0.5 M NaCl in 50 mM TRIS pH 8, 2 mM DTT. In a last step, proteins were loaded on a preparative Superdex 200 column (General electric) equilibrated with transport buffer (TB: 20 mM Hepes/KOH pH 7.3, 110 mM potassium acetate, 2 mM Mg acetate, 0.5 mM EGTA, 2 mM DTT).

Peptides: All Peptides: DPP9 arm and the SUMO1-peptide library (>80% purity) were purchased from Genescript.

SUMO pull down screen: SUMO proteins were coupled to CnBr Sepharose (Sigma-Aldrich) at a concentration of 1 mg protein per ml beads. To identify SUMO-interacting proteins, 25 g of frozen HeLa cell pellets were resuspended in 50 ml TB (20 mM Hepes/KOH pH 7.3, 110 mM potassium acetate, 2 mM Mg acetate, 0.5 mM EGTA), supplemented with protease inhibitors (1 µg/ml leupeptine, pepstatine, aprotinin and 2 mM DTT) and homogenized by douncing. Cell lysates were centrifuged at 10,000 g for 15 minutes and again at 100,000 g for 1 hour. 10 ml supernatant was incubated at 4° C. with 200 ml SUMO1/SUMO2 or control beads that were inactivated with ethanolamine. After 2 hours of incubation, beads were washed and eluted in TB supplemented with protease inhibitors and increasing NaCl concentrations (0.25, 0.5 or 1 M). Eluted proteins were precipitated with methanol-chloroform, resuspended in LDS sample buffer, separated on a 4-12% NuPAGE gradient gel (Invitrogen), and stained with colloidal Coomassie. In-gel tryptic digestion, desalting, and LC-MSMS analysis were performed as reported previously (Sauer et al. 2005). All pkl files corresponding to one sample were merged into a single mascot generic data file and searched against the human IPI protein database (V3.26) using Mascot with Mascot Server (V2.2). The following settings were used: digestion with trypsin allowing one miss cleavage, carbamylation of cysteine as fixed modification, oxidation of methionine as variable, 150 ppm MS mass accuracy and 0.3 Da for fragmentation masses.

SUMO pull downs with recombinant proteins and competition assays: 500 ng recombinant proteins were incubated at 4° C. with bead immobilized SUMO1, SUMO2 or ovalbumin in TB supplemented with 0.5% Tween-20 and 0.2 mg/ml ovalbumin. Following a 1 hour binding period, beads were washed in TB containing 0.5% Tween-20 and protease inhibitors. Proteins were eluted with sample buffer. For peptide competition assays: recombinant DPP9 (500 ng) was incubated with peptides from the SUMO1 peptide library (0.1 mg/ml) for 1 hour prior to incubation with the SUMO-immobilized beads.

ELISA: A 96 well plate (Immuno 96 MicroWell™ Solid Plates, Nunc) was coated with 600 ng purified recombinant proteins per well in 100 µl TB, overnight at 4° C. Next, wells were blocked with ELISA buffer (TB supplemented with 3% BSA) for 1 h at room temperature. After blocking, recombinant interacting proteins were added to the wells. Following 2 hours of incubation at 25° C., wells were washed four times. Interacting proteins were detected using specific antibodies diluted in ELISA buffer: goat anti DPP9 antibody or anti GMP antibody (SUMO1). After incubation with secondary antibodies, wells were washed with ELISA buffer and ddH20. Reactions were developed with TMB-substrate reagent set from BD (OptEIA substrate). Absorbance was measured at 420 nm on an Appliskan microplate fluorimeter (Thermo Scientific) and the Skanit software. Experiments were performed at least three times, in triplicates.

Immunoprecipitations: HEK293T cells were transfected with pcDNA3 vectors using the calcium phosphate precipitation method. 48 hours later, cells were harvested and dounced in ice cold TB supplemented with 0.2% Tween-20. The homogenate was centrifuged at 4° C., 100,000 g for 20 min. Supernatant were precleared for 30 min with protein G beads, followed by immunoprecipitation for 2 hours at 4° C. with mouse anti-HA or mouse anti-FLAG beads (SIGMA). After extensive washing with TB containing 0.2% Tween-20, bound proteins were eluted with 0.5 mg/ml HA or FLAG peptide in the same buffer.

Size exclusion chromatography: 100 microgram purified DPP9 wild-type or V285A mutant were diluted in 500 microliter TB supplemented with 0.2% Tween-20. Recombinant DPP9 wild-type or mutant were then loaded on an analytical Superdex 200 column (General electric) for size exclusion chromatography. DPP9 concentration in the loop equals 2 µM.

Kinetics assays: Purified recombinant DPP9 (25 nM) was incubated with varying concentrations of GP-AMC, in TB supplemented with 0.2% Tween-20, 1 mM ditiothreitol. For inhibition assays, inhibitory peptides were added directly to the reaction mixture. For activation by SUMO 0.2 mg/ml BSA, was added to the buffer to prevent non specific binding. DPP9 were incubated with 2.5 µM of either SUMO1, SUMO1 E67A, SUMO2 for 2 hour on ice prior to the assay. Alternatively DPP9 was incubated with 1 µM of RanGAP or RanGAP modified with either SUMO1 or SUMO2 for 2 hours prior to the assay. Fluorescence was measured using the Appliskan microplate fluorimeter (Thermo Scientific) with 380 nm (excitation) and 480 nm (emission) filters and the Skanit software, and analysed using the Prism software. Each experiment was performed at least three times, in replicates of four.

Prolyl peptidase activity in SUMO1 silenced cells: HeLa cells were silenced for 72 hours with SUMO1-specific siRNA (SUMO1-1 and SUMO1-3). A non-targeting siRNA was used as control. After 72 h cells were washed in PBS, harvested and lysed in TB supplemented with 1 mM DTT and 400 nM SUMO2-VE (SENP inhibitor). Equal amounts of protein (6 µM) were loaded on 15% SDS PAGE and analysed by western blot. 5 µM of cell lysates from each silenced sample were tested for hydrolysis of 0.5 mM GP-AMC.

Example 1

Identification of a Novel Interaction Between SUMO1 and the Cytosolic Prolyl Peptidases DPP8 and DPP9

The inventors identified DPP8 and DPP9 in a screen for proteins that interact preferentially with either SUMO1 or SUMO2 (FIG. 1A). Using western-blot analysis the inventors verified that both peptidases interacted with SUMO1 (FIG. 1B). To control the assay the inventors tested for the presence of Uba2, which was previously shown to contain a SIM. Importantly, in contrast to Uba2, which interacts with SUMO1 and SUMO2, DPP8 and DPP9 showed a strong preference towards SUMO1 binding (FIG. 1B).

Next, following the incubation of cell lysates with immobilized SUMO-beads, the SUMO-bound fractions were eluted and assayed for prolyl-peptidase activity by measuring the release of AMC from the model substrate Gly-Pro-AMC (GP-AMC). Prolyl-peptidase activity was recovered specifically in fractions eluted from the SUMO1, but not on SUMO2 or ovalbumin beads (bead-bound fraction—FIG. 1C). The inventors then analysed the remaining cytosolic fractions that did not bind to the SUMO or control beads (Depleted lysates) for GP-AMC cleavage. As shown in FIG. 1C, depletion of lysates with SUMO1 resulted in a significant decrease (ca. 40%) of AMC release in the unbound fraction, this decrease was not observed in lysates incubated with SUMO2. These observations suggest that a considerable proportion of endogenous DPP8 and DPP9 can interact with SUMO1, and that this fraction is enzymatically active.

To test whether these interactions are direct, the inventors expressed DPP8 and DPP9 in insect cells (FIG. 1D). Purified recombinant DPP8 and DPP9 were then analysed for binding to bead-immobilized SUMO1 or SUMO2. Importantly, the inventors could show that DPP8 and DPP9 interact directly and specifically only with SUMO1, but not with SUMO2, in contrast to recombinant Uba2, which interacted with both SUMO isoforms (FIG. 1E). As an additional approach, the inventors performed ELISA assays, by incubation increasing concentrations of SUMO1 with immobilized recombinant DPP8 or DPP9. The inventors found that SUMO1 interacted directly with DPP8 and DPP9 in a concentration dependent manner, whereas only background binding was detected in control wells that were coated with ovalbumin (FIG. 1F). Taken together, our results show that DPP8 and DPP9 are novel and direct binding partners specifically of SUMO1.

Example 2

DPP9 Interacts with a Novel Interaction Surface on SUMO1: E67-Interacting Loop (EIL)

To study the preferential association of DPP8 and DPP9 with SUMO1 but not SUMO2, the inventors aimed to identify the surfaces on SUMO1 involved in these interactions. First the inventors analysed the interaction of DPP9 with SUMO1 mutants in residues which were previously shown via NMR and crystal structures to interact with SIM containing proteins (Song et al, 2004; Hecker et al, 2006; Reverter & Lima, 2005). The inventors constructed SUMO1K37AV38A and SUMO1V38AK39A mutants, and analysed the capacity of these SUMO proteins to pull-down endogenous DPP8 and DPP9 from cell lysates. For control, the inventors analysed the binding of known SIM-containing proteins, Uba2 and PIAS2, which did not interact with SUMO1K37AV38A and SUMO1V38AK39A. In a striking contrast, both endogenous and recombinant DPP8 and DPP9 still interacted with these SUMO1-SIG mutations (FIGS. 2A&B). These results show that the interaction of both DPP8 and DPP9 with SUMO1 involves a surface different from the conventional SIG of SUMO1. To identify the surface of SUMO1 that is important for its interactions with DPP9, the inventors analysed a library of short 15 mer peptides that covered the complete SUMO1 sequence. In total 12 peptides were tested, each peptide contained a seven amino-acid overlap with the carboxy terminus of the previous peptide. The peptides were mixed with DPP9 prior to incubation with immobilized SUMO1-beads. If a peptide covers the surface of SUMO1 that associates with DPP9, it may bind to DPP9 and consequently block the SUMO1-DPP9 interaction. Most peptides did not efficiently compete with the DPP9-SUMO1 interaction (FIG. 2C). Also a peptide that includes Val 38 and Lys 39 and corresponds to the β-sheet of the SIG (peptide 5, labelled SIG), did not affect binding of DPP9 to SUMO1. In contrast, pre-incubation of DPP9 with a peptide covering amino acids 61-75 of SUMO1 (SLRFLFEGQRIADNH, peptide 9; SEQ ID NO: 1) strongly reduced the binding of DPP9 to the SUMO1 beads (FIG. 2C). Next the inventors tested whether SUMO1-peptide 9 can displace SUMO1 from the respective DPP8-SUMO1 or DPP9-SUMO1 complex. For this, recombinant DPP8 or DPP9 were first incubated with bead immobilized SUMO1, to allow complex formation. SUMO1-peptides 5 or 9 were then added and the release of bound DPP8 or DPP9 from the SUMO beads was analysed by SDS-PAGE (FIG. 2D). Elution was is possible with SUMO1-peptide 9 but not with the control peptide that corresponds to the SIG.

Next, single amino acids in SUMO1 between phenylalanine 64 and histidine 75 (corresponding to SUMO1 peptide 9) were mutated to alanines. SUMO1 mutants were immobilized on wells of a 96 well plates and their interaction with DPP9 was analysed in ELISA assays, and compared to their interaction with wild-type SUMO1 (FIG. 2E). In this assay, SUMO1 mutations covering the sequence between phenylalanine 66 to glutamine 69 as well as a triple mutation R63AR70AH75A resulted in reduced binding of DPP9. Replacement of glutamic acid 67 of SUMO1 with alanine (S1E67A) led to the most drastic decrease in the SUMO1-DPP9 interaction, showing that this amino acid in SUMO-1 is important for association with DPP9 (FIG. 2E). Finally, the inventors immobilized SUMO1, SUMO1E67A and SUMO1K37AV38A on beads and tested for interaction with DPP9 and the SIM-containing proteins Uba2 and GST-PIAS3. As expected (FIG. 2F), Uba2 and PIAS3 interacted with SUMO1E67A but not with SUMO1K37AV38A. On the other hand, DPP9 interacted with the SUMO1 SIG mutant but not with SUMO1E67A.

These results verify that the sequence covering F66-H75, and specifically glutamic acid in position 67 of SUMO1 is important for the DPP9-SUMO1 interaction, but not the SIG (FIG. 2F). The inventors termed the sequence covering F66-H75 as the E67-interacting loop (EIL) to differentiate this sequence from the well-characterised SIG that mediates binding to the SIM. The EIL in SUMO1 is located to the loop that connects the third and fourth β-sheets of SUMO1. Importantly, the EIL is spatially separated and distinct from the SIG motif, basically on the 'opposite' side of the SIG (FIG. 2G).

Taken together these results show for the first time that the EIL functions as a second and independent surface of SUMO for non-covalent interactions with downstream effectors.

Example 3

Gain-of Binding by Point Mutations in SUMO2

To get more insight into the preferential SUMO1 binding of DPP9, the inventors analysed the homology between the SUMO paralogs in the newly identified EIL, and flanking regions. Sequence alignment shows that glutamic acid 67 in SUMO1 is replaced by aspartic acid in SUMO2; since both amino acids are negatively charged, the inventors assumed that this could not explain the strong preference in binding of DPP9 to SUMO1 (FIG. 3A). The alignment highlighted four amino acids that are not conserved in SUMO1 and SUMO2. Next, the inventors mutated single amino acids in SUMO2 to the corresponding ones in SUMO1 and tested their interaction with recombinant DPP9.

Strikingly, mutation of a single amino acid in SUMO2, aspartic acid 71 to the corresponding histidine residue in SUMO1, resulted in a full gain of binding to DPP9 (FIG. 3B). In contrast to DPP9, Uba2 interacted with all the SUMO2 variants to the same extent.

Taken together, the inventors conclude that the preferential interaction of DPP9 with SUMO1 but not with SUMO2, is due to a more negative charge of the SUMO2-EIL.

Previously, crystal structures of the SUMO conjugating enzyme Ubc9 in complex with SUMO showed that non-covalent interaction between Ubc9 and SUMO also includes the surface covering the EIL (knipscheer et al., 2007). However, in contrast to DPP9, Ubc9 does not differentiate between the SUMO homologs.

Example 4

SUMO1 Binds to an Arm-like Structure in DPP9 Which Regulates Enzymatic Activity In parallel, the inventors aimed to identify the surface in DPP9 that interacts with SUMO1. For this the inventors constructed several DPP9 mutants, concentrating first on amino acids in the propeller domain of DPP9, assuming that it would play a role in protein-protein interactions. Mutants were expressed and purified from HEK293T cells and tested for binding to immobilized SUMO1 beads. Using this approach, the inventors identified a cluster of hydrophobic amino acids in DPP9 that is essential for binding to SUMO1. Replacement of valine 285, isoleucine 288 or valine 290 by alanines resulted in a strong loss of interaction with SUMO1 (FIG. 4A). Strikingly, a single point mutation replacing valine 285 to an alanine completely abolished the DPP9-SUMO1 association. Mutation in neighbouring residues, such as in valine 287, did not affect the binding.

To better understand where the SUMO1-binding surface is localized, the inventors turned to published homology models of DPP9, based on solved structures of other members of the DPPIV family: DPPIV, DPPX and FAP (Park et al, 2008)(Rummey & Metz, 2006). Crystal structures of members of the DPPIV family show that they all form homodimers, where each monomer is built of two domains, a barrel-like α/β hydrolase and an eight bladed β propeller. An extended arm-like structure projects from blade 4 of the propeller, and is located next to a side opening in DPPIV, which is formed between the hydrolase and the propeller.

Both published DPP9 homology models predict that valine 285, isoleucine 288 and valine 290 locate to the extended arm of DPP9 (Park et al, 2008; Rummey & Metz, 2006) (FIGS. 4B &C). The inventors therefore asked whether a peptide corresponding to the extended arm of DPP9 (285-VEVIHVPSPALEERKTDSYR-304; SEQ ID NO: 11) would inhibit the SUMO1-DPP9 interaction. The inventors tested this hypothesis by incubating SUMO1 with the DPP9-arm peptide prior to incubation with immobilized DPP9. As shown in FIG. 4D, the DPP9-arm peptide competed with DPP9 for binding to SUMO1 in a concentration dependent manner. Binding of SUMO1 to DPP9 was unaffected in the presence of the same concentrations of a control peptide, or a shorter peptide corresponding to only part of the arm (FIG. 4D and data not shown).

Taken together, the inventors conclude that the arm of DPP9 mediates its interaction with SUMO1. The arm is found in all the alternative transcripts for DPP8 and DPP9 described so far and is composed of the following minimal sequence (non-conserved residues are underlined):

```
DPP9-ARM:
                                  (SEQ ID NO: 12)
LYEEVDESEVEVIHVPSPALEERKTDSYRY

DPP8-ARM:
                                  (SEQ ID NO: 13)
LYEENDESEVEIIHVTSPMLETRRADSFRY
```

The inventors define this surface as the SUMO-binding-arm (SUBA) of DPP9. The SUBA of DPP9 is part of the propeller domain, and is in close proximity to the side cavity leading to the active site.

In DPPIV the arm-structure is localized to the dimer interface of DPPIV. Recently, Tang et al showed that DPPIV mutants deleted of the arm motif fail to dimerize and are less active. However, they found that the arm of DPP9 was not essential for dimerization, since a DPP9 construct lacking parts of the arm (amino acids corresponding to I288 to Y305) is correctly folded and forms dimers. Moreover, the deletion mutant was less active compared to the wild type protein (Tang et al, 2011). The reason for the reduced activity is currently not understood.

The deletion mutant reported by Tang et al only partially covers the SUBA, since it does not include valine 285, which shows the most dramatic loss in interaction with SUMO1 if replaced by an alanine. Therefore, the inventors tested both the activity of the DPP9V285A mutant, and its ability to form dimers as the wild-type enzyme.

First, the inventors transfected HEK293T cells with FLAG-DPP9, HA-DPP9, or both. The inventors then tested whether HA-tagged DPP9 co-purifies with FLAG tagged DPP9 in co-immunoprecipitation assays. As shown in FIG. 5A, both wild-type and the DPP9V285A mutant form dimers in cells (FIG. 5A). Furthermore, size exclusion analysis of recombinant DPP9V285A and wild-type DPP9 shows that both proteins elute in a single clear peak corresponding to a DPP9-dimer (FIGS. 5B&C). These data suggest that the reduced interaction of DPP9V285A with SUMO1 is not due to unfolding or lack of dimerization of DPP9.

Importantly, a single point mutation in the SUBA motif of DPP9, valine 285 to alanine, strongly reduces DPP9 activity, compared to the wild-type peptidase (FIG. 5D). Thus, the inventors conclude that the SUMO1 binding arm of DPP9 overlaps with a surface important for its enzymatic activity.

Next, the inventors asked whether free SUMO1 has the ability to influence the enzymatic activity of DPP9. The inventors tested this question by measuring GP-AMC hydrolysis by DPP9 in the presence of recombinant SUMO1. For control, activity was compared to samples containing DPP9 alone, or samples in which DPP9 was incubated with equal concentrations of recombinant SUMO2, which does not interact with DPP9. Indeed the inventors found that the hydrolysis rate of GP-AMC by DPP9 was increased in the presence of SUMO1 in comparison to control reactions (FIGS. 6A & B). Importantly, this activation was not observed in the presence of SUMO1 mutated in a single amino acid: SUMO1E67A, which cannot bind to DPP9 (FIG. 6C). Moreover, DPP9 activity was increased in the presence of SUMO2 mutated in a single amino acid: D71H, which can interact with DPP9 (FIG. 6D). This activation was not observed in the presence of SUMO2R61L, which does not interact with DPP9 (FIG. 6B). In line with these results, the SUBA mutant DPP9V285A was not activated by SUMO1 (FIG. 6E).

Since SUMO1 is usually found in the cells in a conjugated form, the inventors tested whether a control protein, which otherwise does not interact with DPP9, could stimulate DPP9 activity, if it is modified by SUMO1. For this purpose the inventors used RanGAP as a model substrate. The inventors modified RanGAP, with SUMO1, in vitro, and tested for hydrolysis of GP-AMC by DPP9 in the presence of DPP9 alone, DPP9 with RanGAP, or DPP9 with sumoylated RanGAP. As shown in FIG. 6F the inventors found that DPP9 activity is increased when incubated with RanGAP modified by SUMO1, but not by unmodified RanGAP (FIG. 6F).

Taken together these results show that by binding to the arm of DPP9, SUMO1 but not SUMO2 can regulate DPP9 activity. This activation is dependent on the direct association between SUMO1 and the SUMO1-binding arm in DPP9.

Finally, the inventors investigated whether SUMO1 is important for DPP9 activity in cells. To this end, the inventors transfected HeLa cells with two different siRNA oligos desgined to target SUMO-1, and tested for cleavage of GP-AMC in these lysates. FIG. 6G shows the effective down-regulation of SUMO1 in these cells compared to control cells transfected with non-coding siRNA. Shown in the western blot is the sumoylated form of RanGAP1, which is the most prominent SUMO-1 modified protein (FIG. 6G). Importantly, down-regulation of SUMO1 by treatment with siRNA oligos led to reduced hydrolysis of GP-AMC in cell lysates, compared to the control cells (FIG. 6H). Taken together, these results show that SUMO1 regulates DPP9 enzymatic activity, and that this interaction is physiologically relevant.

How SUMO1 activates DPP9 is currently unclear. According to the DPP9 homology model, the SUBA is located next to a side opening, which is formed between the hydrolase and the propeller of DPP9. A crystal structure of DPPIV with a decapeptide suggests that substrates enter the hydrolase domain of DPPIV via this side opening, and not through the propeller funnel. The predicted proximity of the SUBA to the substrate entrance site raises the intriguing possibility that SUMO1 activates DPP9 by regulating the access of substrates into the hydrolase domain, or stabilizing a more 'active' state of the peptidase (FIG. 7), suggesting that SUMO1 acts as an allosteric regulator of the peptidase.

Example 5

The SUMO1 EIL Peptide (SEQ ID NO: 1) Inhibits Post Prolyl Peptidase Activity in Cells Since the EIL peptide can displace SUMO1 from a DPP9-SUMO1 or a DPP8-SUMO1 complex (FIG. 2D), the inventors tested whether the EIL peptide would inhibit the association-dependent activation of DPP8 and DPP9 by SUMO1 in cell extracts. For this the inventors incubated cytosolic extracts with the EIL peptide and tested for the hydrolysis of GP-AMC (FIG. 8A). The inventors found that the degradation of GP-AMC is strongly reduced after addition of the EIL. For control, the inventors also measured the hydrolysis of R-AMC, which is not a substrate for DPP8 or DPP9 (FIG. 8B). These results show that the EIL inhibits specifically the cytosolic prolyl peptidase activity, and that the EIL peptide is stable in cytosolic extracts.

Example 6

The SUMO1 EIL Peptide (SEQ ID NO: 1) Acts as a Selective, Non-competitive, Allosteric Inhibitor of DPP8 and DPP9

The inventors found that pure recombinant DPP8 and DPP9 are inhibited by the EIL peptide, also in the absence of SUMO1 (FIGS. 9A&B). These results show that the inhibition is not due to the dissociation of SUMO1 from DPP9 but rather by the direct interaction between the EIL peptide and DPP8 or DPP9. The pattern of the inhibition kinetics shows that the EIL acts as a non-competitive inhibitor, verifying that it does not target the active site. The K values for DPP8 and DPP9 are 8.4 µM and 7.4 µM respectively. Importantly, DPPIV is not inhibited by the EIL peptide, also in the presence of 13 µM peptide, demonstrating the selective inhibition of DPP8 and DPP9 by the EIL (FIG. 9C).

Example 7

Improved Inhibition: Variants of EIL Peptide

To improve the inhibition of DPP9, the inventors tested several peptide libraries composed of truncated variants of the EIL peptide (>80% pure, ordered from Genescript). These peptides were incubated with recombinant DPP9 and analysed GP-AMC hydrolysis. AMC release was then compared to samples containing either DPP9 alone, or the EIL peptide. The results of this screen are summarized in the table below.

TABLE 1

Inhibition of DPP9 by variants of the EIL. Purified recombinant DPP9 (25 nM) was incubated with 0.2 mM GP-AMC, and 14 µM of the EIL variant peptides. Fluorescence was measured using the Appliskan microplate fluorimeter (Thermo Scientific) with 380 nm (excitation) and 480 nm (emission) filters and the Skanit software.

| | Inhibitory peptide (aa sequence) | % DPP9 activity (Mean) | Std. Deviation |
|---|---|---|---|
| 1. | No peptide | 100 | 4.013 |
| 2. | SLRFLFEGQRIADNH (EIL peptide; SEQ ID NO: 1) | 27.45 | 1.92 |
| 3. | SLRFLFAGQRIADNH (SEQ ID NO: 14) | 5.093 | 0.6078 |
| 4. | SLRFLYEGQRIADNH (SEQ ID NO: 15) | 13.06 | 0.5645 |
| 5. | SLRFLFEGQRIADNR (SEQ ID NO: 16) | 56.38 | 2.135 |
| 6. | SLRFLFDGQRIADNH (SEQ ID NO: 17) | 74.9 | 2.172 |
| 7. | SLRFLWEGQRIADNH (SEQ ID NO: 18) | 26.93 | 1.991 |
| 8. | SLRFLVEGQRIADNH (SEQ ID NO: 19) | 28.61 | 1.223 |

TABLE 1-continued

Inhibition of DPP9 by variants of the EIL. Purified recombinant DPP9 (25 nM) was incubated with 0.2 mM GP-AMC, and 14 µM of the EIL variant peptides. Fluorescence was measured using the Appliskan microplate fluorimeter (Thermo Scientific) with 380 nm (excitation) and 480 nm (emission) filters and the Skanit software.

| | Inhibitory peptide (aa sequence) | % DPP9 activity (Mean) | Std. Deviation |
|---|---|---|---|
| 9. | SLRFLAEGQRIADNH (SEQ ID NO: 21) | 72.87 | 4.704 |
| 10. | SLRFLFEAQRIADNH (SEQ ID NO: 22) | 19.46 | 2.709 |
| 11. | LRFLFEGQRIADNH (SEQ ID NO: 23) | 79.82 | 2.022 |
| 12. | RFLFEGQRIADNH (SEQ ID NO: 24) | 42.7 | 2.16 |
| 13. | LFEGQRIADNH (SEQ ID NO: 25) | 67.77 | 3.627 |
| 14. | FEGQRIADNH (SEQ ID NO: 26) | 97.12 | 1.522 |
| 15. | SLRFLFEGQRIAD (SEQ ID NO: 27) | 29.07 | 0.9588 |
| 16. | SLRFLFEGQRI (SEQ ID NO: 28) | 18.36 | 0.8809 |
| 17. | SLRFLFEGQR (SEQ ID NO: 29) | 24.27 | 0.5411 |
| 18. | SLRFLFEGQ (SEQ ID NO: 30) | 16.43 | 0.5832 |
| 19. | LRFLFEGQRIADN (SEQ ID NO: 31) | 66.42 | 5.493 |
| 20. | RFLFEGQRIAD (SEQ ID NO: 32) | 38.41 | 1.362 |
| 21. | FLFEGQRIA (SEQ ID NO: 33) | 55.93 | 5.38 |
| 22. | FLFEGQRI (SEQ ID NO: 34) | 48.41 | 1.53 |
| 23. | LFEGQR (SEQ ID NO: 35) | 51 | 6.869 |
| 24. | FLIEGQRI (SEQ ID NO: 36) | 49.04 | 2.345 |

The inventors selected three peptides form the library for a more detailed analysis to measure the Ki values of these peptides compared to the EIL peptide, as shown in Table 2 below.

TABLE 2

Inhibition of DPP9 by variants of the EIL.
Purified recombinant DPP9 (25 nM) was incubated
with 0, 5, or 20 µM peptide and tested for the
hydrolysis of GP-AMC (0, 31, 62.5, 125, 250 and
500 µM). Fluorescence was measured using the
Appliskan microplate fluorimeter(Thermo Scientific)
with 380 nm (excitation) and 480 nm (emission
filters and the Skanit software.

| | Inhibitory peptide sequence | $K_i$ (µM) for inhibition of DPP9 |
|---|---|---|
| 1 | SLRFLFEGQRIADNH (EIL; SEQ ID NO: 1) | 7.316 |
| 2 | SLRFLYEGQRIADNH (SEQ ID NO: 15) | 2.557 |
| 3 | SLRFLFAGQRIADNH (SEQ ID NO: 14) | 1.43 |
| 4 | SLRFLFEG (SEQ ID NO: 37) | 2 |

The analysis of the first library shows that (1) the serine residue is important for inhibition; (2) the minimal sequence includes SLRFLFEG (SEQ ID NO: 37); (3) position 6 shall contain a hydrophobic amino acid: Tyr, Phe, Val, Trp, (Ile), replacement by an Ala losses the inhibitory effect (cf. peptide #9 in Table 1; SEQ ID NO: 21); (4) position 7 may be Glu or an Ala, where Ala is more efficient; and (5) position 8 may be Gly or Ala.

In a following library the inventors tested several variations of the SLRFLFEG (SEQ ID NO: 37) sequence, summarized in Table 3.

TABLE 3

Inhibition of DPP9 by variants of the SLRFLFEG
(SEQ ID NO: 37).
Purified recombinant DPP9 (25 nM) was incubated
with 0.2 mM GP-AMC, and 10 µM of the SLRFLFEG
(SEQ ID NO: 37) variant peptides. Fluorescence was
measured using the Appliskan microplate fluorimeter
(Thermo Scientific) with 380 nm (excitation)and 480
nm (emission) filters and the Skanit software.

| | Inhibitory peptide (aa sequence) | % DPP9 activity (Mean) | Std. Deviation |
|---|---|---|---|
| 1. | DPP9 | 100.3 | 8.857 |
| 2. | SLRFLFEG (SEQ ID NO: 37) | 24.08 | 2.275 |
| 3. | SLRFLYEG (SEQ ID NO: 38) | 10.92 | 1.564 |
| 4. | SLRFLFAG (SEQ ID NO: 39) | 15.33 | 1.017 |
| 5. | SLRFLYAG (SEQ ID NO: 40) | 16.27 | 1.535 |
| 6. | TLRFLFEG (SEQ ID NO: 41) | 29.2 | 2.598 |
| 7. | Acet-SLRFLFEG (SEQ ID NO: 42) | 90.74 | 3.223 |
| 8. | Acet-SLRFLYEG (SEQ ID NO: 43) | 89.09 | 1.433 |
| 9. | AAASLRFLYEG (SEQ ID NO: 44) | 91.15 | 4.535 |
| 10. | SLRFLYEGAAA (SEQ ID NO: 45) | 23.86 | 0.1565 |
| 11. | RRRRSLRFLFEG (SEQ ID NO: 46) | 92.2 | 1.984 |
| 12. | RRRRSLRFLYAG (SEQ ID NO: 47) | 91.47 | 2.428 |

The analysis of the second library shows that (1) strongest inhibition was observed for SLRFLYEG (SEQ ID NO: 38); (2) position 1 must contain a free NH3 group (no acetylation), and can be Ser or Thr; (3) position 6 shall contain a hydrophobic amino acid: Tyr, Phe, Val, Trp (Ile); (4) a stretch of Ala starting from position 9 Is tolerated (and may be used as a linker to introduce R residues for enhanced cell penetration).

Peptide SLRFLYEG (SEQ ID NO: 38) was analysed further and was found to have the lowest $k_i$ and highest selectivity towards DPP9 over DPP8: The $K_i$ for DPP9 is 0.4 µM, (18.5 fold increased efficiency compared to the EIL peptide), whereas the $K_i$ for DPP8 is 3.6 µM (the affinity is 9 fold lower compared to DPP9). It has no inhibitory effect towards DPPIV, in the concentrations measured (up to 50 µM).

Example 8

Cytosolic Targeting of Inhibitory Peptides

The inventors tested whether the inhibitory peptides can be inserted into cells. For this purpose the inventors established a method using a well characterized carrier peptide: Peptide 1 (KETWWETWWTEWSQPKKKRKV; SEQ ID NO: 48), in combination with SLRFLYAG (SEQ ID NO: 40). To test for effective inhibition, the inventors measured for hydrolysis of an artificial DPP8 and DPP9 substrate: GP-AMC, specifically in cytosolic extracts. For this, 5 µM or 10 µM of SLRFLYAG (SEQ ID NO: 40) were incubated with 100 µM Peptide 1, at 37° C. for 30 minutes, in 250 ml DMEM without FCS, supplemented with glutamine and antibiotics. Once a complex was formed between the SLRFLYAG (SEQ ID NO: 40) and peptide 1, it was added to HEK293 cells (human embryonic kidney cells), grown in 24 well plates (50% confluence), and incubated for 30 minutes at 37° C. Cells were then trypsinized and washed twice with PBS buffer. Cell pellet was shock frozen in liquid nitrogen. For preparation of cytosolic extracts: cell pellet were resuspended in TB buffer, dounced and centrifuged at 14,000 g. Cytosolic extracts (5 µg) were then tested for the hydrolysis of 500 µM GP-AMC. Fluorescence was measured using the Appliskan microplate fluorimeter (Thermo Scientific) with 380 nm (excitation) and 480 nm (emission) filters and the Skanit software, and analysed using the Prism software.

Importantly, using this setup, the inventors show that the inhibitory peptide SLRFLYAG (SEQ ID NO: 40) can successfully enter the cell and inhibit the cytosolic prolyl peptidase activity by ca 30% using 5 µM SLRFLYAG (SEQ ID NO: 40) peptide (FIG. 11). These results show that the combination of our inhibitory peptides with peptide 1 is indeed an effective tool to insert these inhibitory peptides into cells.

Example 9

SLRFLYEG (SEQ ID NO: 38) is Cell Permeable and Inhibits Cytosolic Prolyl Peptidase Activity To test whether the SLRFLYEG peptide (SEQ ID NO: 38) enters the cells, it was labeled with FITC. 5 µM SLRFLYEG labelled with FITC was allowed to form a complex with the cell-penetrating peptide (Pep-1) in DMEM FCS-free at a molar ratio of 1:10 (cargo:carrier). As a control, a mixture with Peptide-1 alone was used. Complexes were formed for 30 minutes at 37° C. The mixtures were then overlaid onto HeLa cells grown on glass coverslips at a confluence of 60-70%, allowing the complexes to enter the cells for 30 minutes at 37° C. For observation, cells were fixed for 10 minutes with 4% formaldehyde, nuclei were stained with 10 µg/ml Hoechst 33258 (Molecular Probes) and cells were mounted with Fluorescent mounting medium (DAKO). For analysis, cells were imaged using a LSM 510-Meta confocal microscope, oil immersion objective 63×/1.3 (Carl Zeiss MicroImaging, Inc.). The obtained images were processed using the LSM image Browser (Carl Zeiss MicroImaging, Inc.) and Adobe Photoshop.

The resulting images (not shown) demonstrated that HeLa cells treated with Pep-1 in complex with FITC-SLRFLYEG show cellular localization of the FITC-labelled inhibitor, together with Hoechst 33258 nuclear staining. Thus, it could be clearly shown that the peptide enters the cells.

In another experiment, HeLa cells were treated for 30 minutes with either 5 µM SLRFLYEG (SEQ ID NO: 38) alone or in complex with the carier peptide Pep-1. Cells were then typsinized and cytosolic extracts were prepared and tested for cleavage of the model substrate GP-AMC. The results are shown in FIG. 12. Upper panel: SLRFLYEG (SEQ ID NO: 38) was allowed to form a complex with carrier peptide Pep-1 at a molar ratio of 1:10 (cargo:carrier) in FCS free DMEM for 30 min at 37° C. Lower panel: As a comparison, the inhibitory peptide SLRFLYEG was used also in the absence of carrier peptide, at the same concentration. For control, the solvent DMSO was used. These mixtures were overlaid onto HeLa cells allowing the entry for 30 minutes at 37° C. Cells were then trypsinized and lysed in TB buffer containing 0.2% Tween. After ultracentrifugation, the cytosolic extract were probed for DPP activity using 250 mM of the fluorogenic substrate GP-AMC. Each experiment was performed in triplicates.

The results in FIG. 12 show that the SLRFLYEG (SEQ ID NO: 38) peptide enters the cells and inhibits cytosolic prolyl peptidase activity also in the absence of the carrier peptide Pep-1.

Example 10

Cells Exposed to SLRFLYEG (SEQ ID NO: 38) Show Reduced Proliferation

To test whether DPP8/9 inhibition effects cell viability, the inventors performed MTT (3-4,5-dimethylthiazol-2-yl)-2,5-diphenyltetrazolium bromide) based assays, which are widely used to measure cell proliferation and growth (e.g. in clinical settings for testing tumor sensitivity to chemotherapeutic agents). This assay involves the conversion of the water soluble MTT to an insoluble formazan. The formazan is then solubilized in 0.1N HCl. Absorbance is then determined at 570 nm. For a prolonged exposure of cells to the allosteric DPP8/9 inhibitor SLRFLYEG (SEQ ID NO: 38), the inventors cloned the peptide into a mammalian expression vector pEYFP-N1 from Clontech. The peptide inhibitor contains a serine at its amino-termini. Thus, to avoid expression of the peptide with a methionine residue at its amino terminus, it was cloned in frame with ubiquitin. Once expressed in cells, the ubiquitin moiety is cleaved by ubiquitin isopeptidases to release the SLRFLYEG-YFP (SEQ ID NO: 38) construct. A control construct was included that lacked the SLRFLYEG (SEQ ID NO: 38) peptide (Ubiquitin-YFP). HeLa cells were plated in wells of a 96 well plate and transfected with Fugene HD transfection reagent (Promega) following the manufacturer protocols with the following constructs for 32 hours: Ubiquitin (YFP_UBI), Ubiquitin-SLRFLYEG (YFP_UBI_YEG) or mock treated. 32 hours after transfection, cells were analyzed via a standard MTT assay.

Briefly, cell media was removed and replaced by 0.5 mg/ml of MTT reagent. Following 3 hours of incubation at 37° C., the MIT reagent was removed and replaced by 0.1 N HCl. Absorbance was measured with a microplate fluorimeter. Each experiment was performed in triplicates. FIG. 13 shows a representative.

Using this setup the inventors observe a drastic reduction in cell proliferation of at least 50% in Hela cells exposed to the allosteric DPP8/9 inhibitor SLRFLYEG (SEQ ID NO: 38) compared to the control cells transfected with the control plasmid or mock transfected. The results suggest that inhibition of DPP8 and/or DPP9 using the disclosed inhibitors can be used to control cell viability. The HeLa cell line used here is derived from cervical cancer for use in cancer research. Accordingly, it is very likely that the disclosed inhibitors have therapeutic potential for use in oncology.

LIST OF REFERENCES

WO 2011/113895
WO 2005/106487
US 2011/0218142
US 2008/0293618

Abbott C A, Yu D M, Woollatt E, Sutherland G R, McCaughan G W & Gorrell M D (2000) Cloning, expression and chromosomal localization of a novel human dipeptidyl peptidase (DPP) IV homolog, DPP8. Eur J Biochem 267: 6140-6150

Ajami K, Abbott C A, McCaughan G W & Gorrell M D (2004) Dipeptidyl peptidase 9 has two forms, a broad tissue distribution, cytoplasmic localization and DPIV-like peptidase activity. Biochim. Biophys. Acta 1679: 18-28

Baba D, Maita N, Jee J-G, Uchimura Y, Saitoh H, Sugasawa K, Hanaoka F, Tochio H, Hiroaki H & Shirakawa M (2005) Crystal structure of thymine DNA glycosylase conjugated to SUMO-1. Nature 435: 979-982

Bossis G & Melchior F (2006) Regulation of SUMOylation by Reversible Oxidation of SUMO Conjugating Enzymes. Molecular Cell 21: 349-357

Chang C-C, Naik M T, Huang Y-S, Jeng J-C, Liao P-H, Kuo H-Y, Ho C-C, Hsieh Y-L, Lin C-H, Huang N-J, Naik N M, Kung C C-H, Lin S-Y, Chen R-H, Chang K-S, Huang T-H & Shih H-M (2011) Structural and functional roles of Daxx SIM phosphorylation in SUMO paralog-selective binding and apoptosis modulation. Molecular Cell 42: 62-74

Geiss-Friedlander R & Melchior F (2007) Concepts in sumoylation: a decade on. Nat. Rev. Mol. Cell Biol. 8: 947-956

Geiss-Friedlander R, Parmentier N, Möller U, Urlaub H, Van den Eynde B J & Melchior F (2009) The cytoplasmic peptidase DPP9 is rate-limiting for degradation of proline-containing peptides. J. Biol. Chem. 284: 27211-27219

Hannich J T, Lewis A, Kroetz M B, Li S-J, Heide H, Emili A & Hochstrasser M (2005) Defining the SUMO-modified proteome by multiple approaches in *Saccharomyces cerevisiae*. J. Biol. Chem. 280: 4102-4110

Hecker C-M, Rabiller M, Haglund K, Bayer P & Dikic I (2006) Specification of SUMO1- and SUMO2-interacting motifs. J. Biol. Chem. 281: 16117-16127

Knipscheer P, van Dijk W J, Olsen J V, Mann M & Sixma T K (2007) Noncovalent interaction between Ubc9 and SUMO promotes SUMO chain formation. The EMBO Journal 26: 2797-2807

Lu C, Tilan J U, Everhart L, Czarnecka M, Soldin S J, Mendu D R, Jeha D, Hanafy J, Lee C K, Sun J, Izycka-Swieszewska E, Toretsky J A & Kitlinska J (2011) Dipeptidyl peptidases as survival factors in Ewing sarcoma family of tumors: implications for tumor biology and therapy. Journal of Biological Chemistry 286: 27494-27505

Meulmeester E, Kunze M, Hsiao H H, Urlaub H & Melchior F (2008) Mechanism and Consequences for Paralog-Specific Sumoylation of Ubiquitin-Specific Protease 25. Molecular Cell 30: 610-619

Park J, Knott H M, Nadvi N A, Collyer C A, Wang X M, Church W B & Gorrell M D (2008) Reversible Inactivation of Human Dipeptidyl Peptidases 8 and 9 by Oxidation. TOED 1: 52-60

Pichler A, Gast A, Seeler J-S, Dejean A & Melchior F (2002) The nucleoporin RanBP2 has SUMO1 E3 ligase activity. Cell 108: 109-120

Reverter D & Lima C D (2005) Insights into E3 ligase activity revealed by a SUMO-RanGAP1-Ubc9-Nup358 complex. Nature 435: 687-692

Rummey C & Metz G (2006) Homology models of dipeptidyl peptidases 8 and 9 with a focus on loop predictions near the active site. Proteins 66: 160-171

Sauer G, Körner R, Hanisch A, Ries A, Nigg E A & Silljé H H W (2005) Proteome analysis of the human mitotic spindle. Mol. Cell Proteomics 4: 35-43

Schade J, Stephan M, Schmiedl A, Wagner L, Niestroj A J, Demuth H-U, Frerker N, Klemann C, Raber K A, Pabst R & Hörsten von S (2008) Regulation of expression and function of dipeptidyl peptidase 4 (DP4), DP8/9, and DP10 in allergic responses of the lung in rats. J. Histochem. Cytochem. 56: 147-155

Song J, Durrin L K, Wilkinson T A, Krontiris T G & Chen Y (2004) Identification of a SUMO-binding motif that recognizes SUMO-modified proteins. Proc. Natl. Acad. Sci. U.S.A. 101: 14373-14378

Tang H-K, Chen K-C, Liou G-G, Cheng S-C, Chien C-H, Tang H-Y, Huang L-H, Chang H-P, Chou C-Y & Chen X (2011) Role of a propeller loop in the quaternary structure and enzymatic activity of prolyl dipeptidases DPP-IV and DPP9. FEBS Letters 585: 3409-3414

Tang H-K, Tang H-Y, Hsu S-C, Chu Y-R, Chien C-H, Shu C-H & Chen X (2009) Biochemical properties and expression profile of human prolyl dipeptidase DPP9. Archives of Biochemistry and Biophysics 485: 120-127

Van Goethem S, Matheeussen V, Joossens J, Lambeir A-M, Chen X, De Meester I, Haemers A, Augustyns K & Van der Veken P (2011) Structure-Activity Relationship Studies on Isoindoline Inhibitors of Dipeptidyl Peptidases 8 and 9 (DPP8, DPP9): Is DPP8-Selectivity an Attainable Goal? J. Med. Chem. 54: 5737-5746

Yao T-W, Kim W-S, Yu D M, Sharbeen G, McCaughan G W, Choi K-Y, Xia P & Gorrell M D (2011) A Novel Role of Dipeptidyl Peptidase 9 in Epidermal Growth Factor Signaling. Mol Cancer Res Yu D M T, Ajami K, Gall M G, Park J, Lee C S, Evans K A, McLaughlin E A, Pitman M R, Abbott C A, McCaughan G W & Gorrell M D (2009) The in vivo expression of dipeptidyl peptidases 8 and 9. J. Histochem. Cytochem. 57: 1025-1040

Yu D M T, Wang X M, McCaughan G W & Gorrell M D (2006) Extraenzymatic functions of the dipeptidyl peptidase IV-related proteins DP8 and DP9 in cell adhesion, migration and apoptosis. FEBS Journal 273: 2447-2460

Zhang H, Chen Y, Keane F M (2013) Advances in Understanding the Expression and Function of Dipeptidyl Peptidase 8 and 9. Molecular Cancver Research (published online 13 Sep. 2013).

The invention claimed is:

1. A peptide of 8 to 20 amino acids length, comprising the N-terminal sequence
Xaa$_1$-Leu-Arg-Phe-Leu-Xaa$_6$-Xaa$_7$-Xaa$_8$,
wherein Xaa$_1$ is selected from Ser and Thr,
wherein Xaa$_6$ is selected from Phe, Tyr, Trp, Val and Ile,
wherein Xaa$_7$ is selected from Ala and Glu, and
wherein Xaa$_8$ is selected from Gly and Ala (SEQ ID NO: 48);
with the proviso that if Xaa$_6$ is Phe, then Xaa$_7$ is Ala or Xaa$_1$ is Thr;
wherein the peptide is a non-competitive allosteric inhibitor of a dipeptidyl peptidase selected from DPP9, DPP8, and a combination of DPP8 and DPP9.

2. The peptide of claim 1, having (i) a K$_i$ for DPP9 of 0.4-10 µM; or (ii) a K$_i$ for DPP8 of 3.6 to 12 µM; or (iii) a K$_i$ for DPP9 of 0.4-10 µM and a K$_i$ for DPP8 of 3.6 to 12 µM.

3. The peptide of claim 1, wherein the peptide is capable of inhibiting the activity by wild-type DPP9 (SEQ ID NO: 6) to a level of 35 to 5% of the activity if not inhibited, as determined in an assay using 25 nM DPP9, 0.2 mM GP-AMC, and 14 µM of the peptide to be tested, in TB buffer (20 mM Hepes/KOH pH 7.3, 110 mM potassium acetate, 2 mM Mg acetate, 0.5 mM EGTA), supplemented with 0.2% polyoxyethylene (20) sorbitan monolaurate, 1 mM dithiothreitol, 380 nm excitation and 480 nm emission.

4. The peptide of claim 1, which has no inhibitory effect towards DPPIV (SEQ ID NO:8) as determined in an assay using 25 nM DPPIV, 0.2 mM GP-AMC, and 14 µM of the peptide to be tested, in TB buffer (20 mM Hepes/KOH pH 7.3, 110 mM potassium acetate, 2 mM Mg acetate, 0.5 mM EGTA), supplemented with 0.2% polyoxyethylene (20) sorbitan monolaurate, 1 mM dithiothreitol, 380 nm excitation and 480 nm emission.

5. The peptide of claim 1, wherein positions 9 to 20 comprise a stretch of one, two or three Ala-residues followed by 5-9 Arg-residues for improving cell penetration of the peptide.

6. The peptide of claim 1, wherein positions 9 to 20 comprise 5-9 Arg-residues for improving cell penetration of the peptide.

7. The peptide of claim 1 having one of the amino acid sequences as shown in SEQ ID NO: 14, 38, 15, 39, 40, 28, 37, 29, 18, 1, 19, 27, or 41.

8. A polypeptide, comprising, fused to the N-terminus, a peptide of 8 to 20 amino acids length, comprising the N-terminal sequence Xaa$_1$-Leu-Arg-Phe-Leu-Xaa$_6$-Xaa$_7$-Xaa$_8$,
wherein Xaa$_1$ is selected from Ser and Thr,
wherein Xaa$_6$ is selected from Phe, Tyr, Trp, Val and Ile,
wherein Xaa$_7$ is selected from Ala and Glu, and
wherein Xaa$_8$ is selected from Gly and Ala (SEQ ID NO: 48);
with the proviso that if Xaa$_6$ is Phe, then Xaa$_7$ is Ala or Xaa$_1$ is Thr;
wherein the peptide is a non-competitive allosteric inhibitor of a dipeptidyl peptidase selected from DPP9, DPP8, and a combination of DPP8 and DPP9.

9. A peptide having the sequence Val-Glu-Xaa$_3$-Ile-His-Val-Xaa$_7$-Ser-Pro-Xaa$_{10}$-Leu-Glu-Xaa$_{13}$-Arg-Xaa$_{15}$-Xaa$_{16}$-Asp-Ser-Xaa$_{19}$-Arg,
wherein Xaa$_3$ is any amino acid other than Val or Ile,
wherein Xaa$_7$ is selected from Pro and Thr,
wherein Xaa$_{10}$ is selected from Ala and Met,
wherein Xaa$_{13}$ is selected from Glu and Thr,
wherein Xaa$_{15}$ is selected from Lys and Arg,
wherein Xaa$_{16}$ is selected from Thr and Ala, and
wherein Xaa$_{19}$ is selected from Tyr and Phe, as represented by SEQ ID NO: 49,
wherein the peptide competitively inhibits binding to the E67-interacting loop (EIL) of SUMO-1.

10. A polypeptide comprising
a peptide having the sequence
Val-Glu-Xaa$_3$-Ile-His-Val-Xaa$_7$-Ser-Pro-Xaa$_{10}$-Leu-Glu-Xaa$_{13}$-Arg-Xaa$_{15}$-Xaa$_{16}$-Asp-Ser-Xaa$_{19}$-Arg,
wherein Xaa$_3$ is any amino acid other than Val or Ile,
wherein Xaa$_7$ is selected from Pro and Thr,
wherein Xaa$_{10}$ is selected from Ala and Met,
wherein Xaa$_{13}$ is selected from Glu and Thr,
wherein Xaa$_{15}$ is selected from Lys and Arg,
wherein Xaa$_{16}$ is selected from Thr and Ala, and
wherein Xaa$_{19}$ is selected from Tyr and Phe, as represented by SEQ ID NO: 49,
wherein the peptide competitively inhibits binding to the E67-interacting loop (EIL) of SUMO-1; and
wherein the polypeptide is not DPP8 or DPP9.

11. A method for the treatment of cancer, comprising the step of administering to a subject in need thereof a pharmaceutical composition comprising (i) a peptide of 8 to 20 amino acids length, comprising the N-terminal sequence
Xaa$_1$-Leu-Arg-Phe-Leu-Xaa$_6$-Xaa$_7$-Xaa$_8$,
wherein Xaa$_1$ is selected from Ser and Thr,
wherein Xaa$_6$ is selected from Phe, Tyr, Trp, Val and Ile,
wherein Xaa$_7$ is selected from Ala and Glu, and wherein Xaa$_8$ is selected from Gly and Ala (SEQ ID NO: 48), with the proviso that if Xaa$_6$ is Phe, then Xaa$_7$ is Ala or Xaa$_1$ is Thr, wherein the peptide is a non-competitive allosteric inhibitor of a dipeptidyl peptidase selected from DPP9, DPP8, and a combination of DPP8 and DPP9; or (ii) a polypeptide, comprising, fused to the N-terminus, the peptide according to (i); and a pharmaceutically acceptable carrier, excipient or diluent.

12. The method of claim 11, wherein the cancer is selected from cervical cancer, melanoma, chronic myelogenous leukemia, colorectal adenocarcinoma, neuroblastoma, testicular tumors, breast cancer, ovarian cancer, and/or B cell chronic lymphocytic leukemia.

13. The method of claim 11, wherein the subject is a mammal.

14. The method of claim 11, wherein the subject is a horse, cow, pig, mouse, rat, guinea pig, cat, dog, goat, sheep, or non-human primate.

15. The method of claim 11, wherein the subject is a human.

16. The peptide of claim 1, wherein the amino acid residue at position 1 contains a free amino-terminus.

17. The polypeptide of claim 8, wherein wherein the amino acid residue at position 1 contains a free amino-terminus.

* * * * *

SEQUENCE LISTING

```
<160> NUMBER OF SEQ ID NOS: 49

<210> SEQ ID NO 1
<211> LENGTH: 15
<212> TYPE: PRT
<213> ORGANISM: Artificial
<220> FEATURE:
<223> OTHER INFORMATION: SUMO1 Peptide 9

<400> SEQUENCE: 1

Ser Leu Arg Phe Leu Phe Glu Gly Gln Arg Ile Ala Asp Asn His
1               5                   10                  15

<210> SEQ ID NO 2
<211> LENGTH: 15
<212> TYPE: PRT
<213> ORGANISM: Artificial
<220> FEATURE:
<223> OTHER INFORMATION: SUMO2/SUMO3 corresponding sequence to SUMO1
      Peptide 9

<400> SEQUENCE: 2

Gln Ile Arg Phe Arg Phe Asp Gly Gln Pro Ile Asn Glu Thr Asp
1               5                   10                  15

<210> SEQ ID NO 3
<211> LENGTH: 21
<212> TYPE: PRT
<213> ORGANISM: Artificial
<220> FEATURE:
```

<223> OTHER INFORMATION: DDP9 arm motif

<400> SEQUENCE: 3

Val Glu Val Ile His Val Pro Ser Pro Ala Leu Glu Glu Arg Lys Thr
1               5                   10                  15

Asp Ser Tyr Arg Tyr
            20

<210> SEQ ID NO 4
<211> LENGTH: 21
<212> TYPE: PRT
<213> ORGANISM: Artificial
<220> FEATURE:
<223> OTHER INFORMATION: DPP8 arm motif

<400> SEQUENCE: 4

Val Glu Ile Ile His Val Thr Ser Pro Met Leu Glu Thr Arg Arg Ala
1               5                   10                  15

Asp Ser Phe Arg Tyr
            20

<210> SEQ ID NO 5
<211> LENGTH: 20
<212> TYPE: PRT
<213> ORGANISM: Artificial
<220> FEATURE:
<223> OTHER INFORMATION: DPP4 arm motif

<400> SEQUENCE: 5

Ile Glu Tyr Ser Phe Tyr Ser Asp Glu Ser Leu Gln Tyr Pro Lys Thr
1               5                   10                  15

Val Arg Val Pro
            20

<210> SEQ ID NO 6
<211> LENGTH: 892
<212> TYPE: PRT
<213> ORGANISM: Homo sapiens

<400> SEQUENCE: 6

Met Arg Lys Val Lys Lys Leu Arg Leu Asp Lys Glu Asn Thr Gly Ser
1               5                   10                  15

Trp Arg Ser Phe Ser Leu Asn Ser Glu Gly Ala Glu Arg Met Ala Thr
                20                  25                  30

Thr Gly Thr Pro Thr Ala Asp Arg Gly Asp Ala Ala Thr Asp Asp Asp
            35                  40                  45

Pro Ala Ala Arg Phe Gln Val Gln Lys His Ser Trp Asp Gly Leu Arg
        50                  55                  60

Ser Ile Ile His Gly Ser Arg Lys Tyr Ser Gly Leu Ile Val Asn Lys
65                  70                  75                  80

Ala Pro His Asp Phe Gln Phe Val Gln Lys Thr Asp Glu Ser Gly Pro
                85                  90                  95

His Ser His Arg Leu Tyr Tyr Leu Gly Met Pro Tyr Gly Ser Arg Glu
            100                 105                 110

Asn Ser Leu Leu Tyr Ser Glu Ile Pro Lys Lys Val Arg Lys Glu Ala
        115                 120                 125

Leu Leu Leu Leu Ser Trp Lys Gln Met Leu Asp His Phe Gln Ala Thr
    130                 135                 140

Pro His His Gly Val Tyr Ser Arg Glu Glu Leu Leu Arg Glu Arg
145                 150                 155                 160

-continued

Lys Arg Leu Gly Val Phe Gly Ile Thr Ser Tyr Asp Phe His Ser Glu
                165                 170                 175

Ser Gly Leu Phe Leu Phe Gln Ala Ser Asn Ser Leu Phe His Cys Arg
            180                 185                 190

Asp Gly Gly Lys Asn Gly Phe Met Val Ser Pro Met Lys Pro Leu Glu
            195                 200                 205

Ile Lys Thr Gln Cys Ser Gly Pro Arg Met Asp Pro Lys Ile Cys Pro
        210                 215                 220

Ala Asp Pro Ala Phe Phe Ser Phe Ile Asn Asn Ser Asp Leu Trp Val
225                 230                 235                 240

Ala Asn Ile Glu Thr Gly Glu Glu Arg Arg Leu Thr Phe Cys His Gln
                245                 250                 255

Gly Leu Ser Asn Val Leu Asp Asp Pro Lys Ser Ala Gly Val Ala Thr
            260                 265                 270

Phe Val Ile Gln Glu Glu Phe Asp Arg Phe Thr Gly Tyr Trp Trp Cys
            275                 280                 285

Pro Thr Ala Ser Trp Glu Gly Ser Glu Gly Leu Lys Thr Leu Arg Ile
        290                 295                 300

Leu Tyr Glu Glu Val Asp Glu Ser Glu Val Glu Val Ile His Val Pro
305                 310                 315                 320

Ser Pro Ala Leu Glu Glu Arg Lys Thr Asp Ser Tyr Arg Tyr Pro Arg
                325                 330                 335

Thr Gly Ser Lys Asn Pro Lys Ile Ala Leu Lys Leu Ala Glu Phe Gln
            340                 345                 350

Thr Asp Ser Gln Gly Lys Ile Val Ser Thr Gln Glu Lys Glu Leu Val
            355                 360                 365

Gln Pro Phe Ser Ser Leu Phe Pro Lys Val Glu Tyr Ile Ala Arg Ala
        370                 375                 380

Gly Trp Thr Arg Asp Gly Lys Tyr Ala Trp Ala Met Phe Leu Asp Arg
385                 390                 395                 400

Pro Gln Gln Trp Leu Gln Leu Val Leu Leu Pro Pro Ala Leu Phe Ile
                405                 410                 415

Pro Ser Thr Glu Asn Glu Glu Gln Arg Leu Ala Ser Ala Arg Ala Val
            420                 425                 430

Pro Arg Asn Val Gln Pro Tyr Val Val Tyr Glu Glu Val Thr Asn Val
            435                 440                 445

Trp Ile Asn Val His Asp Ile Phe Tyr Pro Phe Pro Gln Ser Glu Gly
        450                 455                 460

Glu Asp Glu Leu Cys Phe Leu Arg Ala Asn Glu Cys Lys Thr Gly Phe
465                 470                 475                 480

Cys His Leu Tyr Lys Val Thr Ala Val Leu Lys Ser Gln Gly Tyr Asp
                485                 490                 495

Trp Ser Glu Pro Phe Ser Pro Gly Glu Asp Glu Phe Lys Cys Pro Ile
            500                 505                 510

Lys Glu Glu Ile Ala Leu Thr Ser Gly Glu Trp Glu Val Leu Ala Arg
            515                 520                 525

His Gly Ser Lys Ile Trp Val Asn Glu Glu Thr Lys Leu Val Tyr Phe
        530                 535                 540

Gln Gly Thr Lys Asp Thr Pro Leu Glu His His Leu Tyr Val Val Ser
545                 550                 555                 560

Tyr Glu Ala Ala Gly Glu Ile Val Arg Leu Thr Thr Pro Gly Phe Ser
                565                 570                 575

-continued

His Ser Cys Ser Met Ser Gln Asn Phe Asp Met Phe Val Ser His Tyr
            580                 585                 590

Ser Ser Val Ser Thr Pro Pro Cys Val His Val Tyr Lys Leu Ser Gly
        595                 600                 605

Pro Asp Asp Pro Leu His Lys Gln Pro Arg Phe Trp Ala Ser Met
610                 615                 620

Met Glu Ala Ala Ser Cys Pro Pro Asp Tyr Val Pro Pro Glu Ile Phe
625                 630                 635                 640

His Phe His Thr Arg Ser Asp Val Arg Leu Tyr Gly Met Ile Tyr Lys
                645                 650                 655

Pro His Ala Leu Gln Pro Gly Lys Lys His Pro Thr Val Leu Phe Val
            660                 665                 670

Tyr Gly Gly Pro Gln Val Gln Leu Val Asn Asn Ser Phe Lys Gly Ile
        675                 680                 685

Lys Tyr Leu Arg Leu Asn Thr Leu Ala Ser Leu Gly Tyr Ala Val Val
    690                 695                 700

Val Ile Asp Gly Arg Gly Ser Cys Gln Arg Gly Leu Arg Phe Glu Gly
705                 710                 715                 720

Ala Leu Lys Asn Gln Met Gly Gln Val Glu Ile Glu Asp Gln Val Glu
                725                 730                 735

Gly Leu Gln Phe Val Ala Glu Lys Tyr Gly Phe Ile Asp Leu Ser Arg
            740                 745                 750

Val Ala Ile His Gly Trp Ser Tyr Gly Gly Phe Leu Ser Leu Met Gly
        755                 760                 765

Leu Ile His Lys Pro Gln Val Phe Lys Val Ala Ile Ala Gly Ala Pro
    770                 775                 780

Val Thr Val Trp Met Ala Tyr Asp Thr Gly Tyr Thr Glu Arg Tyr Met
785                 790                 795                 800

Asp Val Pro Glu Asn Asn Gln His Gly Tyr Glu Ala Gly Ser Val Ala
                805                 810                 815

Leu His Val Glu Lys Leu Pro Asn Glu Pro Asn Arg Leu Leu Ile Leu
            820                 825                 830

His Gly Phe Leu Asp Glu Asn Val His Phe Phe His Thr Asn Phe Leu
        835                 840                 845

Val Ser Gln Leu Ile Arg Ala Gly Lys Pro Tyr Gln Leu Gln Ile Tyr
    850                 855                 860

Pro Asn Glu Arg His Ser Ile Arg Cys Pro Glu Ser Gly Glu His Tyr
865                 870                 875                 880

Glu Val Thr Leu Leu His Phe Leu Gln Glu Tyr Leu
                885                 890

<210> SEQ ID NO 7
<211> LENGTH: 898
<212> TYPE: PRT
<213> ORGANISM: Homosapiens

<400> SEQUENCE: 7

Met Trp Lys Arg Ser Glu Gln Met Lys Ile Lys Ser Gly Lys Cys Asn
1               5                   10                  15

Met Ala Ala Ala Met Glu Thr Glu Gln Leu Gly Val Glu Ile Phe Glu
            20                  25                  30

Thr Ala Asp Cys Glu Glu Asn Ile Glu Ser Gln Asp Arg Pro Lys Leu
        35                  40                  45

Glu Pro Phe Tyr Val Glu Arg Tyr Ser Trp Ser Gln Leu Lys Lys Leu
    50                  55                  60

```
Leu Ala Asp Thr Arg Lys Tyr His Gly Tyr Met Met Ala Lys Ala Pro
 65                  70                  75                  80

His Asp Phe Met Phe Val Lys Arg Asn Asp Pro Asp Gly Pro His Ser
             85                  90                  95

Asp Arg Ile Tyr Tyr Leu Ala Met Ser Gly Glu Asn Arg Glu Asn Thr
        100                 105                 110

Leu Phe Tyr Ser Glu Ile Pro Lys Thr Ile Asn Arg Ala Ala Val Leu
    115                 120                 125

Met Leu Ser Trp Lys Pro Leu Leu Asp Leu Phe Gln Ala Thr Leu Asp
130                 135                 140

Tyr Gly Met Tyr Ser Arg Glu Glu Leu Leu Arg Glu Arg Lys Arg
145                 150                 155                 160

Ile Gly Thr Val Gly Ile Ala Ser Tyr Asp Tyr His Gln Gly Ser Gly
                165                 170                 175

Thr Phe Leu Phe Gln Ala Gly Ser Gly Ile Tyr His Val Lys Asp Gly
            180                 185                 190

Gly Pro Gln Gly Phe Thr Gln Gln Pro Leu Arg Pro Asn Leu Val Glu
        195                 200                 205

Thr Ser Cys Pro Asn Ile Arg Met Asp Pro Lys Leu Cys Pro Ala Asp
    210                 215                 220

Pro Asp Trp Ile Ala Phe Ile His Ser Asn Asp Ile Trp Ile Ser Asn
225                 230                 235                 240

Ile Val Thr Arg Glu Glu Arg Arg Leu Thr Tyr Val His Asn Glu Leu
                245                 250                 255

Ala Asn Met Glu Glu Asp Ala Arg Ser Ala Gly Val Ala Thr Phe Val
            260                 265                 270

Leu Gln Glu Glu Phe Asp Arg Tyr Ser Gly Tyr Trp Trp Cys Pro Lys
        275                 280                 285

Ala Glu Thr Thr Pro Ser Gly Gly Lys Ile Leu Arg Ile Leu Tyr Glu
    290                 295                 300

Glu Asn Asp Glu Ser Glu Val Glu Ile Ile His Val Thr Ser Pro Met
305                 310                 315                 320

Leu Glu Thr Arg Arg Ala Asp Ser Phe Arg Tyr Pro Lys Thr Gly Thr
                325                 330                 335

Ala Asn Pro Lys Val Thr Phe Lys Met Ser Glu Ile Met Ile Asp Ala
            340                 345                 350

Glu Gly Arg Ile Ile Asp Val Ile Asp Lys Glu Leu Ile Gln Pro Phe
        355                 360                 365

Glu Ile Leu Phe Glu Gly Val Glu Tyr Ile Ala Arg Ala Gly Trp Thr
    370                 375                 380

Pro Glu Gly Lys Tyr Ala Trp Ser Ile Leu Leu Asp Arg Ser Gln Thr
385                 390                 395                 400

Arg Leu Gln Ile Val Leu Ile Ser Pro Glu Leu Phe Ile Pro Val Glu
                405                 410                 415

Asp Asp Val Met Glu Arg Gln Arg Leu Ile Glu Ser Val Pro Asp Ser
            420                 425                 430

Val Thr Pro Leu Ile Ile Tyr Glu Glu Thr Thr Asp Ile Trp Ile Asn
        435                 440                 445

Ile His Asp Ile Phe His Val Phe Pro Gln Ser His Glu Glu Glu Ile
    450                 455                 460

Glu Phe Ile Phe Ala Ser Glu Cys Lys Thr Gly Phe Arg His Leu Tyr
465                 470                 475                 480
```

```
Lys Ile Thr Ser Ile Leu Lys Glu Ser Lys Tyr Lys Arg Ser Ser Gly
                485                 490                 495

Gly Leu Pro Ala Pro Ser Asp Phe Lys Cys Pro Ile Lys Glu Glu Ile
            500                 505                 510

Ala Ile Thr Ser Gly Glu Trp Glu Val Leu Gly Arg His Gly Ser Asn
            515                 520                 525

Ile Gln Val Asp Glu Val Arg Arg Leu Val Tyr Phe Glu Gly Thr Lys
            530                 535                 540

Asp Ser Pro Leu Glu His His Leu Tyr Val Val Ser Tyr Val Asn Pro
545                 550                 555                 560

Gly Glu Val Thr Arg Leu Thr Asp Arg Gly Tyr Ser His Ser Cys Cys
                565                 570                 575

Ile Ser Gln His Cys Asp Phe Phe Ile Ser Lys Tyr Ser Asn Gln Lys
                580                 585                 590

Asn Pro His Cys Val Ser Leu Tyr Lys Leu Ser Ser Pro Glu Asp Asp
            595                 600                 605

Pro Thr Cys Lys Thr Lys Glu Phe Trp Ala Thr Ile Leu Asp Ser Ala
            610                 615                 620

Gly Pro Leu Pro Asp Tyr Thr Pro Pro Glu Ile Phe Ser Phe Glu Ser
625                 630                 635                 640

Thr Thr Gly Phe Thr Leu Tyr Gly Met Leu Tyr Lys Pro His Asp Leu
                645                 650                 655

Gln Pro Gly Lys Lys Tyr Pro Thr Val Leu Phe Ile Tyr Gly Gly Pro
                660                 665                 670

Gln Val Gln Leu Val Asn Asn Arg Phe Lys Gly Val Lys Tyr Phe Arg
                675                 680                 685

Leu Asn Thr Leu Ala Ser Leu Gly Tyr Val Val Val Ile Asp Asn
            690                 695                 700

Arg Gly Ser Cys His Arg Gly Leu Lys Phe Glu Gly Ala Phe Lys Tyr
705                 710                 715                 720

Lys Met Gly Gln Ile Glu Ile Asp Asp Gln Val Glu Gly Leu Gln Tyr
                725                 730                 735

Leu Ala Ser Arg Tyr Asp Phe Ile Asp Leu Asp Arg Val Gly Ile His
            740                 745                 750

Gly Trp Ser Tyr Gly Gly Tyr Leu Ser Leu Met Ala Leu Met Gln Arg
            755                 760                 765

Ser Asp Ile Phe Arg Val Ala Ile Ala Gly Ala Pro Val Thr Leu Trp
770                 775                 780

Ile Phe Tyr Asp Thr Gly Tyr Thr Glu Arg Tyr Met Gly His Pro Asp
785                 790                 795                 800

Gln Asn Glu Gln Gly Tyr Tyr Leu Gly Ser Val Ala Met Gln Ala Glu
                805                 810                 815

Lys Phe Pro Ser Glu Pro Asn Arg Leu Leu Leu Leu His Gly Phe Leu
            820                 825                 830

Asp Glu Asn Val His Phe Ala His Thr Ser Ile Leu Leu Ser Phe Leu
            835                 840                 845

Val Arg Ala Gly Lys Pro Tyr Asp Leu Gln Ile Tyr Pro Gln Glu Arg
850                 855                 860

His Ser Ile Arg Val Pro Glu Ser Gly Glu His Tyr Glu Leu His Leu
865                 870                 875                 880

Leu His Tyr Leu Gln Glu Asn Leu Gly Ser Arg Ile Ala Ala Leu Lys
                885                 890                 895

Val Ile
```

<210> SEQ ID NO 8
<211> LENGTH: 766
<212> TYPE: PRT
<213> ORGANISM: Homo sapiens

<400> SEQUENCE: 8

```
Met Lys Thr Pro Trp Lys Val Leu Leu Gly Leu Leu Ala Ala Ala
1               5                   10                  15

Leu Val Thr Ile Ile Thr Val Pro Val Val Leu Leu Asn Lys Gly Thr
            20                  25                  30

Asp Asp Ala Thr Ala Asp Ser Arg Lys Thr Tyr Thr Leu Thr Asp Tyr
        35                  40                  45

Leu Lys Asn Thr Tyr Arg Leu Lys Leu Tyr Ser Leu Arg Trp Ile Ser
50                  55                  60

Asp His Glu Tyr Leu Tyr Lys Gln Glu Asn Asn Ile Leu Val Phe Asn
65                  70                  75                  80

Ala Glu Tyr Gly Asn Ser Ser Val Phe Leu Glu Asn Ser Thr Phe Asp
                85                  90                  95

Glu Phe Gly His Ser Ile Asn Asp Tyr Ser Ile Ser Pro Asp Gly Gln
            100                 105                 110

Phe Ile Leu Leu Glu Tyr Asn Tyr Val Lys Gln Trp Arg His Ser Tyr
        115                 120                 125

Thr Ala Ser Tyr Asp Ile Tyr Asp Leu Asn Lys Arg Gln Leu Ile Thr
    130                 135                 140

Glu Glu Arg Ile Pro Asn Asn Thr Gln Trp Val Thr Trp Ser Pro Val
145                 150                 155                 160

Gly His Lys Leu Ala Tyr Val Trp Asn Asn Asp Ile Tyr Val Lys Ile
                165                 170                 175

Glu Pro Asn Leu Pro Ser Tyr Arg Ile Thr Trp Thr Gly Lys Glu Asp
            180                 185                 190

Ile Ile Tyr Asn Gly Ile Thr Asp Trp Val Tyr Glu Glu Glu Val Phe
        195                 200                 205

Ser Ala Tyr Ser Ala Leu Trp Trp Ser Pro Asn Gly Thr Phe Leu Ala
    210                 215                 220

Tyr Ala Gln Phe Asn Asp Thr Glu Val Pro Leu Ile Glu Tyr Ser Phe
225                 230                 235                 240

Tyr Ser Asp Glu Ser Leu Gln Tyr Pro Lys Thr Val Arg Val Pro Tyr
                245                 250                 255

Pro Lys Ala Gly Ala Val Asn Pro Thr Val Lys Phe Phe Val Val Asn
            260                 265                 270

Thr Asp Ser Leu Ser Ser Val Thr Asn Ala Thr Ser Ile Gln Ile Thr
        275                 280                 285

Ala Pro Ala Ser Met Leu Ile Gly Asp His Tyr Leu Cys Asp Val Thr
    290                 295                 300

Trp Ala Thr Gln Glu Arg Ile Ser Leu Gln Trp Leu Arg Arg Ile Gln
305                 310                 315                 320

Asn Tyr Ser Val Met Asp Ile Cys Asp Tyr Asp Glu Ser Ser Gly Arg
                325                 330                 335

Trp Asn Cys Leu Val Ala Arg Gln His Ile Glu Met Ser Thr Thr Gly
            340                 345                 350

Trp Val Gly Arg Phe Arg Pro Ser Glu Pro His Phe Thr Leu Asp Gly
        355                 360                 365

Asn Ser Phe Tyr Lys Ile Ile Ser Asn Glu Glu Gly Tyr Arg His Ile
```

```
              370                 375                 380
Cys Tyr Phe Gln Ile Asp Lys Lys Asp Cys Thr Phe Ile Thr Lys Gly
385                 390                 395                 400

Thr Trp Glu Val Ile Gly Ile Glu Ala Leu Thr Ser Asp Tyr Leu Tyr
                405                 410                 415

Tyr Ile Ser Asn Glu Tyr Lys Gly Met Pro Gly Arg Asn Leu Tyr
            420                 425                 430

Lys Ile Gln Leu Ser Asp Tyr Thr Lys Val Thr Cys Leu Ser Cys Glu
            435                 440                 445

Leu Asn Pro Glu Arg Cys Gln Tyr Tyr Ser Val Ser Phe Ser Lys Glu
            450                 455                 460

Ala Lys Tyr Tyr Gln Leu Arg Cys Ser Gly Pro Gly Leu Pro Leu Tyr
465                 470                 475                 480

Thr Leu His Ser Ser Val Asn Asp Lys Gly Leu Arg Val Leu Glu Asp
                485                 490                 495

Asn Ser Ala Leu Asp Lys Met Leu Gln Asn Val Gln Met Pro Ser Lys
            500                 505                 510

Lys Leu Asp Phe Ile Ile Leu Asn Glu Thr Lys Phe Trp Tyr Gln Met
            515                 520                 525

Ile Leu Pro Pro His Phe Asp Lys Ser Lys Lys Tyr Pro Leu Leu Leu
            530                 535                 540

Asp Val Tyr Ala Gly Pro Cys Ser Gln Lys Ala Asp Thr Val Phe Arg
545                 550                 555                 560

Leu Asn Trp Ala Thr Tyr Leu Ala Ser Thr Glu Asn Ile Ile Val Ala
                565                 570                 575

Ser Phe Asp Gly Arg Gly Ser Gly Tyr Gln Gly Asp Lys Ile Met His
            580                 585                 590

Ala Ile Asn Arg Arg Leu Gly Thr Phe Glu Val Glu Asp Gln Ile Glu
            595                 600                 605

Ala Ala Arg Gln Phe Ser Lys Met Gly Phe Val Asp Asn Lys Arg Ile
            610                 615                 620

Ala Ile Trp Gly Trp Ser Tyr Gly Gly Tyr Val Thr Ser Met Val Leu
625                 630                 635                 640

Gly Ser Gly Ser Gly Val Phe Lys Cys Gly Ile Ala Val Ala Pro Val
                645                 650                 655

Ser Arg Trp Glu Tyr Tyr Asp Ser Val Tyr Thr Glu Arg Tyr Met Gly
            660                 665                 670

Leu Pro Thr Pro Glu Asp Asn Leu Asp His Tyr Arg Asn Ser Thr Val
            675                 680                 685

Met Ser Arg Ala Glu Asn Phe Lys Gln Val Glu Tyr Leu Leu Ile His
            690                 695                 700

Gly Thr Ala Asp Asp Asn Val His Phe Gln Ser Ala Gln Ile Ser
705                 710                 715                 720

Lys Ala Leu Val Asp Val Gly Val Asp Phe Gln Ala Met Trp Tyr Thr
                725                 730                 735

Asp Glu Asp His Gly Ile Ala Ser Ser Thr Ala His Gln His Ile Tyr
            740                 745                 750

Thr His Met Ser His Phe Ile Lys Gln Cys Phe Ser Leu Pro
            755                 760                 765

<210> SEQ ID NO 9
<211> LENGTH: 25
<212> TYPE: RNA
<213> ORGANISM: Artificial
```

-continued

```
<220> FEATURE:
<223> OTHER INFORMATION: SUMO1-i

<400> SEQUENCE: 9
ggauagcagu gagauucacu ucaaa                                              25

<210> SEQ ID NO 10
<211> LENGTH: 25
<212> TYPE: RNA
<213> ORGANISM: Artificial
<220> FEATURE:
<223> OTHER INFORMATION: SUMO1-ii

<400> SEQUENCE: 10
ggaagaagau gugauugaag uuuau                                              25

<210> SEQ ID NO 11
<211> LENGTH: 20
<212> TYPE: PRT
<213> ORGANISM: Homo sapiens

<400> SEQUENCE: 11

Val Glu Val Ile His Val Pro Ser Pro Ala Leu Glu Glu Arg Lys Thr
1               5                   10                  15

Asp Ser Tyr Arg
            20

<210> SEQ ID NO 12
<211> LENGTH: 30
<212> TYPE: PRT
<213> ORGANISM: Homo sapiens

<400> SEQUENCE: 12

Leu Tyr Glu Glu Val Asp Glu Ser Glu Val Glu Val Ile His Val Pro
1               5                   10                  15

Ser Pro Ala Leu Glu Glu Arg Lys Thr Asp Ser Tyr Arg Tyr
            20                  25                  30

<210> SEQ ID NO 13
<211> LENGTH: 30
<212> TYPE: PRT
<213> ORGANISM: Homo sapiens

<400> SEQUENCE: 13

Leu Tyr Glu Glu Asn Asp Glu Ser Glu Val Glu Ile Ile His Val Thr
1               5                   10                  15

Ser Pro Met Leu Glu Thr Arg Arg Ala Asp Ser Phe Arg Tyr
            20                  25                  30

<210> SEQ ID NO 14
<211> LENGTH: 15
<212> TYPE: PRT
<213> ORGANISM: Artificial
<220> FEATURE:
<223> OTHER INFORMATION: EIL peptide variant

<400> SEQUENCE: 14

Ser Leu Arg Phe Leu Phe Ala Gly Gln Arg Ile Ala Asp Asn His
1               5                   10                  15

<210> SEQ ID NO 15
<211> LENGTH: 15
<212> TYPE: PRT
<213> ORGANISM: Artificial
```

```
<220> FEATURE:
<223> OTHER INFORMATION: EIL peptide variant

<400> SEQUENCE: 15

Ser Leu Arg Phe Leu Tyr Glu Gly Gln Arg Ile Ala Asp Asn His
1               5                   10                  15

<210> SEQ ID NO 16
<211> LENGTH: 15
<212> TYPE: PRT
<213> ORGANISM: Artificial
<220> FEATURE:
<223> OTHER INFORMATION: EIL peptide variant

<400> SEQUENCE: 16

Ser Leu Arg Phe Leu Phe Glu Gly Gln Arg Ile Ala Asp Asn Arg
1               5                   10                  15

<210> SEQ ID NO 17
<211> LENGTH: 15
<212> TYPE: PRT
<213> ORGANISM: Artificial
<220> FEATURE:
<223> OTHER INFORMATION: EIL peptide variant

<400> SEQUENCE: 17

Ser Leu Arg Phe Leu Phe Asp Gly Gln Arg Ile Ala Asp Asn His
1               5                   10                  15

<210> SEQ ID NO 18
<211> LENGTH: 15
<212> TYPE: PRT
<213> ORGANISM: Artificial
<220> FEATURE:
<223> OTHER INFORMATION: EIL peptide variant

<400> SEQUENCE: 18

Ser Leu Arg Phe Leu Trp Glu Gly Gln Arg Ile Ala Asp Asn His
1               5                   10                  15

<210> SEQ ID NO 19
<211> LENGTH: 15
<212> TYPE: PRT
<213> ORGANISM: Artificial
<220> FEATURE:
<223> OTHER INFORMATION: EIL peptide variant

<400> SEQUENCE: 19

Ser Leu Arg Phe Leu Val Glu Gly Gln Arg Ile Ala Asp Asn His
1               5                   10                  15

<210> SEQ ID NO 20
<211> LENGTH: 15
<212> TYPE: PRT
<213> ORGANISM: Artificial
<220> FEATURE:
<223> OTHER INFORMATION: EIL peptide variant

<400> SEQUENCE: 20

Ser Leu Arg Phe Leu Ala Glu Gly Gln Arg Ile Ala Asp Asn His
1               5                   10                  15

<210> SEQ ID NO 21
<211> LENGTH: 15
<212> TYPE: PRT
<213> ORGANISM: Artificial
<220> FEATURE:
```

<223> OTHER INFORMATION: EIL peptide variant

<400> SEQUENCE: 21

Ser Leu Arg Phe Leu Phe Glu Ala Gln Arg Ile Ala Asp Asn His
1               5                   10                  15

<210> SEQ ID NO 22
<211> LENGTH: 14
<212> TYPE: PRT
<213> ORGANISM: Artificial
<220> FEATURE:
<223> OTHER INFORMATION: EIL peptide variant

<400> SEQUENCE: 22

Leu Arg Phe Leu Phe Glu Gly Gln Arg Ile Ala Asp Asn His
1               5                   10

<210> SEQ ID NO 23
<211> LENGTH: 13
<212> TYPE: PRT
<213> ORGANISM: Artificial
<220> FEATURE:
<223> OTHER INFORMATION: EIL peptide variant

<400> SEQUENCE: 23

Arg Phe Leu Phe Glu Gly Gln Arg Ile Ala Asp Asn His
1               5                   10

<210> SEQ ID NO 24
<211> LENGTH: 11
<212> TYPE: PRT
<213> ORGANISM: Artificial
<220> FEATURE:
<223> OTHER INFORMATION: EIL peptide variant

<400> SEQUENCE: 24

Leu Phe Glu Gly Gln Arg Ile Ala Asp Asn His
1               5                   10

<210> SEQ ID NO 25
<211> LENGTH: 10
<212> TYPE: PRT
<213> ORGANISM: Artificial
<220> FEATURE:
<223> OTHER INFORMATION: EIL peptide variant

<400> SEQUENCE: 25

Phe Glu Gly Gln Arg Ile Ala Asp Asn His
1               5                   10

<210> SEQ ID NO 26
<211> LENGTH: 13
<212> TYPE: PRT
<213> ORGANISM: Artificial
<220> FEATURE:
<223> OTHER INFORMATION: EIL peptide variant

<400> SEQUENCE: 26

Ser Leu Arg Phe Leu Phe Glu Gly Gln Arg Ile Ala Asp
1               5                   10

<210> SEQ ID NO 27
<211> LENGTH: 11
<212> TYPE: PRT
<213> ORGANISM: Artificial
<220> FEATURE:
<223> OTHER INFORMATION: EIL peptide variant

<400> SEQUENCE: 27

Ser Leu Arg Phe Leu Phe Glu Gly Gln Arg Ile
1               5                   10

<210> SEQ ID NO 28
<211> LENGTH: 10
<212> TYPE: PRT
<213> ORGANISM: Artificial
<220> FEATURE:
<223> OTHER INFORMATION: EIL peptide variant

<400> SEQUENCE: 28

Ser Leu Arg Phe Leu Phe Glu Gly Gln Arg
1               5                   10

<210> SEQ ID NO 29
<211> LENGTH: 9
<212> TYPE: PRT
<213> ORGANISM: Artificial
<220> FEATURE:
<223> OTHER INFORMATION: EIL peptide variant

<400> SEQUENCE: 29

Ser Leu Arg Phe Leu Phe Glu Gly Gln
1               5

<210> SEQ ID NO 30
<211> LENGTH: 13
<212> TYPE: PRT
<213> ORGANISM: Artificial
<220> FEATURE:
<223> OTHER INFORMATION: EIL peptide variant

<400> SEQUENCE: 30

Leu Arg Phe Leu Phe Glu Gly Gln Arg Ile Ala Asp Asn
1               5                   10

<210> SEQ ID NO 31
<211> LENGTH: 11
<212> TYPE: PRT
<213> ORGANISM: Artificial
<220> FEATURE:
<223> OTHER INFORMATION: EIL peptide variant

<400> SEQUENCE: 31

Arg Phe Leu Phe Glu Gly Gln Arg Ile Ala Asp
1               5                   10

<210> SEQ ID NO 32
<211> LENGTH: 9
<212> TYPE: PRT
<213> ORGANISM: Artificial
<220> FEATURE:
<223> OTHER INFORMATION: EIL peptide variant

<400> SEQUENCE: 32

Phe Leu Phe Glu Gly Gln Arg Ile Ala
1               5

<210> SEQ ID NO 33
<211> LENGTH: 8
<212> TYPE: PRT
<213> ORGANISM: Artificial
<220> FEATURE:
<223> OTHER INFORMATION: EIL peptide variant

```
<400> SEQUENCE: 33

Phe Leu Phe Glu Gly Gln Arg Ile
1               5

<210> SEQ ID NO 34
<211> LENGTH: 6
<212> TYPE: PRT
<213> ORGANISM: Artificial
<220> FEATURE:
<223> OTHER INFORMATION: EIL peptide variant

<400> SEQUENCE: 34

Leu Phe Glu Gly Gln Arg
1               5

<210> SEQ ID NO 35
<211> LENGTH: 8
<212> TYPE: PRT
<213> ORGANISM: Artificial
<220> FEATURE:
<223> OTHER INFORMATION: EIL peptide variant

<400> SEQUENCE: 35

Phe Leu Ile Glu Gly Gln Arg Ile
1               5

<210> SEQ ID NO 36
<211> LENGTH: 8
<212> TYPE: PRT
<213> ORGANISM: Artificial
<220> FEATURE:
<223> OTHER INFORMATION: EIL minimal sequence

<400> SEQUENCE: 36

Ser Leu Arg Phe Leu Phe Glu Gly
1               5

<210> SEQ ID NO 37
<211> LENGTH: 8
<212> TYPE: PRT
<213> ORGANISM: Artificial
<220> FEATURE:
<223> OTHER INFORMATION: EIL variant peptide

<400> SEQUENCE: 37

Ser Leu Arg Phe Leu Tyr Glu Gly
1               5

<210> SEQ ID NO 38
<211> LENGTH: 8
<212> TYPE: PRT
<213> ORGANISM: Artificial
<220> FEATURE:
<223> OTHER INFORMATION: EIL variant peptide

<400> SEQUENCE: 38

Ser Leu Arg Phe Leu Phe Ala Gly
1               5

<210> SEQ ID NO 39
<211> LENGTH: 8
<212> TYPE: PRT
<213> ORGANISM: Artificial
<220> FEATURE:
<223> OTHER INFORMATION: EIL variant peptide

<400> SEQUENCE: 39
```

```
Ser Leu Arg Phe Leu Tyr Ala Gly
1               5

<210> SEQ ID NO 40
<211> LENGTH: 8
<212> TYPE: PRT
<213> ORGANISM: Artificial
<220> FEATURE:
<223> OTHER INFORMATION: EIL variant peptide

<400> SEQUENCE: 40

Thr Leu Arg Phe Leu Phe Glu Gly
1               5

<210> SEQ ID NO 41
<211> LENGTH: 8
<212> TYPE: PRT
<213> ORGANISM: Artificial
<220> FEATURE:
<223> OTHER INFORMATION: EIL variant peptide
<220> FEATURE:
<221> NAME/KEY: ACETYLATION
<222> LOCATION: (1)..(1)

<400> SEQUENCE: 41

Ser Leu Arg Phe Leu Phe Glu Gly
1               5

<210> SEQ ID NO 42
<211> LENGTH: 8
<212> TYPE: PRT
<213> ORGANISM: Artificial
<220> FEATURE:
<223> OTHER INFORMATION: EIL variant peptide
<220> FEATURE:
<221> NAME/KEY: ACETYLATION
<222> LOCATION: (1)..(1)

<400> SEQUENCE: 42

Ser Leu Arg Phe Leu Tyr Glu Gly
1               5

<210> SEQ ID NO 43
<211> LENGTH: 11
<212> TYPE: PRT
<213> ORGANISM: Artificial
<220> FEATURE:
<223> OTHER INFORMATION: EIL variant peptide

<400> SEQUENCE: 43

Ala Ala Ala Ser Leu Arg Phe Leu Tyr Glu Gly
1               5                   10

<210> SEQ ID NO 44
<211> LENGTH: 11
<212> TYPE: PRT
<213> ORGANISM: Artificial
<220> FEATURE:
<223> OTHER INFORMATION: EIL variant peptide

<400> SEQUENCE: 44

Ser Leu Arg Phe Leu Tyr Glu Gly Ala Ala Ala
1               5                   10

<210> SEQ ID NO 45
<211> LENGTH: 12
<212> TYPE: PRT
```

-continued

```
<213> ORGANISM: Artificial
<220> FEATURE:
<223> OTHER INFORMATION: EIL variant peptide

<400> SEQUENCE: 45

Arg Arg Arg Arg Ser Leu Arg Phe Leu Phe Glu Gly
1               5                   10

<210> SEQ ID NO 46
<211> LENGTH: 12
<212> TYPE: PRT
<213> ORGANISM: Artificial
<220> FEATURE:
<223> OTHER INFORMATION: EIL variant peptide

<400> SEQUENCE: 46

Arg Arg Arg Arg Ser Leu Arg Phe Leu Tyr Ala Gly
1               5                   10

<210> SEQ ID NO 47
<211> LENGTH: 21
<212> TYPE: PRT
<213> ORGANISM: Artificial
<220> FEATURE:
<223> OTHER INFORMATION: Peptide 1

<400> SEQUENCE: 47

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 48
<211> LENGTH: 20
<212> TYPE: PRT
<213> ORGANISM: Artificial
<220> FEATURE:
<223> OTHER INFORMATION: DPP9/DPP8 inhibitor consensus sequence
<220> FEATURE:
<221> NAME/KEY: misc_feature
<222> LOCATION: (1)..(1)
<223> OTHER INFORMATION: wherein Xaa is Ser or Thr, preferably wherein
      Xaa is Ser
<220> FEATURE:
<221> NAME/KEY: misc_feature
<222> LOCATION: (6)..(6)
<223> OTHER INFORMATION: wherein Xaa is Phe, Tyr, Trp, Val or Ile,
      preferably wherein Xaa is Phe, Tyr, Trp, or Val, more preferably
      wherein  Xaa is Phe or Tyr
<220> FEATURE:
<221> NAME/KEY: misc_feature
<222> LOCATION: (7)..(7)
<223> OTHER INFORMATION: wherein Xaa is Ala or Glu
<220> FEATURE:
<221> NAME/KEY: misc_feature
<222> LOCATION: (8)..(8)
<223> OTHER INFORMATION: wherein Xaa is Gly or Ala
<220> FEATURE:
<221> NAME/KEY: misc_feature
<222> LOCATION: (9)..(9)
<223> OTHER INFORMATION: wherein Xaa is missing or wherein Xaa is any
      amino acid, preferably wherein Xaa is Gln
<220> FEATURE:
<221> NAME/KEY: misc_feature
<222> LOCATION: (10)..(10)
<223> OTHER INFORMATION: wherein Xaa is missing or wherein Xaa is any
      amino acid, preferably wherein Xaa is Arg
<220> FEATURE:
<221> NAME/KEY: misc_feature
<222> LOCATION: (11)..(11)
<223> OTHER INFORMATION: wherein Xaa is missing or wherein Xaa is any
      amino acid, preferably wherein Xaa is Ile
```

```
<220> FEATURE:
<221> NAME/KEY: misc_feature
<222> LOCATION: (12)..(12)
<223> OTHER INFORMATION: wherein Xaa is missing or wherein Xaa is any
      amino acid, preferably wherein Xaa is Ala
<220> FEATURE:
<221> NAME/KEY: misc_feature
<222> LOCATION: (13)..(13)
<223> OTHER INFORMATION: wherein Xaa is missing or wherein Xaa is any
      amino acid, preferably wherein Xaa is Asp
<220> FEATURE:
<221> NAME/KEY: misc_feature
<222> LOCATION: (14)..(14)
<223> OTHER INFORMATION: wherein Xaa is missing or wherein Xaa is any
      amino acid, preferably wherein Xaa is Asn
<220> FEATURE:
<221> NAME/KEY: misc_feature
<222> LOCATION: (15)..(15)
<223> OTHER INFORMATION: wherein Xaa is missing or wherein Xaa is any
      amino acid, preferably wherein Xaa is His
<220> FEATURE:
<221> NAME/KEY: misc_feature
<222> LOCATION: (16)..(16)
<223> OTHER INFORMATION: wherein Xaa is missing or wherein Xaa is any
      amino acid, preferably wherein Xaa is Arg
<220> FEATURE:
<221> NAME/KEY: misc_feature
<222> LOCATION: (17)..(17)
<223> OTHER INFORMATION: wherein Xaa is missing or wherein Xaa is any
      amino acid, preferably wherein Xaa is Arg
<220> FEATURE:
<221> NAME/KEY: misc_feature
<222> LOCATION: (18)..(18)
<223> OTHER INFORMATION: wherein Xaa is missing or wherein Xaa is any
      amino acid, preferably wherein Xaa is Arg
<220> FEATURE:
<221> NAME/KEY: misc_feature
<222> LOCATION: (19)..(19)
<223> OTHER INFORMATION: wherein Xaa is missing or wherein Xaa is any
      amino acid, preferably wherein Xaa is Arg
<220> FEATURE:
<221> NAME/KEY: misc_feature
<222> LOCATION: (20)..(20)
<223> OTHER INFORMATION: wherein Xaa is missing or wherein Xaa is any
      amino acid, preferably wherein Xaa is Arg

<400> SEQUENCE: 48

Xaa Leu Arg Phe Leu Xaa Xaa Xaa Xaa Xaa Xaa Xaa Xaa Xaa Xaa Xaa
1               5                   10                  15

Xaa Xaa Xaa Xaa
            20

<210> SEQ ID NO 49
<211> LENGTH: 20
<212> TYPE: PRT
<213> ORGANISM: Artificial
<220> FEATURE:
<223> OTHER INFORMATION: SUMO1 inhibitor consensus sequence
<220> FEATURE:
<221> NAME/KEY: misc_feature
<222> LOCATION: (3)..(3)
<223> OTHER INFORMATION: wherein Xaa is any amino acid, preferably
      wherein Xaa is Val, Ile or Ala, preferably wherein Xaa is Val or
      Ile
<220> FEATURE:
<221> NAME/KEY: misc_feature
<222> LOCATION: (7)..(7)
<223> OTHER INFORMATION: wherein Xaa is Pro or Thr
<220> FEATURE:
<221> NAME/KEY: misc_feature
<222> LOCATION: (10)..(10)
<223> OTHER INFORMATION: wherein Xaa is Ala or Met
<220> FEATURE:
<221> NAME/KEY: misc_feature
<222> LOCATION: (13)..(13)
<223> OTHER INFORMATION: wherein Xaa is Glu or Thr
```

```
<220> FEATURE:
<221> NAME/KEY: misc_feature
<222> LOCATION: (15)..(15)
<223> OTHER INFORMATION: wherein Xaa is Lys or Arg
<220> FEATURE:
<221> NAME/KEY: misc_feature
<222> LOCATION: (16)..(16)
<223> OTHER INFORMATION: wherein Xaa is Thr or Ala
<220> FEATURE:
<221> NAME/KEY: misc_feature
<222> LOCATION: (19)..(19)
<223> OTHER INFORMATION: wherein Xaa is Tyr or Phe

<400> SEQUENCE: 49

Val Glu Xaa Ile His Val Xaa Ser Pro Xaa Leu Glu Xaa Arg Xaa Xaa
1               5                   10                  15

Asp Ser Xaa Arg
            20
```